United States Patent
Klee et al.

(10) Patent No.: US 11,166,883 B2
(45) Date of Patent: Nov. 9, 2021

(54) DENTAL COMPOSITION

(71) Applicant: DENTSPLY SIRONA inc., York, PA (US)

(72) Inventors: Joachim E Klee, Radolfzell (DE); Maximilian Maier, Constance (DE); Christoph P. Fik, Schonenberg a.d. Thur (CH); Jacques Lalevee, Mulhouse (FR); Jean Pierre Fouassier, St. Hippolyte (FR); Fabrice Morlet-Savary, Pfastatt (FR); Celine Dietlin, Mulhouse (FR); Mariem Bouzrati-Zerelli, Mulhouse (FR)

(73) Assignee: DENTSPLY SIRONA Inc., York, PA (US)

( * ) Notice: Subject to any disclaimer, the term of this patent is extended or adjusted under 35 U.S.C. 154(b) by 101 days.

(21) Appl. No.: 16/092,658

(22) PCT Filed: Apr. 7, 2017

(86) PCT No.: PCT/EP2017/058452
§ 371 (c)(1),
(2) Date: Oct. 10, 2018

(87) PCT Pub. No.: WO2017/178383
PCT Pub. Date: Oct. 19, 2017

(65) Prior Publication Data
US 2019/0117522 A1 Apr. 25, 2019

(30) Foreign Application Priority Data
Apr. 11, 2016 (EP) ..................................... 16164674

(51) Int. Cl.
*A61K 6/88* (2020.01)
*A61K 6/887* (2020.01)
(Continued)

(52) U.S. Cl.
CPC ................ *A61K 6/887* (2020.01); *A61K 6/54* (2020.01); *A61K 6/62* (2020.01); *A61K 6/889* (2020.01)

(58) Field of Classification Search
CPC . A61K 6/54; A61K 6/62; A61K 6/887; A61K 6/889
(Continued)

(56) References Cited

U.S. PATENT DOCUMENTS 7,605,190 B2 * 10/2009 Moszner .................... C08F 2/50
522/66
8,829,067 B2 * 9/2014 Moszner .................... C08F 4/16
522/66

(Continued)

FOREIGN PATENT DOCUMENTS

EP 1548021 A1 6/2005
EP 1905415 A1 4/2008
(Continued)

*Primary Examiner* — Sanza L. McClendon
(74) *Attorney, Agent, or Firm* — DENTSPLY SIRONA Inc

(57) ABSTRACT

Dental composition comprising
(a) a homogeneous phase comprising monomer combinations (i) and (ii), (i) and (iii), (ii) and (iii), or (i), (ii) and (iii), or comprising monomer (iii), wherein
(i) represents one or more compounds having one or more radically polymerizable carbon-carbon double bonds;
(ii) represents one or more compounds having one or more cationically polymerizable groups; and
(iii) represents one or more compounds having a combination of one or more radically polymerizable carbon-carbon double bonds and one or more cationically polymerizable groups;
(b) an initiator system comprising
(iv) one or more radical polymerization initiator of the following formula (I):

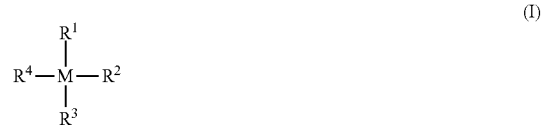

(I)

wherein
M is Ge or Si;
$R^1$, $R^2$ and $R^3$ may be the same or different, independently represent an organic group, and
$R^4$ represents a hydrogen atom, an organic or organometallic group; provided that when $R^4$ is a hydrogen atom, the initiator system further comprises a sensitizer compound having a light absorption maximum in the range from 300 to 600 nm;
(v) a cationic polymerization initiator, which is a compound selected from the following formula (II), (III) and (IV):

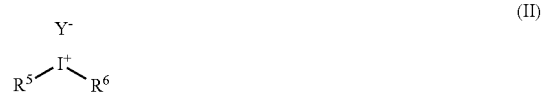

(II)

wherein
$R^5$ and $R^6$, which may be the same or different, independently represent an aryl group which may have a substituent; and
$Y^-$ represents an anion;

(III)

(Continued)

wherein

R⁷, R⁸ and R⁹ which may be the same or different, independently represent an aryl group which may have a substituent; and Y⁻ represents an anion;

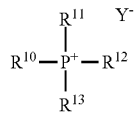

(IV)

R¹⁰, R¹¹, R¹², and R¹³ which may be the same or different, independently represent an alkyl or aryl group which may have a substituent; and Y⁻ represents an anion.

15 Claims, 16 Drawing Sheets

(51) Int. Cl.
*A61K 6/54* (2020.01)
*A61K 6/62* (2020.01)
*A61K 6/889* (2020.01)

(58) Field of Classification Search
USPC .................. 523/114, 115, 116, 118, 120, 117
See application file for complete search history.

(56) References Cited

U.S. PATENT DOCUMENTS 10,322,097 B2 * 6/2019 Wong ..................... A61K 33/24
10,512,594 B2 * 12/2019 Klee ......................... A61K 6/20

FOREIGN PATENT DOCUMENTS

| EP | 2103297 | A1 | 9/2009 |
| EP | 2604247 | A1 | 6/2013 |
| EP | 2705827 | A1 | 3/2014 |
| EP | 2727576 | A1 | 5/2014 |

\* cited by examiner

DENTAL COMPOSITION

FIELD OF THE INVENTION

The present invention relates to a dental composition comprising a specific homogeneous phase comprising a monomer or a combination of monomers so that radically polymerizable carbon-carbon double bonds and cationically polymerizable groups are present in the homogeneous phase. The dental composition further comprises a specific initiator system for initiating radical polymerization and cationic polymerization.

BACKGROUND OF THE INVENTION

The restoration of teeth commonly involves a light curable dental composition containing free-radically polymerizable compounds. Light curing of a dental composition involves a photoinitiator system generating free radicals upon exposure to visible light. Free radicals may be typically produced by either of two pathways:
(1) the photoinitiator compound undergoes excitation by energy absorption with subsequent decomposition of the compound into one or more radicals (Norrish type I), or
(2) the photoinitiator compound undergoes excitation and the excited photoinitiator compound interacts with a second compound by either energy transfer or a redox reaction to form free radicals from any of the compounds (Norrish type II).

A photoinitiator is required to provide high quantum yields for the conversion of radiation to radicals given the interaction of the radiation with other components of the dental composition. Even with a good quantum yield the conversion of the polymerizable groups in a polymerization of a conventional dental composition is only about 70 percent. The mechanical strength of the polymerized dental composition is, therefore, less than optimal and unreacted monomers may leach out of the polymerized dental composition. The leaching problem may lead to a toxicological problem. In order to alleviate this problem, multifunctional monomers are frequently used which are more likely to be included in the polymer network.

In addition, photoinitiators are required to have a high acid resistance, solubility, thermal stability, and storage stability when incorporated into a dental composition.

Finally, given that dental compositions usually contain (meth)acrylate or (meth)acrylamide monomers, free radical photocuring may be inhibited by the presence of oxygen. Oxygen inhibition is due to the rapid reaction of propagating radicals with oxygen molecules to yield peroxyl radicals which are not as reactive towards carbon-carbon unsaturated double bonds and therefore do not initiate or participate in any photopolymerization reaction. Oxygen inhibition may lead to premature chain termination and, therefore, incomplete photocuring. Nevertheless, a certain degree of oxygen inhibition on the top surface of the adhesive layer is required for the bonding to the adjacent restorative.

Accordingly, the initiator system has a critical influence on the quality of the dental material. Conventionally, camphor quinone optionally in combination with a tertiary amine, or 2,4,6-trimethylbenzoylphenyl phosphinate (Irgacure® TPO) are frequently used as a photoinitiator system. However, the presence of amines in acrylate-containing compositions causes yellowing in the resulting photocured composition, creates undesirable odors, and may soften the cured composition because of chain transfer reactions and, therefore, often requires the use of stabilizers. Moreover, the use of aromatic amines gives rise to toxicological concerns.

Furthermore, it is desirable that the light activating the photoinitiator system, has a sufficiently long wavelength in order to avoid damage of soft tissue during polymerization of the dental composition in the mouth of the patient. Accordingly, the photoinitiator system is required to contain a chromophoric group efficiently absorbing light of the desired wavelength in a range of from 400 to 800 nm. However, an increase of the absorption coefficient of the photoinitiator system increases the coloration of the photoinitiator system and thereby the coloration of the dental composition before light curing. Accordingly, it is necessary that the chromophoric groups are efficiently destroyed during polymerization so that the coloration of the initiator system disappears in the polymerized dental composition by the so-called "photo-bleaching". A destruction of the chromophoric groups during polymerization may also be useful in increasing the depth of cure of the dental composition since activating light is not shielded from unpolymerized layers of the dental composition by the photoinitiator system present in polymerized layers covering the unpolymerized layers. Cationically polymerizable groups may also be present in a dental composition. Dental compositions comprising a combination of compounds having free-radically polymerizable groups and compound(s) having cationically polymerizable groups are known to form a so-called "interpenetrating polymer network" (IPN). An IPN includes two or more polymers which are at least partially interlaced on a molecular scale but not covalently bonded to each other and cannot be separated unless chemical bonds are broken. The formation of an IPN allows to adjust both chemical and mechanical properties of the cured dental composition.

Dental compositions forming IPNs are known. For example, WO 2015/157329 A1 discloses a dental composition capable of forming an IPN, which dental composition comprises: (1) at least one cationically reactive compound; (2) at least one cationic photoinitiator in the form of a iodonium salt (3) at least one compound which is: an organic monomer, oligomer or polymer, said compound comprising at least one reactive oxirane, oxetane, or alkenyl ether; (4) at least one compound which is: an organic monomer, oligomer or polymer, said compound comprising at least one reactive acrylate; and (5) at least one free radical initiator in the from of an aromatic ketone or a diketone such a camphor quinone; and (6) at least one compound which is: an organic monomer, oligomer or polymer, said compound comprising at least one reactive acrylate or methacrylate and at least one oxirane, oxetane, or alkenyl ether.

EP 1 905 415 A1 and EP 2 103 297 A1 discloses dental compositions comprising a polymerizable binder which comprises a radically polymerizing monomer and/or a cationically polymerizing monomer, and a photoinitiator containing an acylgermanium compound.

SUMMARY OF THE INVENTION

It is the problem of the present invention to provide a dental composition which provides
 reduced polymerisation shrinkage and stress,
 improved polymerization efficiency including a high conversion and good curing rate which may be adapted to provide a suitable working time of the composition,
 improved depth of cure,
 improved mechanical properties, and
 absence of coloration problems.

The present invention provides a dental composition comprising (a) a homogeneous phase comprising monomer combinations (i) and (ii), (i) and (iii), (ii) and (iii), or (i), (ii) and (iii), or comprising monomer (iii), wherein (i) represents one or more compounds having one or more radically polymerizable carbon-carbon double bonds;

(ii) represents one or more compounds having one or more cationically polymerizable groups; and (iii) represents one or more compounds having a combination of one or more radically polymerizable carbon-carbon double bonds and one or more cationically polymerizable groups;

(b) an initiator system comprising (iv) one or more radical polymerization initiators of the following formula (I):

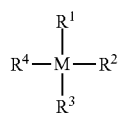
(I)

wherein

M is Ge or Si; $R^1$, $R^2$ and $R^3$ may be the same or different, independently represent an organic group, and $R^4$ represents a hydrogen atom, an organic or organometallic group; provided that when $R^4$ is a hydrogen atom, the initiator system further comprises a sensitizer compound having a light absorption maximum in the range from 300 to 600 nm;

(v) a cationic polymerization initiator, which is a compound selected from the following formula (II), (III) and (IV):

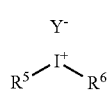
(II)

wherein $R^5$ and $R^6$, which may be the same or different, independently represent an aryl group which may have a substituent; and $Y^-$ represents an anion;

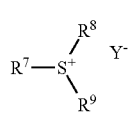
(III)

wherein $R^7$, $R^8$ and $R^9$ which may be the same or different, independently represent an aryl group which may have a substituent; and $Y^-$ represents an anion;

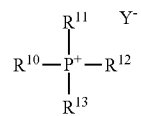
(IV)

$R^{10}$, $R^{11}$, $R^{12}$, and $R^{13}$ which may be the same or different, independently represent an alkyl or aryl group which may have a substituent; and $Y^-$ represents an anion.

The present invention is based on the recognition that a dental composition comprising the specific combination of homogeneous phase (a) and the initiator system (b) provides reduced polymerisation shrinkage and stress, and at the same time a higher degree of conversion leading to superior mechanical properties upon curing. In particular, it was found that the radical polymerization and cationic polymerisation in the presence of initiator system (b) do not interfere with each other. Rather, the effects of the present invention are attained by a polymerization wherein free radical polymerization proceeds at a fast rate and cationic polymerization proceeds at a slower rate, whereby polymerisation shrinkage and stress can significantly be reduced. Furthermore, a high polymerization efficiency provides cured dental compositions comprising hardly any unpolymerized compounds. Further, the present dental composition provides good esthetic effects, since undesired discoloration upon irradiation is effectively prevented. Accordingly, a relatively large amount of the dental composition can be photocured with reduced exposure to radiation. Due to the high efficiency of the initiator system (b), the presence of oxygen is not a serious detriment during photocuring of a dental composition according to the present invention.

In case the homogenous phase comprises monomer combinations (i) and (ii), (i) and (iii), (ii) and (iii), or (i), (ii) and (iii), interpenetrating polymer networks (IPNs) are provided.

In case the homogenous phase comprises only monomer(s) (iii), polymerisation shrinkage and stress can be reduced by a polymerization wherein free radical polymerization proceeds at a fast rate and cationic polymerization proceeds at a slower rate, whereby polymerisation shrinkage and stress can significantly be reduced.

BRIEF DESCRIPTION OF THE FIGURES

FIG. 9A), of the vinylether functions (cf. 9B) and of the global methacrylate and vinylether functions (cf. 9C) for the following blends:

Curve (1): UDMA/di(ethylene glycol) divinyl ether (DEGDVE) (75%/25% w/w);
curve (2): UDMA/DEGVE (75%/25% w/w); and
curve (3): UDMA/DVE-3 (75%/25% w/w).

These blends where polymerized in samples of 1.4 mm thickness under air in the presence of the initiator system DKSi/DPI (1.2%/1.2% w/w) upon the exposure to dental LED at 477 nm (SmartLite® Focus, 300 mW/cm$^2$).

Figure 10:
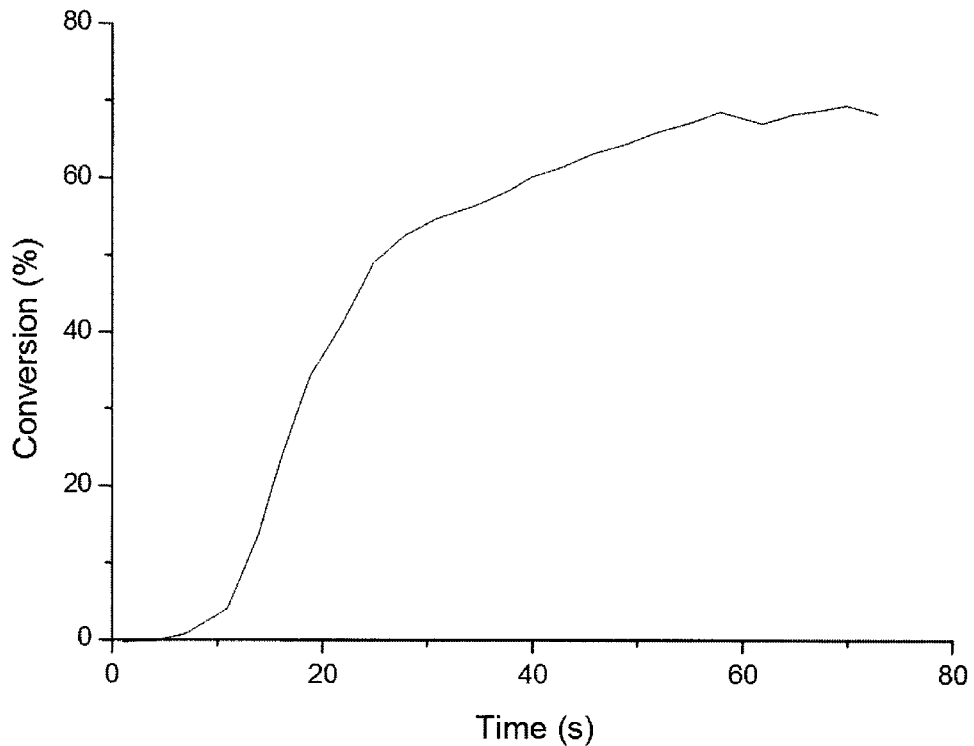

FIG. 10 shows the photopolymerization profile of a BisGMA/triethyleneglycol dimethacrylate (TEGDMA)/EPOX blend (75%/50% w/w) polymerized in samples of 20 µm thickness using under air in the presence of the initiator system CQ/Ph$_3$GeH/DPI (1%/2%/1% w/w) upon the exposure to dental LED at 477 nm (SmartLite® Focus).

Figure 11A:
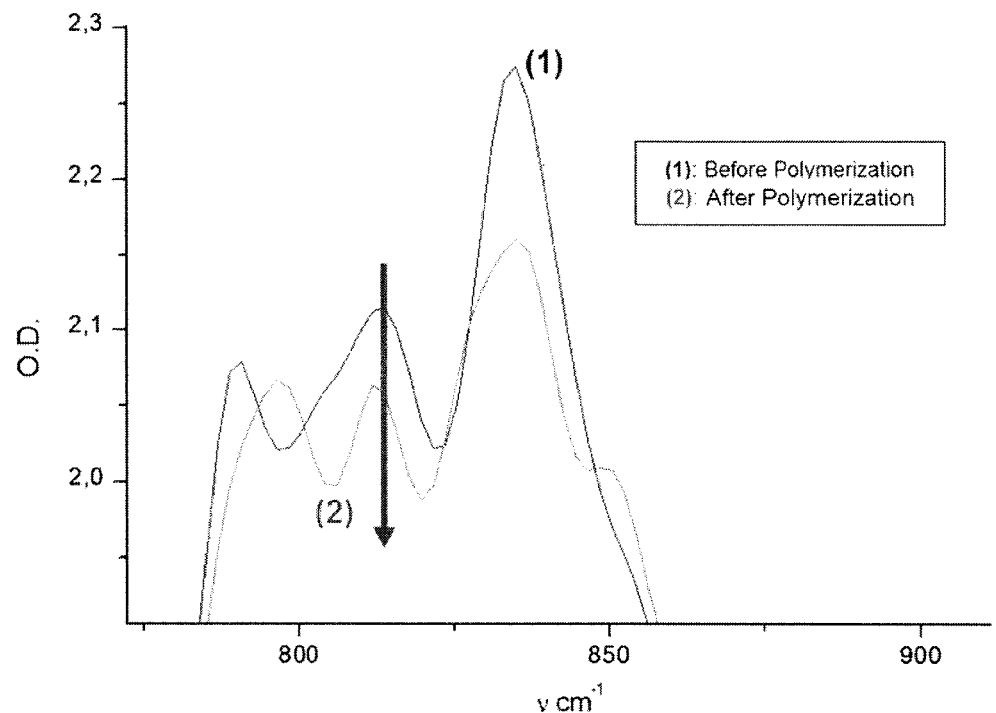
Figure 11B:
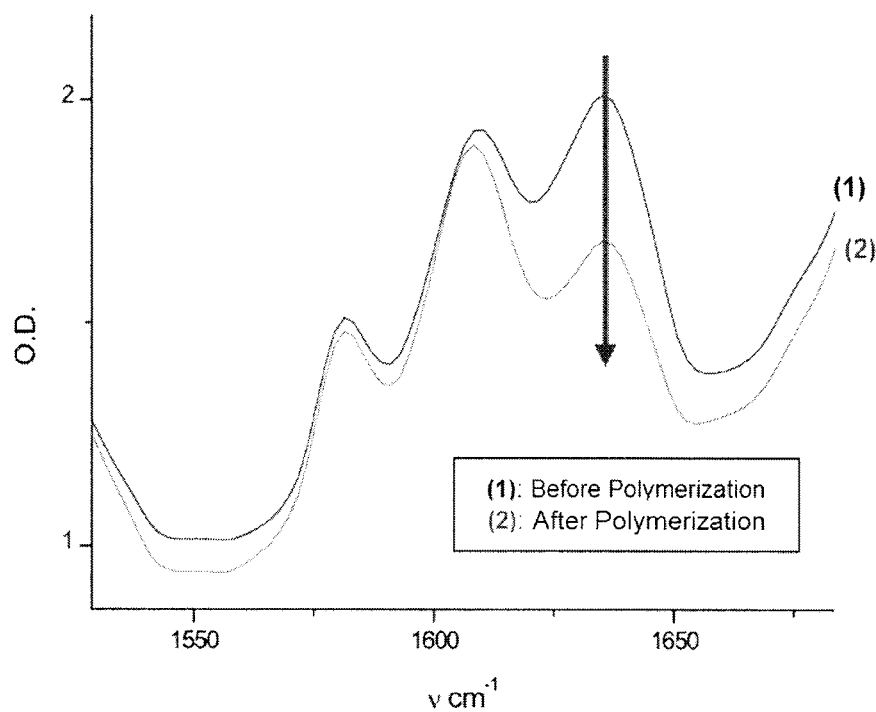
Figure 11C:
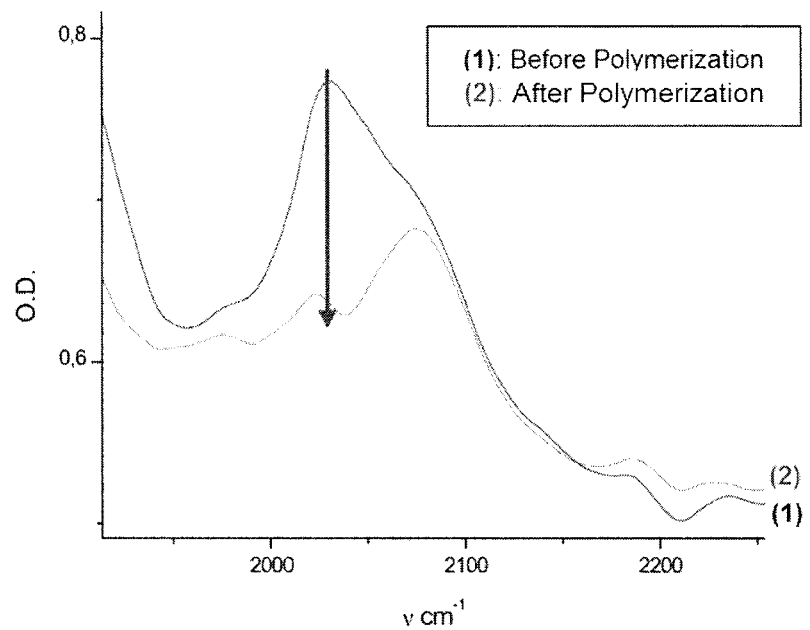

FIGS. 11A and 11 B and 11C show IR spectra of the samples of FIG. 10 before and after the photopolymerization. In particular, FIG. 11A shows the IR spectrum range of 775 to 900 cm$^{-1}$ for monitoring the conversion of the epoxide functions of EPOX, FIG. 11B shows the IR spectrum range of 1,500 to 1,700 cm$^{-1}$ for monitoring the conversion of the methacrylate functions of BisGMA and TEGDMA, and FIG. 11C shows the IR spectrum range of 1,900 to 2,250 cm$^{-1}$ for monitoring the conversion of the hydride function Ge—H of Ph$_3$GeH.

Figure 12A:
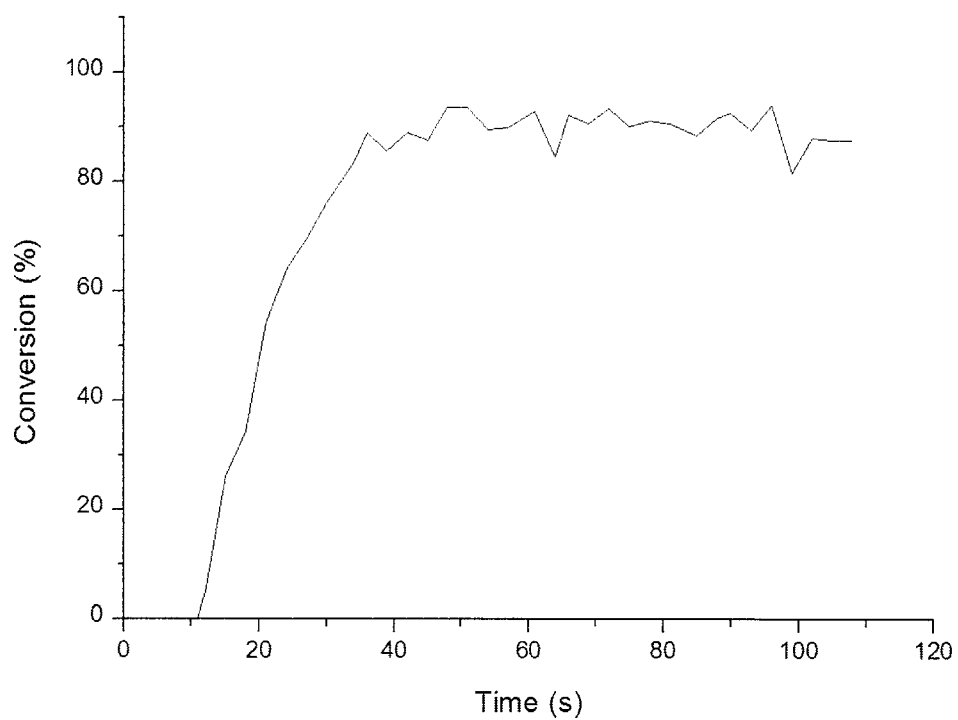

FIG. 12A shows the photopolymerization profile of a BisGMA/TEGDMA/EPOX (35%/15%/50% w/w) blend polymerized in samples of 1.4 mm thickness under air in the presence of the initiator system CQ/Ph$_3$GeH/DPI (1%/2%/1% w/w) upon the exposure to dental LED at 477 nm (SmartLite® Focus).

Figure 12B:
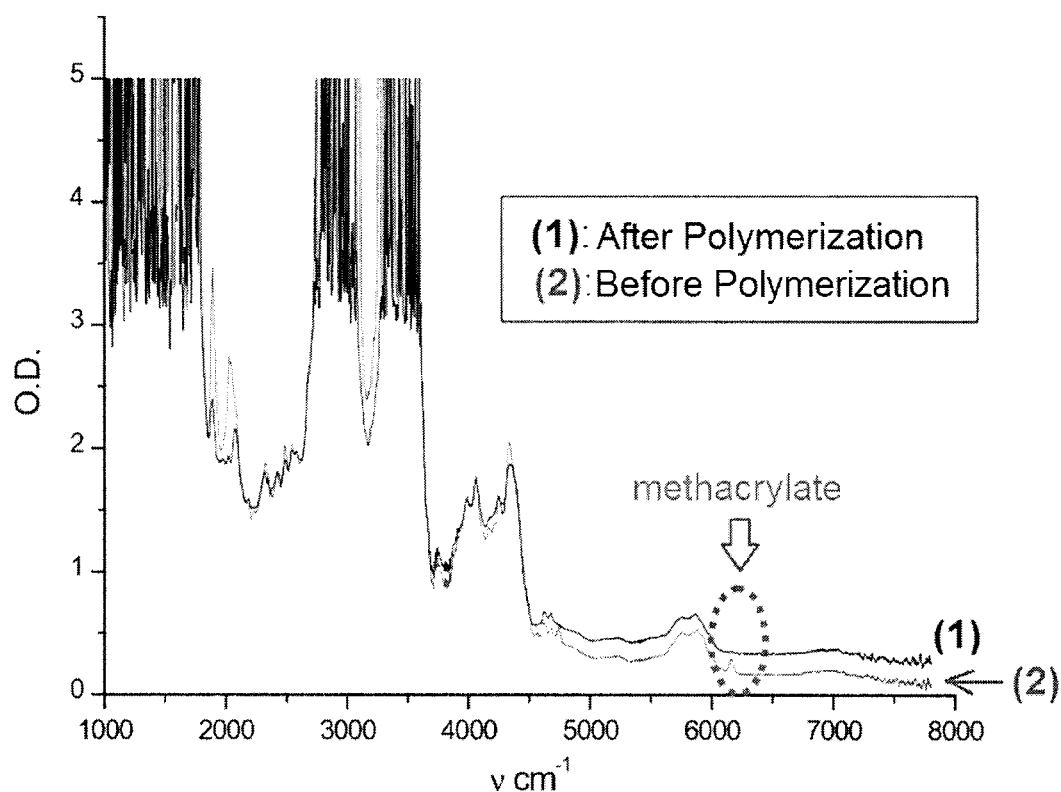

FIG. 12B shows the IR spectrum of the sample of FIG. 12A before and after photopolymerisation, wherein the wavelength range within which conversion of the methacrylate function before and after polymerization can be monitored.

Figure 13A:
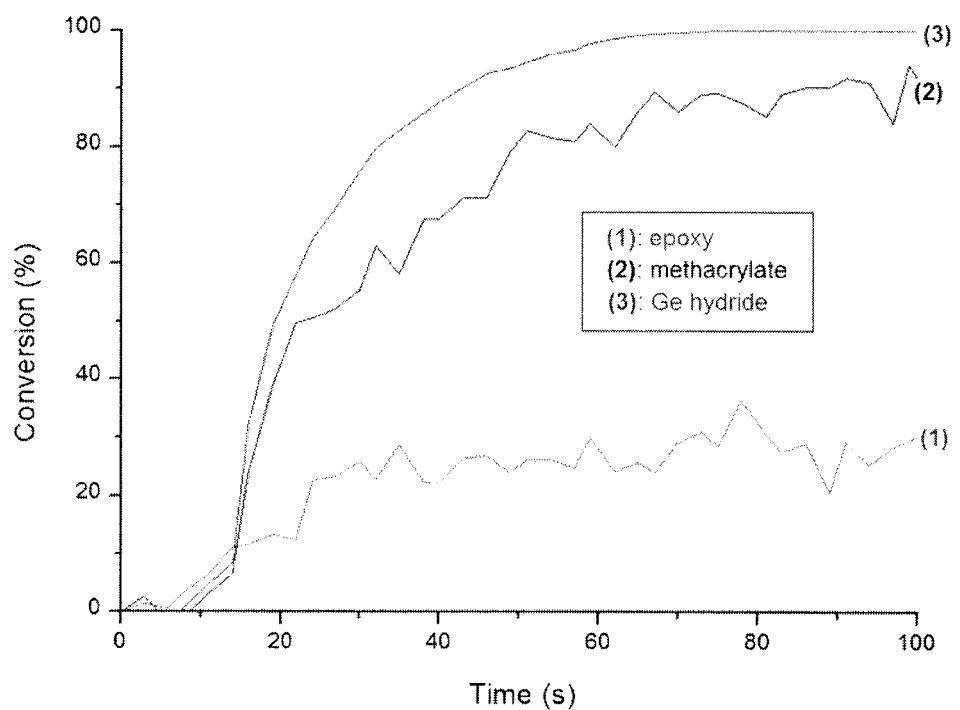

FIG. 13A shows photopolymerization profiles for a UDMA/EPOX-Si blend (50%/50% w/w) polymerized in samples of 1.4 mm thickness under air in the presence of the initiator system CQ/Ph$_3$GeH/PI2074 (2%/2%/2% w/w) upon the exposure to dental LED at 477 nm (SmartLite® Focus). Specifically, FIG. 13A shows the separate curves of conversion for the epoxy functions (cf. curve (1)), the methacrylate functions (cf. curve (2)), and the hydride (Ge—H) functions (cf. curve (3)) before and after polymerization.

Figure 13B:
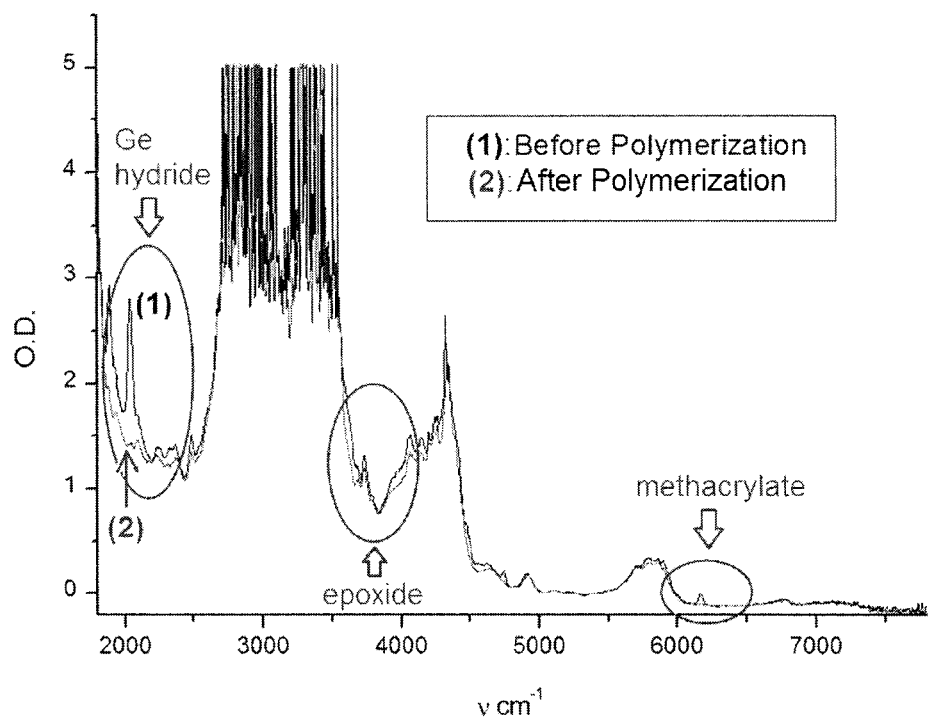
Figure 13C:
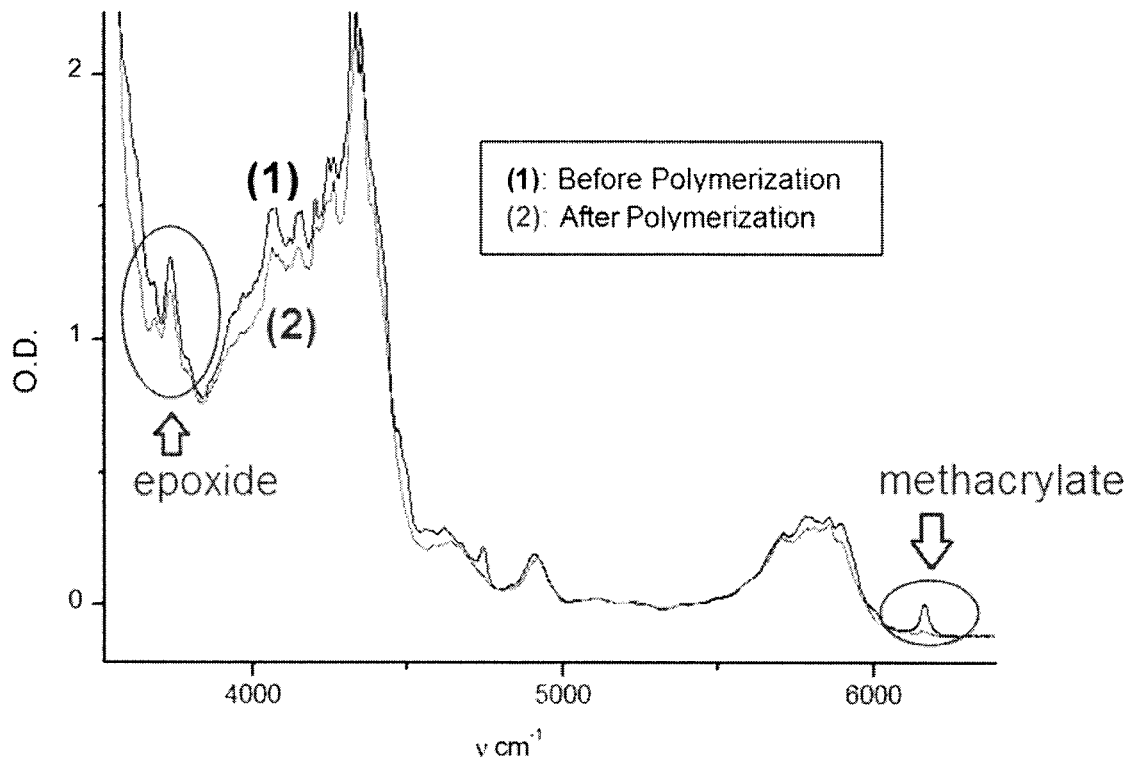

FIGS. 13B, and 13 C show different sections of an IR spectrum of the sample of FIG. 13A. Specifically, FIG. 13 B shows the IR spectrum range of about 2,000 to 7,000 cm$^{-1}$, wherein the ranges for monitoring the conversion of the Ge—H bond of Ph$_3$GeH, of the epoxide EPOX-Si and the methacrylate UDMA are indicated with ovals. FIG. 13C shows the IR spectrum range of about 3,500 to 6,500 cm$^{-1}$, wherein the ranges for monitoring the conversion of the epoxide EPOX-Si and the methacrylate UDMA are indicated with ovals.

Figure 14A:
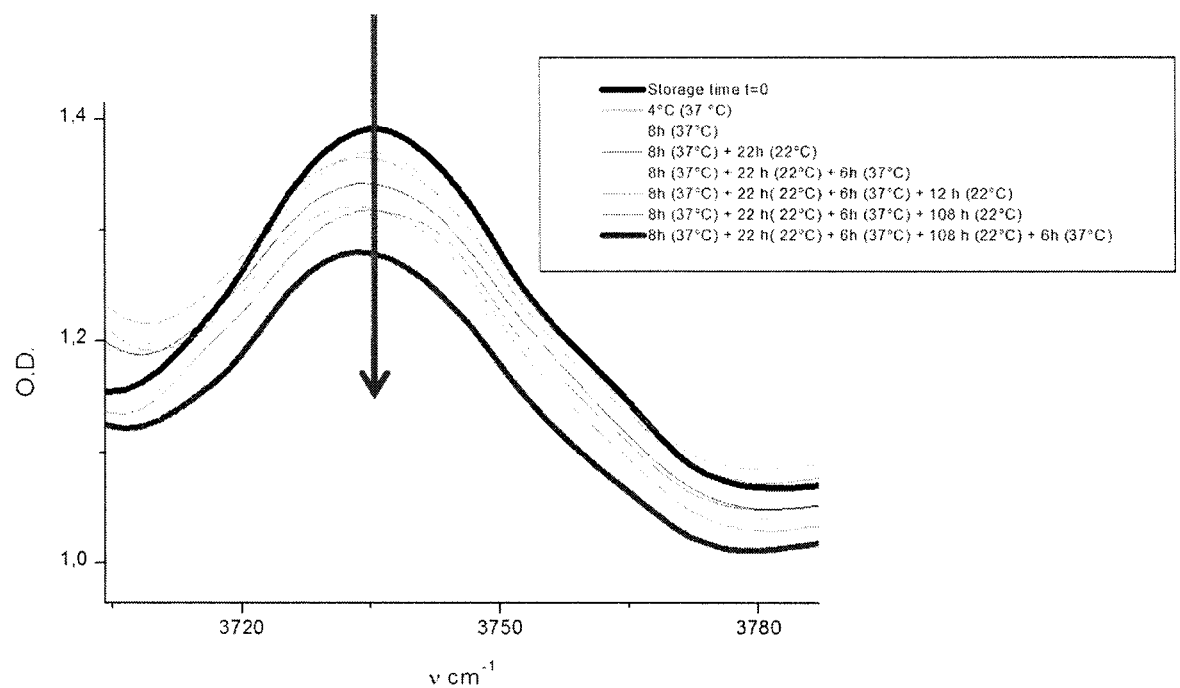

FIG. 14A shows the IR spectra sections containing the epoxy peak obtained for different storage times of the polymer obtained in FIG. 12. In the box to the right of the IR spectra, the storage times for the uppermost to the lowermost spectrum are indicated in order of appearance. That is, the uppermost spectrum is obtained for storage time t=0, and the lowermost spectrum is obtained for the storage time of 8 h at 37° C. plus 22 h at 22° C. plus 108 h at 22° C. plus 6 h at 37° C.

Figure 14B:
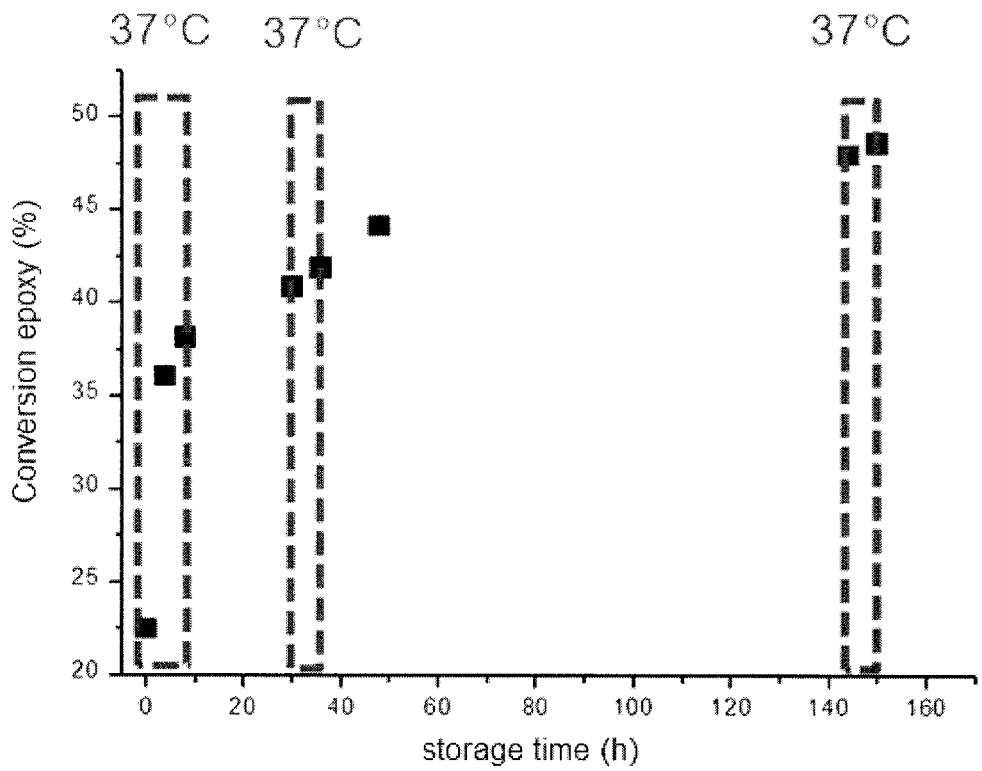

FIG. 14B shows epoxy function conversion versus storage time for the polymer obtained in FIG. 12 with heating periods of 37° C. within the storage times 0 to 10 h, 30 to 50 h and 143 to 150 h.

Figure 15:
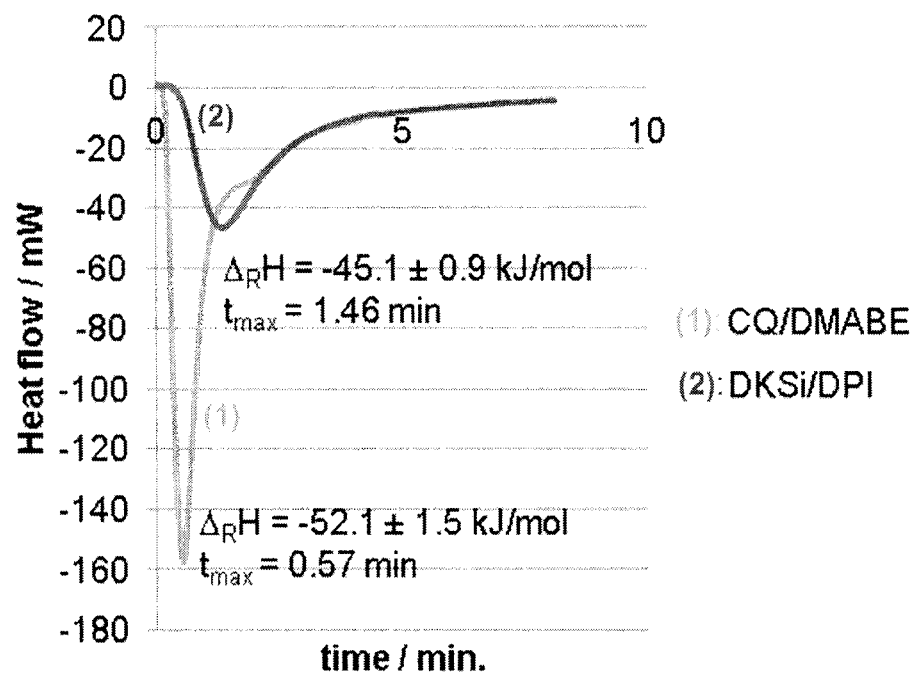

FIG. 15 shows a differential scanning calometry diagram of a UDMA/Glycerin dimethacrylate (GDM)/DEGVE photopolymerized in the presence of the initiator system DKSi/DPI (1.2 wt-%/1.2 wt-%) or CQ/DMABE (0.35%/0.49% w/w).

Figure 16:
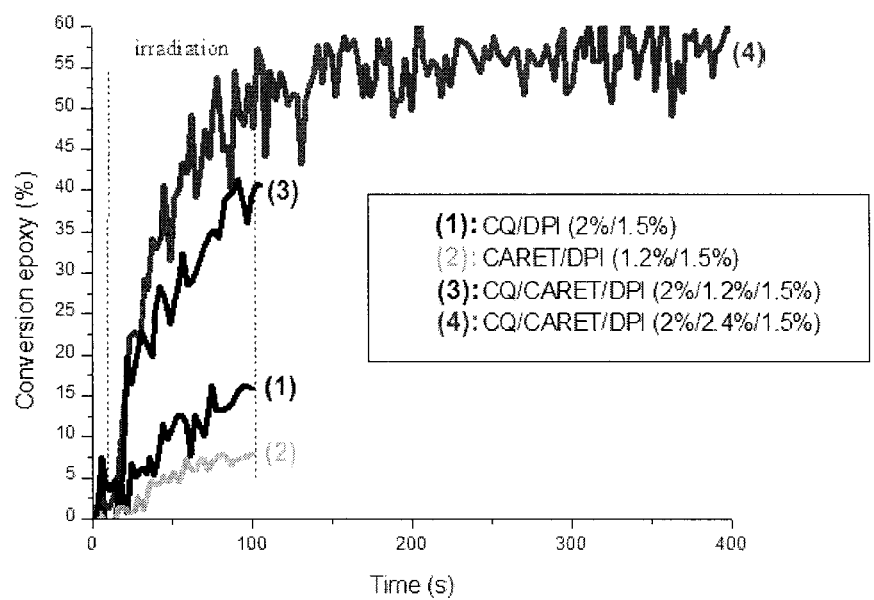

FIG. 16 shows photopolymerization profiles for the epoxy monomer EPOX polymerized in samples of 20 µm thickness under air in the presence of different initiator systems upon the exposure to dental LED at 477 nm (SmartLite® Focus; 300 mW/cm$^2$). Specifically, FIG. 16 shows separate curves for polymerisation in the presence of the following initiator systems:

curve (1): CQ/DPI (2%/1.5% w/w);
curve (2): CARET/DPI (1.2%/1.5% w/w);
curve (3): CQ/CARET/DPI (2%/1.2%/1.5% w/w), and
curve (4): CQ/CARET/DPI (2%/2.4%/1.5% w/w).

Figure 17A:
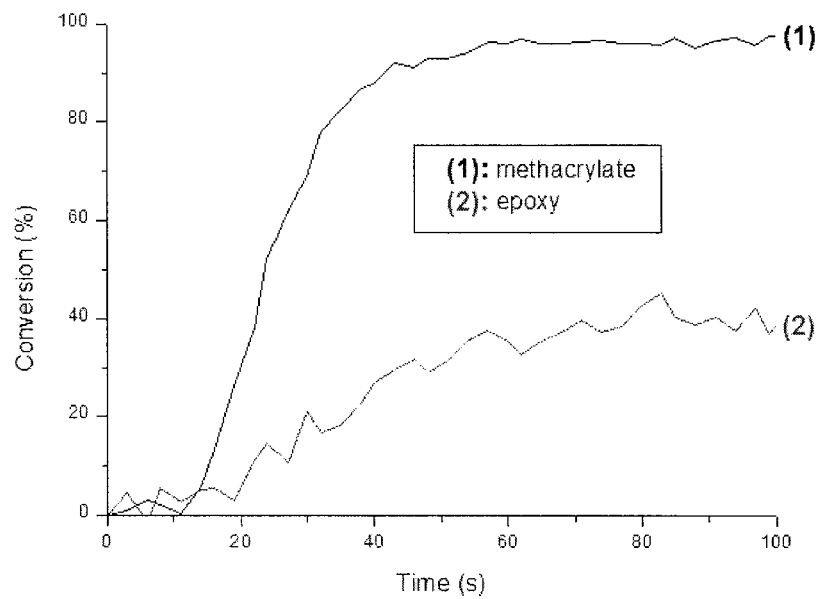

FIG. 17A shows photopolymerization profiles for a UDMA/EPOX-Si blend (50%/50% w/w) polymerized in samples of 1.4 mm thickness under air in the presence of the initiator system CQ/CARET/PI2074 (2%/2%/2% w/w) upon the exposure to dental LED at 477 nm (SmartLite® Focus; 300 mW/cm$^2$). Curve (1) is the conversion for the methacrylate functions, and curve (2) is the conversion for the epoxy functions during polymerization.

Figure 17B:
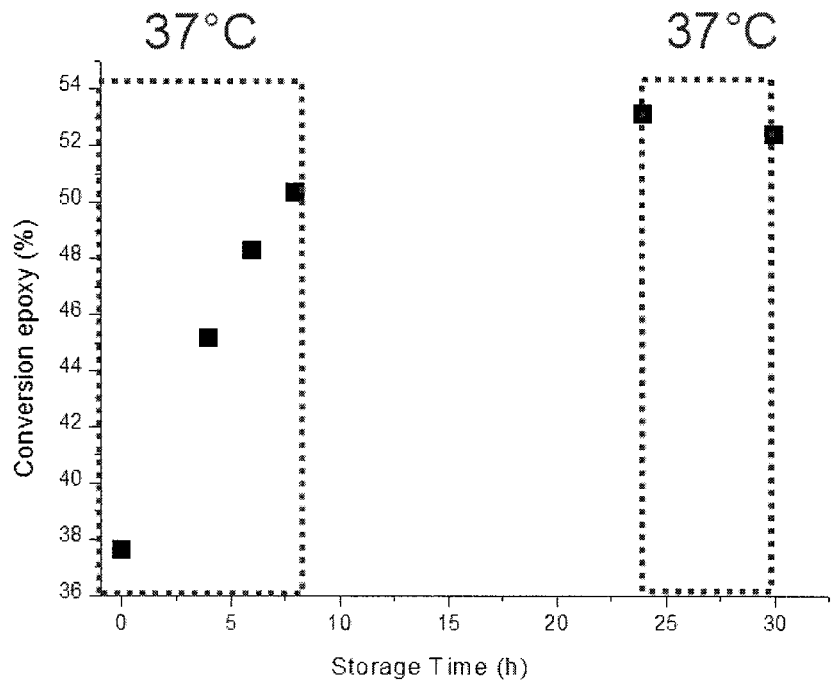

FIG. 17B shows epoxy function conversion versus storage time for the polymer obtained in FIG. 17A with heating periods of 37° C. within the storage times 0 to 7 h and 23 to 30 h.

Figure 18:
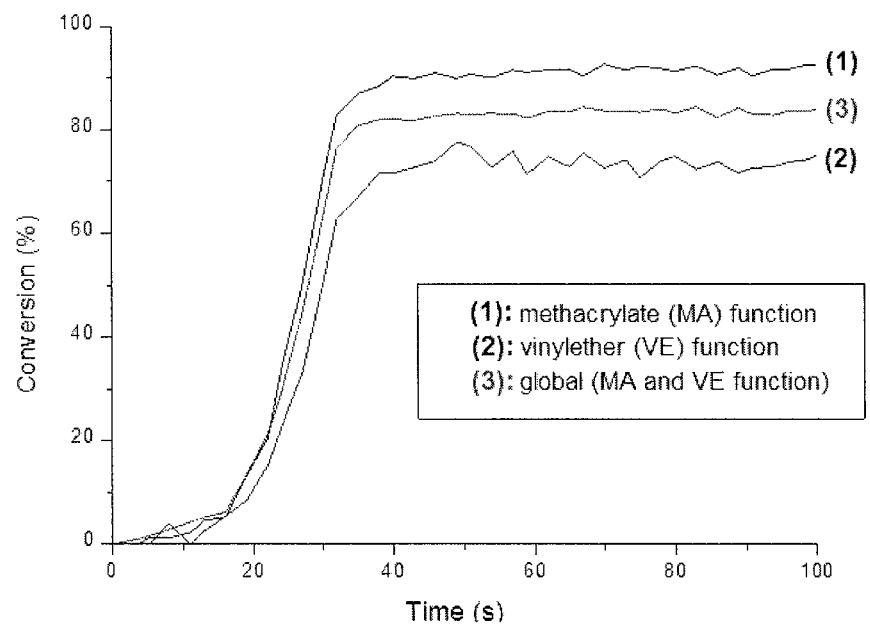

FIG. 18 shows photopolymerization profiles of the methacrylate functions (cf. curve (1)), the vinylether functions (cf. curve (2)), and of the global methacrylate and vinylether functions (cf. curve (3)) for an UDMA/VEEM (64%/36% w/w) blend polymerized in a sample of 1.4 mm thickness under air in the presence of the initiator system DKSi/PI2074/CARET (1.2%/1.1%/1% w/w) upon the exposure to dental LED at 477 nm (SmartLite® Focus, 300 mW/cm$^2$). The irradiation starts at t=10 s.

Figure 19:
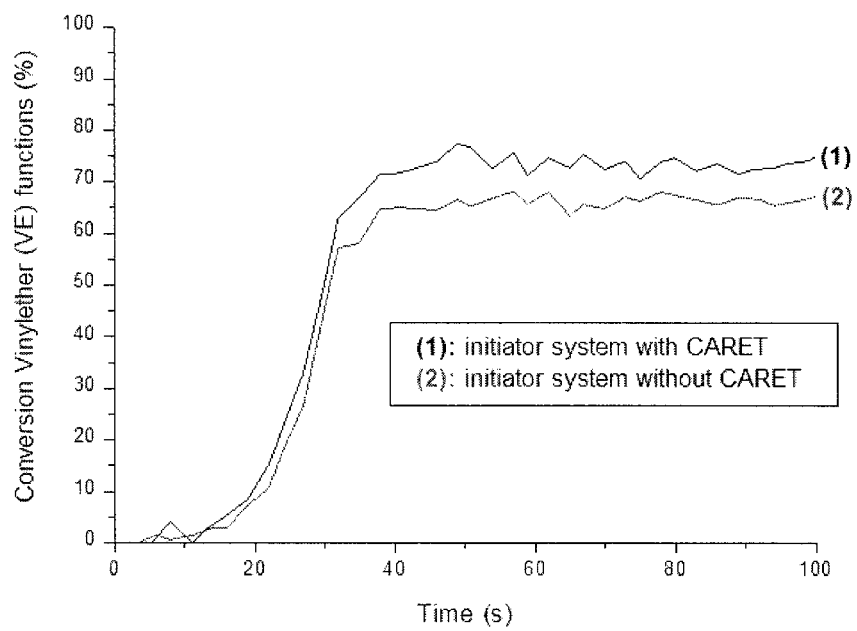

FIG. 19 shows photopolymerization profiles of the vinylether functions for a UDMA/VEEM (64%/36% w/w) blend polymerized in a sample of 1.4 mm thickness under air in the presence of the initiator system DKSi/PI2074/CARET (1.2%/1.1%/1% w/w) (cf. curve (1)) or DKSi/PI2074 (1.2%/1.1% w/w) upon the exposure to dental LED at 477 nm (SmartLite® Focus, 300 mW/cm$^2$). The irradiation starts at t=10 s.

Figure 20:
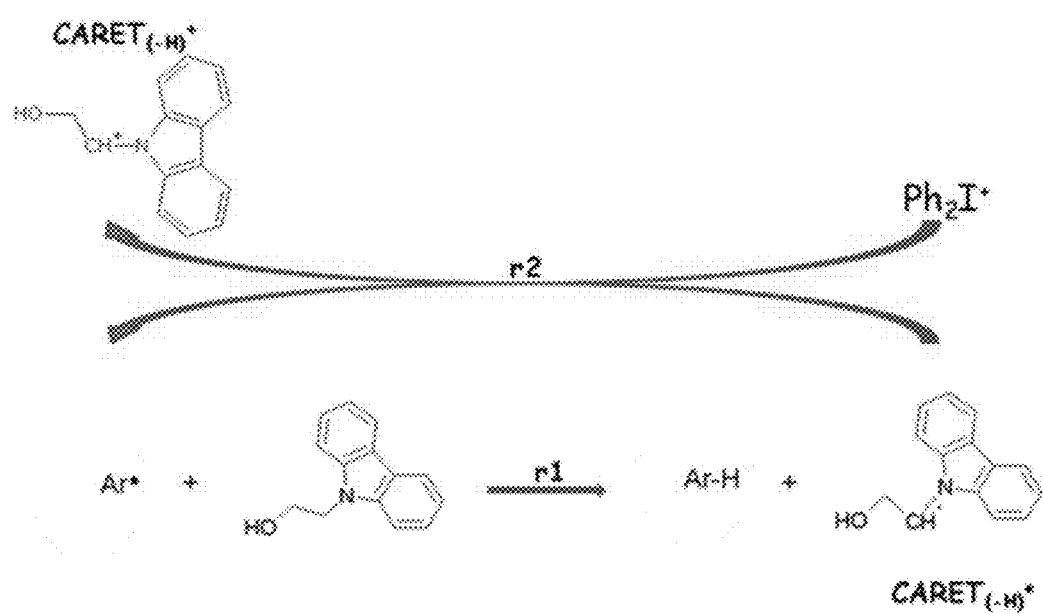

FIG. 20 shows proposed mechanism for the additive effect of CARET in cationic polymerization.

DETAILED DESCRIPTION OF PREFERRED EMBODIMENTS

The term "homogeneous phase" means that monomer combinations (i) and (ii), (i) and (iii), (ii) and (iii), or (i), (ii) and (iii), or monomer(s) (iii) are present in a single phase without detectable phase boundaries within the single phase.

The term "monomer(s)" as used herein means a compound having a polymerizable group.

The term "interpenetrating polymer network (IPN)" as used herein means that two or more polymers are at least partially interlaced on a molecular scale, but not covalently bonded to each other and cannot be separated unless chemical bonds are broken. A mixture of two or more pre-formed polymers does not represent an IPN. If the two or more polymers of the IPN are formed of compounds having two or more polymerizable groups, then the IPN is according to the official IUPAC definition: "a polymer comprising two or more networks which are at least partially interlaced on a molecular scale, but not covalently bonded to each other and cannot be separated unless chemical bonds are broken". If one or more polymer(s) is/are formed of a compound having two or more polymerizable groups, and one or more polymer(s) is/are formed of a compound having a single polymerizable group, then the IPN is, according to the IUPAC definition, a so-called "semi-interpentrating polymer network (SIPN): "a polymer comprising on or more networks and one or more linear or branched polymer(s) characterized by the penetration on a molecular scale of at least one of the networks by at least some of the linear of branched macromolecules". The present general definition of IPN includes the IPNs and SIPNs according to IUPAC definition, but also two or more linear or branchend polymers which are at least partially interlaced on a molecular scale, but not covalently bonded to each other, and which cannot be separated unless chemical bonds are broken.

The terms "polymerization" and "polymerizable" relates to the combining or the capability to combine by covalent bonding of a large number of smaller molecules, such as monomers, to form larger molecules, that is, macromolecules or polymers. The monomers may be combined to form only linear macromolecules or they may be combined to form three-dimensional macromolecules, commonly referred to as crosslinked polymers. For example, monofunctional monomers form linear polymers, whereas monomers having at least two functional groups form crosslinked polymers also known as networks. In case of a higher conversion rate of the polymerizable monomer, the amount of multifunctional monomers may be reduced or the leaching problem may be alleviated.

The terms "curing" and "photocuring" mean the polymerization of functional monomers, oligomers or even polymers, to a polymer network, specifically an IPN.

The terms "photocurable" and "curable" refer to a dental composition that will polymerize into a polymer network when irradiated for example with actinic radiation such as ultraviolet (UV), visible, or infrared radiation.

The term "quantum yield" is used herein to indicate the efficiency of a photochemical process. More particularly, quantum yield is a measure of the probability of the excitation of a particular molecule after absorption of a light quantum. The term expresses the number of photochemical events per photon absorbed.

"Actinic radiation" is any electromagnetic radiation that is capable of producing photochemical action and can have a wavelength of at least 150 nm and up to and including 1250 nm, and typically at least 300 nm and up to and including 750 nm.

The term "coinitiator" refers to a molecule that produces a chemical change in another molecule such as an initiator of formulae (I) to (IV). The coinitiator may be for example be selected from the group consisting of a compound having a Si—H or Ge—H bond, an electron donor, a carbazole compound, and a photoinitiator other than any one of compound of formula (I) to (IV).

The term "electron donor" as used herein means a compound capable of contributing electrons in a photochemical process. Suitable examples include organic compounds having heteroatoms with electron lone pairs, for example amine compounds.

The present invention relates to a dental composition. The dental composition may be a dental restorative or dental prosthetic composition. More preferably, the dental composition is selected from the group consisting of a dental adhesive composition, a bonding agent, a pit and fissure sealant, a dental desensitizing composition, a pulp capping composition, a dental composite, a flowable dental composite, a dental glass ionomer cement, a dental cement, resin modified glass ionomers, or a dental root canal sealer composition. The dental composition may be cured by irradiation of actinic radiation.

The Homogeneous Phase (a)

The dental composition comprises (a) a homogeneous phase comprising monomer combinations (i) and (ii), (i) and (iii), (ii) and (iii), or (i), (ii) and (iii), or comprising monomer (iii), wherein
(i) represents one or more compounds having one or more radically polymerizable carbon-carbon double bonds;
(ii) represents one or more compounds having one or more cationically polymerizable groups;
(iii) represents one or more compounds having a combination of one or more radically polymerizable carbon-carbon double bonds and one or more cationically polymerizable groups.

The radically polymerizable carbon-carbon double bonds and cationically polymerizable groups are not particularly limited. Preferably, radically polymerizable carbon-carbon double bonds are selected from carbon-carbon double bonds of (meth)acryloyl group(s) and a (meth)acrylamide group, preferably (meth)acryloyl group(s). Further, it is preferred that the cationically polymerizable groups are selected from epoxide groups, oxetane groups, vinyl ether groups, aziridine groups, and azetidine groups, preferably from epoxide groups, vinyl ether groups and oxetane groups, most preferably from epoxide groups and vinyl ether groups.

The compound(s) (i) having one or more radically polymerizable carbon-carbon double bonds are not particularly limited. However, preferably, their radically polymerizable carbon-carbon double bonds are selected from carbon-carbon double bonds of a (meth)acryloyl group and a (meth)acrylamide group.

Suitable examples of compounds (i) may be selected from the group consisting of (meth)acrylates, amides of acrylic or methacrylic acid, urethane acrylates or methacrylates, and polyol acrylates or methacrylates.

(Meth)acrylates may be preferably selected from compounds of the following formulae (A), (B) and (C):

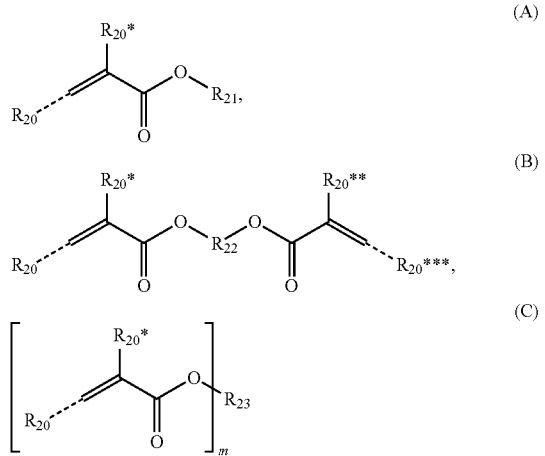

wherein $R_{20}$, $R^*_{20}$, $R^{}_{20}$, $R^{*}_{20}$ independently represent a hydrogen atom, —COOM, a linear $C_{1-18}$ or branched $C_{3-18}$ alkyl group which may be substituted by a $C_{3-6}$ cycloalkyl group, a $C_{6-14}$ aryl or $C_{3-14}$ heteroaryl group, —COOM, —$PO_3M$, —O—$PO_3M_2$ or —$SO_3M^*$, a $C_3$ to $C_{18}$ cycloalkyl group which may be substituted by a $C_{1-16}$ alkyl group, a $C_{6-14}$ aryl or $C_{3-14}$ heteroaryl group, or a $C_5$ to $C_{18}$ aryl or $C_3$ to $C_{18}$ heteroaryl group, —COOM, —$PO_3M$, —O—$PO_3M_2$ or —$SO_3M^*$, $R_{21}$ represents a hydrogen atom, a linear $C_{18}$ or branched $C_{3-18}$ alkyl group or $C_2$ to $C_{18}$ alkenyl group which may be substituted by a $C_{3-6}$ cycloalkyl group, a $C_{6-14}$ aryl or $C_{3-14}$ heteroaryl group, —COOM, —$PO_3M$, —O—$PO_3M_2$ or —$SO_3M^*$, a $C_3$ to $C_{18}$ cycloalkyl group which may be substituted by a $C_{1-16}$ alkyl group, a $C_{6-14}$ aryl or $C_{3-14}$ heteroaryl group, —COOM, —$PO_3M$, —O—$PO_3M_2$ or —$SO_3M^*$, or a $C_5$ to $C_{18}$ aryl or $C_3$ to $C_{18}$ heteroaryl group, $R_{22}$ represents a divalent organic residue having from 1 to 45 carbon atoms, whereby the divalent organic residue may contain at least one of from 1 to 7 $C_{3-12}$ cycloalkylene group(s), 1 to 7 $C_{6-14}$ arylene groups, 1 to 7 carbonyl groups, 1 to 7 carboxyl groups (—(C=O)—O— or —O—(C=O)—), 1 to 7 amide groups (—(C=O)—NH— or —NH—(C=O)—) or 1 to 7 urethane groups (—NH—(C=O)—O— or —O—(C=O)—NH—), and 1 to 14 heteroatoms selected from oxygen, nitrogen and sulphur, which divalent organic residue may be substituted with one or more substituents selected from the group consisting of a hydroxyl group, a thiol group, a $C_{6-14}$ aryl group, —COOM, —$PO_3M$, —O—$PO_3M_2$ or —$SO_3M^*$; preferably $R_{22}$ is a $C_1$ to $C_{18}$ alkylene group which may be substituted by one or more —OH group(s), which alkylene group may contain at least one of 1 to 4 $C_{6-10}$ arylene groups, 1 to 4 urethane groups (—NH—(C=O)—O— or —O—(C=O)—NH—), and 1 to 8 oxygen atoms;

$R_{23}$ represents a saturated di- or multivalent substituted or unsubstituted $C_2$ to $C_{18}$ hydrocarbon group, a saturated di- or multivalent substituted or unsubstituted cyclic $C_3$ to $C_{18}$ hydrocarbon group, a di- or multivalent substituted or unsubstituted $C_4$ to $C_{18}$ aryl or heteroaryl group, a di- or multivalent substituted or unsubstituted $C_5$ to $C_{18}$ alkylaryl or alkylheteroaryl group, a di- or multivalent substituted or unsubstituted $C_7$ to $C_{30}$ aralkyl group, or a di- or multivalent substituted or unsubstituted $C_2$ to $C_{45}$ mono-, di-, or polyether residue having from 1 to 14 oxygen atoms, and m is an integer, preferably in the range from 1 to 10, wherein M of any one of $R_{20}$, $R^*_{20}$, $R^{}_{20}$, $R^{*}_{20}$, $R_{21}$, and $R_{22}$, which M are independent from each other, each represent a hydrogen atom or a metal atom, and M* of any one of $R_{20}$, $R^*_{20}$, $R^{}_{20}$, $R^{*}_{20}$, $R_{21}$, and $R_{22}$, which M are independent from each other, each represent a metal atom.

For $R_{20}$, $R^*_{20}$, $R^{}_{20}$ and $R^{*}_{20}$, the linear $C_{1-18}$ or branched $C_{3-18}$ alkyl group may e.g. be methyl, ethyl, n-propyl, i-propyl, n-butyl, isobutyl, tert-butyl, sec-butyl, pentyl or hexyl. For $R_{21}$ and $R^*_{21}$, the CG-18 alkyl group or $C_{2-18}$ alkenyl group may e.g. be eth(en)yl, n-prop(en)yl, i-prop(en)yl, n-but(en)yl, isobut(en)yl, tert-but(en)yl sec-but(en)yl, pent(en)yl or hex(en)yl.

For $R_{20}$, $R^*_{20}$, $R^{}_{20}$, $R^{*}_{20}$ and $R_{21}$ an aryl group may, for example, be a phenyl group or a naphthyl group, and a $C_{3-14}$ heteroaryl group may contain 1 to 3 heteroatoms selected from nitrogen, oxygen and sulfur.

For $R_{22}$, in the phrase "divalent organic residue may contain at least one of . . ." means that the groups which may be contained in the divalent organic residue are incorporated in the divalent organic residue by means of covalent bonding. For example, in BisGMA, two aryl groups in the form of phenyl and two heteroatoms in the form of oxygen are incorporated into the divalent organic residue of $R_{22}$. Or, as a further example, in UDMA, two urethane groups (—NH—(C=O)—O— or —O—(C=O)—NH—) are incorporated in the divalent organic residue of $R_{22}$.

In formula (B), the dotted bond indicates that $R_{20}$ and $R^{***}_{20}$ may be in cis or trans configuration relative to CO.

Preferably, in formulae (A), (B) and (C), $R_{20}$, $R^{*}_{20}$, $R^{}_{20}$ and $R^{*}_{20}$ independently represent a hydrogen atom, a linear $C_{1-16}$ or branched $C_{3-16}$ alkyl group which may be substituted by a $C_{3-6}$ cycloalkyl group, a $C_{6-14}$ aryl or $C_{3-14}$ heteroaryl group, a $C_{3-6}$ cycloalkyl group which may be substituted by a $C_{1-16}$ alkyl group, a $C_{6-14}$ aryl or $C_{3-14}$ heteroaryl group, a $C_{6-14}$ aryl or $C_{3-14}$ heteroaryl group. More preferably, in formula (B), $R_{20}$, $R^{*}_{20}$, $R^{}_{20}$ and $R^{*}_{20}$ independently represent a hydrogen atom, a linear $C_{1-8}$ or branched $C_{3-8}$ alkyl group which may be substituted by a $C_{4-6}$ cycloalkyl group, a $C_{6-10}$ aryl or $C_{4-10}$ heteroaryl group, a $C_{4-6}$ cycloalkyl group which may be substituted by a $C_{1-6}$ alkyl group, a $C_{6-10}$ aryl or $C_{4-10}$ heteroaryl group or a $C_{6-10}$ aryl group. Even more preferably, $R_{20}$, $R^{*}_{20}$, $R^{}_{20}$ and $R^{*}_{20}$ independently represent a hydrogen atom, a linear $C_{1-4}$ or branched $C_3$ or $C_4$ alkyl group which may be substituted by a cyclohexyl group or a phenyl group, or a cyclohexyl group which may be substituted by a $C_{1-4}$ alkyl group. Most preferably, $R_{20}$, $R^{*}_{20}$, $R^{}_{20}$ and $R^{*}_{20}$ independently represent a hydrogen atom or a linear $C_{1-4}$ or branched $C_3$ or $C_4$ alkyl group.

Preferably, in formula (A), $R_{21}$ represents a hydrogen atom, a linear $C_{1-16}$ or branched $C_{3-16}$ alkyl group or $C_{2-16}$ alkenyl group which may be substituted by a $C_{3-6}$ cycloalkyl group, a $C_{6-14}$ aryl or $C_{3-14}$ heteroaryl group, a $C_{3-6}$ cycloalkyl group which may be substituted by a $C_{1-16}$ alkyl group, a $C_{6-14}$ aryl or $C_{3-14}$ heteroaryl group, a $C_{6-14}$ aryl or $C_{3-14}$ heteroaryl group. More preferably, $R_{21}$ represents a hydrogen atom, a linear $C_{1-10}$ or branched $C_{3-10}$ alkyl or $C_{2-10}$ alkenyl group which may be substituted by a $C_{4-6}$ cycloalkyl group, a $C_{6-10}$ aryl or $C_{4-10}$ heteroaryl group, a $C_{4-6}$ cycloalkyl group which may be substituted by a $C_{1-6}$ alkyl group, a $C_{6-10}$ aryl or $C_{4-10}$ heteroaryl group or a $C_{6-10}$ aryl group. Even more preferably, $R_{21}$ represents is a hydrogen atom, a linear $C_{1-10}$ or branched $C_{3-10}$ alkyl group or linear $C_{2-10}$ or branched $C_{3-10}$ alkenyl group which may be substituted by a cyclohexyl group or a phenyl group, or a cyclohexyl group which may be substituted by a $C_{1-4}$ alkyl group. Yet even more preferably, $R_{21}$ represents an unsubstituted $C_{1-10}$ alkyl group or $C_{2-10}$ alkenyl group, still even more preferably an unsubstituted $C_{2-6}$ alkyl group or $C_{3-6}$ alkenyl group, and most preferably an ethyl group or an allyl group.

The (meth)acrylate compounds of formulae (A), (B) and (C) may be selected from the group consisting of methyl acrylate, methyl methacrylate, ethyl acrylate, ethyl methacrylate, propyl acrylate, propyl methacrylate, isopropyl acrylate, isopropyl methacrylate, 2-hydroxyethyl acrylate, 2-hydroxyethyl methacrylate (HEMA), hydroxypropyl acrylate, hydroxypropyl methacrylate, tetrahydrofurfuryl acrylate, tetrahydrofurfuryl methacrylate, glycidyl acrylate, glycidyl methacrylate, bisphenol A glycerolate dimethacrylat ("bis-GMA", CAS-No. 1565-94-2), 4,4,6,16 (or 4,6,6,16)-tetramethyl-10,15-dioxo-11,14-dioxa-2,9-diazaheptadec-16-enoicacid 2-[(2-methyl-1-oxo-2-propen-1-yl)oxy]ethyl ester (CAS no. 72869-86-4) (UDMA), glycerol mono- and di-acrylate such as 1,3-glycerol dimethacrylate (GDM), glycerol mono- and dimethacrylate, ethyleneglycol diacrylate, ethyleneglycol dimethacrylate, polyethyleneglycol diacrylate (where the number of repeating ethylene oxide units vary from 2 to 30), polyethyleneglycol dimethacrylate (where the number of repeating ethylene oxide units vary from 2 to 30 especially triethylene glycol dimethacrylate ("TEGDMA"), neopentyl glycol diacrylate, neopentylglycol dimethacrylate, trimethylolpropane triacrylate, trimethylol propane trimethacrylate, mono-, di-, tri-, and tetra-acrylates and methacrylates of pentaerythritol and dipentaerythritol, 1,3-butanediol diacrylate, 1,3-butanediol dimethacrylate, 1,4-butanedioldiacrylate, 1,4-butanediol dimethacrylate, 1,6-hexane diol diacrylate, 1,6-hexanediol dimethacrylate, di-2-methacryloyloxethyl hexamethylene dicarbamate, di-2-methacryloyloxyethyl trimethylhexanethylene dicarbamate, di-2-methacryloyl oxyethyl dimethylbenzene dicarbamate, methylene-bis-2-methacryloxyethyl-4-cyclohexyl carbamate, di-2-methacryloxyethyl-dimethylcyclohexane dicarbamate, methylene-bis-2-methacryloxyethyl-4-cyclohexyl carbamate, di-1-methyl-2-methacryloxyethyl-trimethylhexamethylene dicarbamate, di-1-methyl-2-methacryloxyethyl-dimethylbenzene dicarbamate, di-1-methyl-2-methacryloxyethyl-dimethylcyclohexane dicarbamate, methylene-bis-1-methyl-2-methacryloxyethyl-4-cyclohexyl carbamate, di-1-chloromethyl-2-methacryloxyethyl-hexamethylene dicarbamate, di-1-chloromethyl-2-methacryloxyethyl-trimethylhexamethylene dicarbamate, di-1-chloromethyl-2-methacryloxyethyl-dimethylbenzene dicarbamate, di-1-chloromethyl-2-methacryloxyethyl-dimethylcyclohexane dicarbamate, methylene-bis-2-methacryloxyethyl-4-cyclohexyl carbamate, di-1-methyl-2-methacryloxyethyl-hexamethylene dicarbamate, di-1-methyl-2-methacryloxyethyl-trimethylhexamethylene dicarbamate, di-1-methyl-2-methacryloxyethyl-dimethylbenzene dicarbamate, di-1-methyl-2-metha-cryloxyethyl-dimethylcyclohexane dicarbamate, methylene-bis-1-methyl-2-methacryloxyethyl-4-cyclohexyl carbamate, di-1-chloromethyl-2-methacryloxyethyl-hexamethylene dicarbamate, di-1-chloromethyl-2-methacryloxyethyl-trimethylhexamethylene dicarbamate, di-1-chloromethyl-2-methacryloxyethyl-dimethylbenzene dicarbamate, di-1-chloromethyl-2-methacryloxyethyl-dimethylcyclohexane dicarbamate, methylene-bis-1-chloromethyl-2-methacryloxyethyl4-cyclohexyl carbamate, 2,2'-bis(4-methacryloxyphenyl)propane, 2,2'bis(4-acryloxyphenyl) propane, 2,2'-bis[4(2-hydroxy-3-methacryloxy-phenyl)] propane, 2,2'-bis[4(2-hydroxy-3-acryloxy-phenyl)propane, 2,2'-bis(4-methacryloxyethoxyphenyl)propane, 2,2'-bis(4-acryloxyethoxyphenyl)propane, 2,2'-bis(4-methacryloxypropoxyphenyl)propane, 2,2'-bis(4-acryloxypropoxyphenyl)propane, 2,2'-bis(4-methacryloxydiethoxyphenyl) propane, 2,2'-bis(4-acryloxydiethoxyphenyl)propane, 2,2'-bis[3(4-phenoxy)-2-hydroxypropane-1-methacrylate] propane, and 2,2'-bis[3(4-phenoxy)-2-hydroxypropane-1-acrylate]propane.

Most preferably, a compound of formula (B) is selected from the group consisting of:

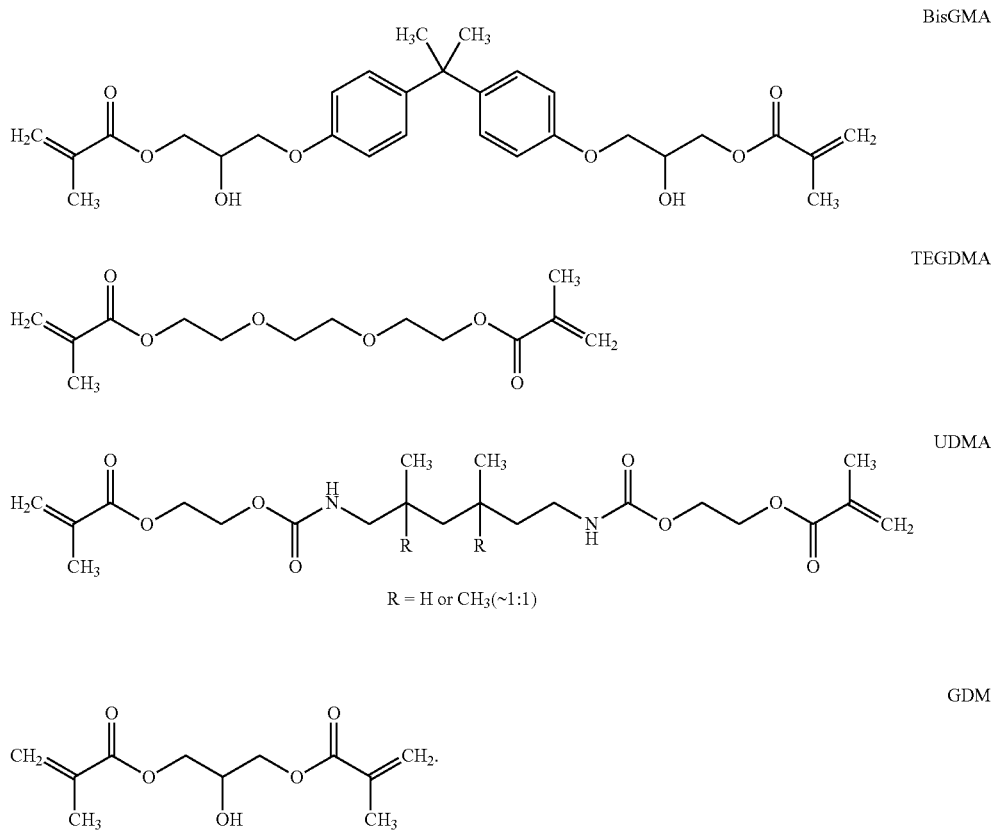

BisGMA

TEGDMA

UDMA

R = H or CH$_3$(~1:1)

GDM

Particular preferred mono- or bis- or (meth)acrylamides and poly[(meth) acrylamides] have the following formulae (D), (E) and (F):

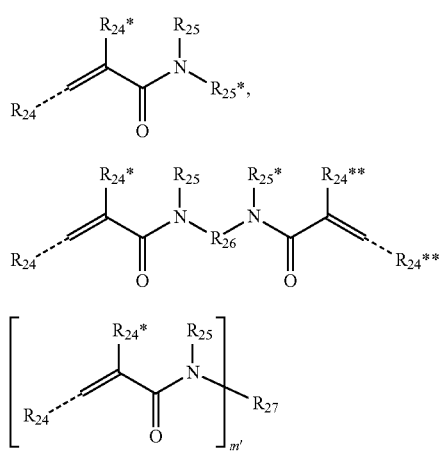

wherein $R_{24}R^*_{24}$, $R^{}_{24}$, $R^{*}_{24}$ have the same meaning as $R_{20}R^*_{20}$, $R^{}_{20}$, $R^{*}_{20}$ defined above for formulae (A), (B) and (C), $R_{25}$, $R^*_{25}$ independently represent a residue having the same meaning as $R_{21}$ defined above for formula (A), and $R_{27}$ and m' have the same meaning as $R_{23}$ and m defined above for formula (C).

In formula (E), $R_{26}$ represents a divalent substituted or unsubstituted organic residue having from 1 to 45 carbon atoms, whereby said organic residue may contain at least one of 1 to 7 $C_{3-12}$ cycloalkylene group(s), 1 to 7 $C_{6-14}$ arylene groups, from 1 to 7 carbonyl groups, 1 to 7 carboxyl groups (—(C=O)—O— or —O—(C=O)—), 1 to 7 amide groups (—(C=O)—NH— or —NH—(C=O)—), 1 to 7 urethane groups (—NH—(C=O)—O— or —O—(C=O)—NH—), and 1 to 14 heteroatoms selected from oxygen, nitrogen and sulphur, which divalent organic residue may be substituted with one or more substituent(s) selected from the group consisting of a hydroxyl group, a thiol group, a $C_{6-14}$ aryl group, —COOM, —PO$_3$M, —O—PO$_3$M$_2$ or —SO$_3$M*; preferably $R_{26}$ is a $C_1$ to $C_{18}$ alkylene group or a $C_2$ to $C_{18}$ alkenylene group which may contain at least one of 1 to 4 $C_{6-10}$ arylene groups and $C_{3-8}$ cycloalkylene group, 1 to 4 urethane groups (—NH—(C=O)—O— or —O—(C=O)—NH—), and 1 to 8 oxygen atoms or nitrogen atoms.

For $R_{26}$, the phrase "divalent organic residue may contain at least one of . . . " has an analogous meaning as defined above for $R_{22}$ of compound of formula (B).

In formulae (D), (E), (F), the dotted bond indicates that $R_{24}$ and $R^{***}_{24}$ may be in cis or trans configuration relative to CO.

In compound of formula (D), $R_{25}$ and $R_{25}^*$ may cooperatively form a ring in which $R_{25}$ and $R_{25}^*$ are linked by a C—C bond or a functional group selected from the group consisting of an ether group, a thioether group, an amine group and an amide group.

Preferred methacrylamides according to formulae (D), (E), (F) have the following formulae:

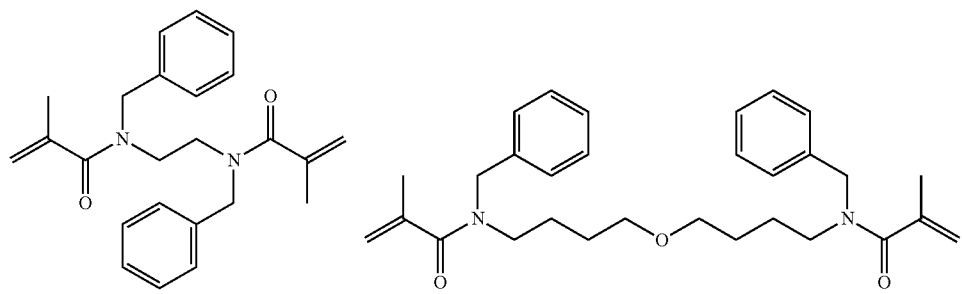
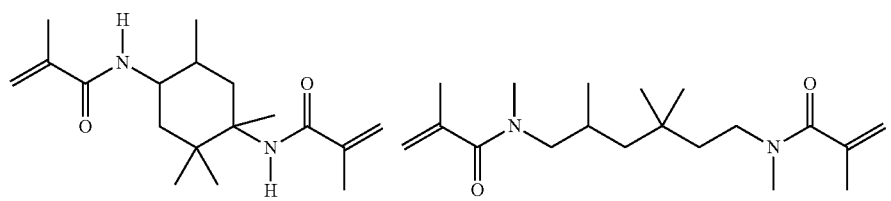
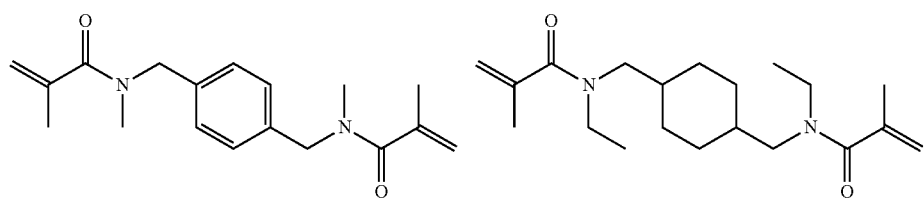
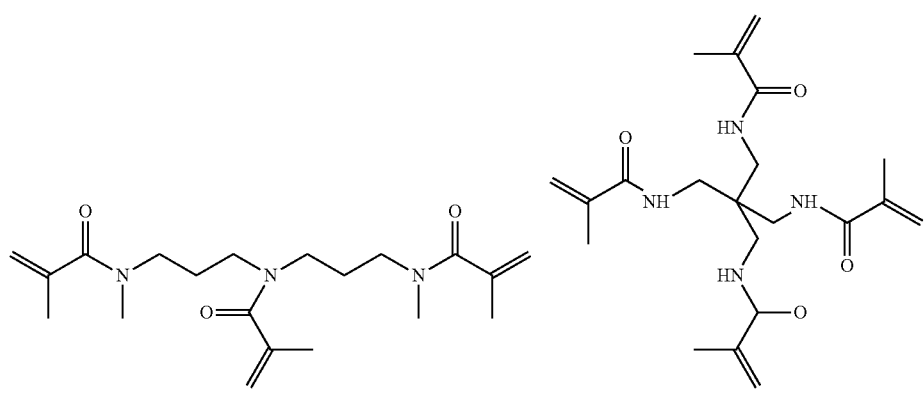
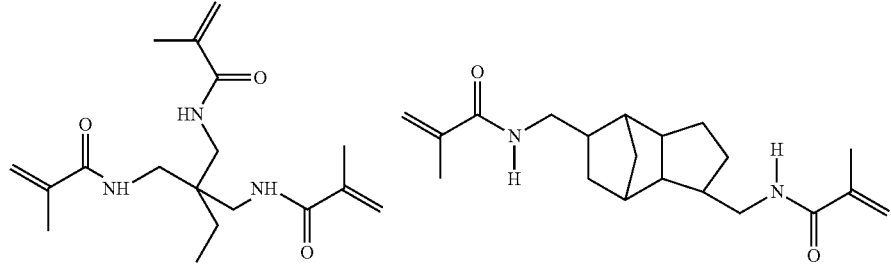
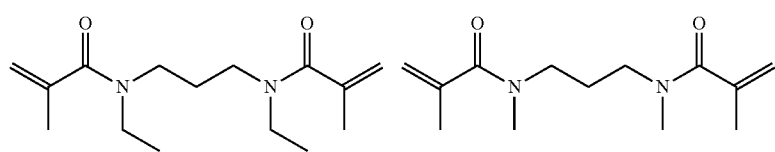

-continued
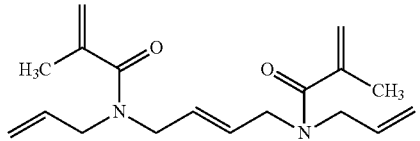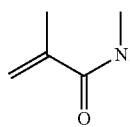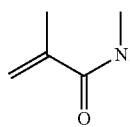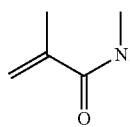
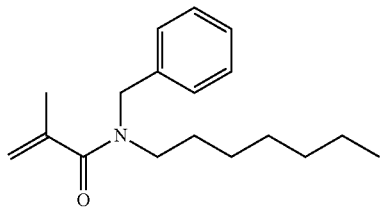
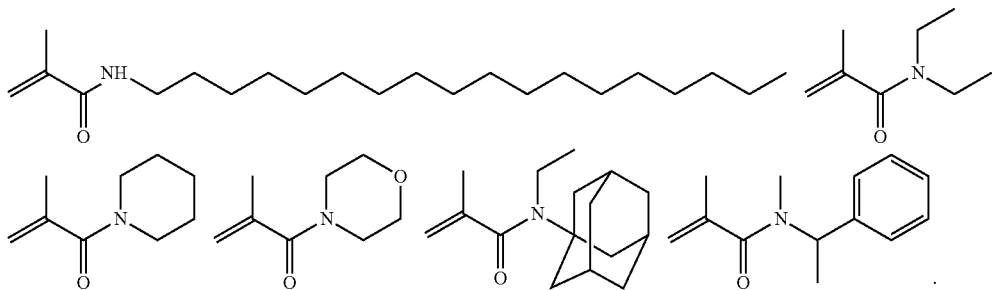
Preferred acrylamides according to formulae (D), (E), (F) have the following formulae:
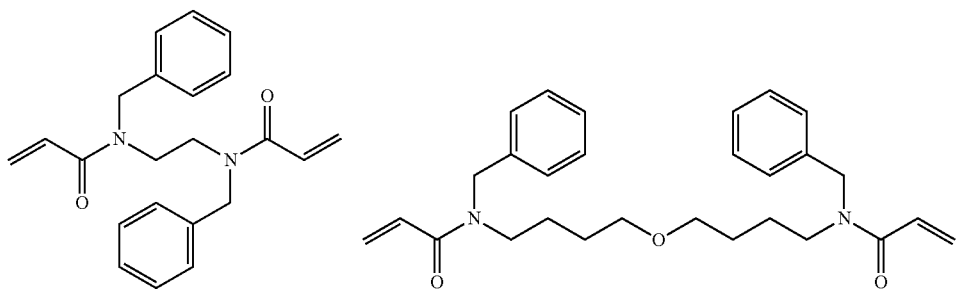
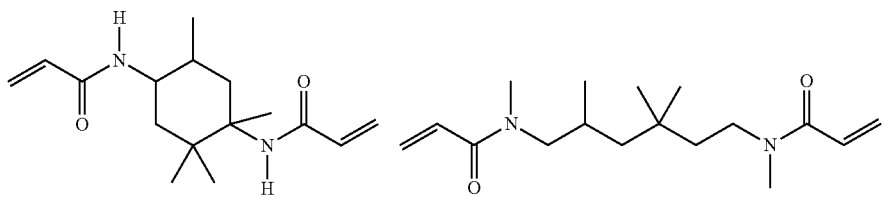
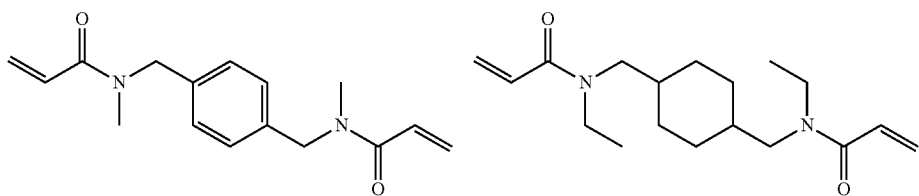

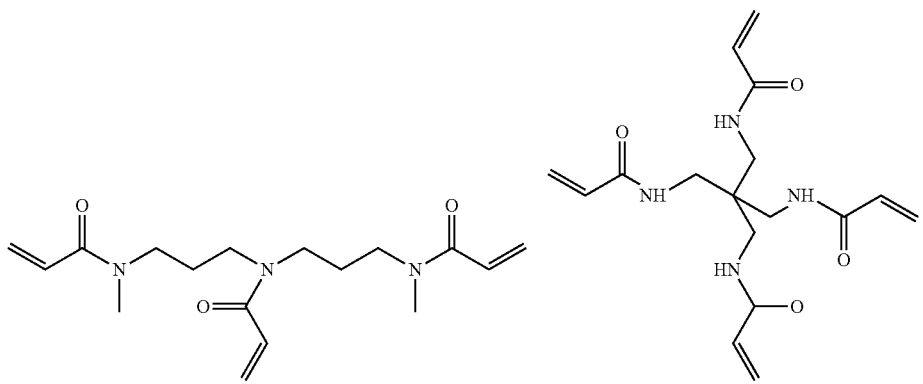
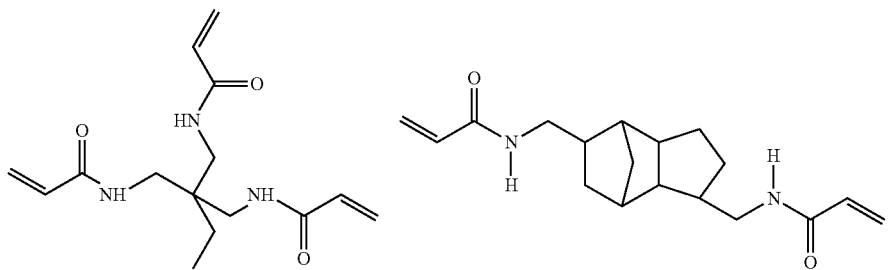
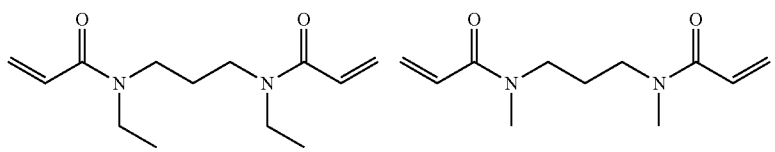
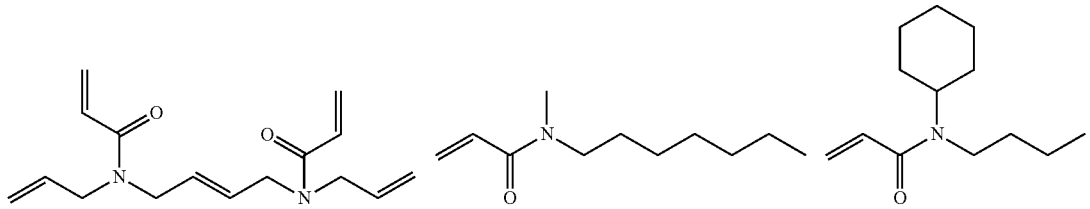
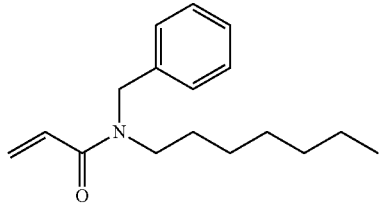
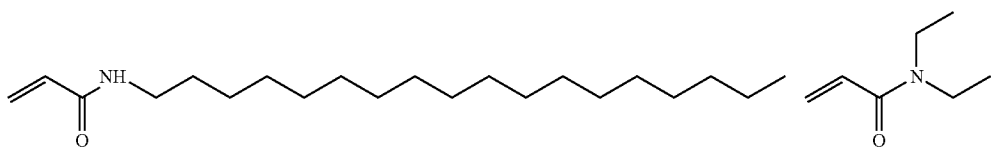
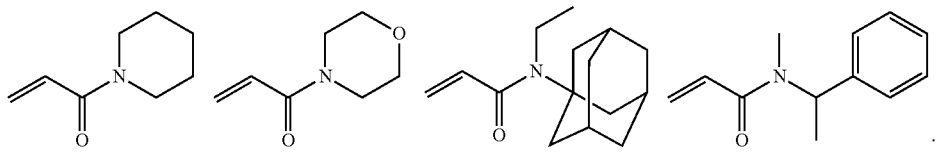

Most preferred are the bis-(meth)acrylamides:
N,N'-diallyl-1,4-bisacrylamido-(2E)-but-2-en (BAABE) having the structural formula

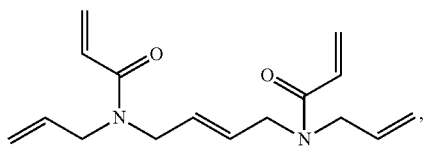 [SMILES: C=CCN(C/C=C/CN(CC=C)C(=O)C=C)C(=O)C=C]

and
N,N'-diethyl-1,3-bisacrylamido-propan (BADEP) having the structural formula

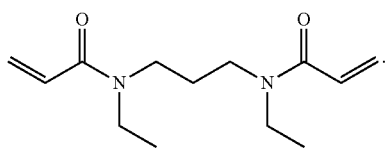 [SMILES: C=CC(=O)N(CC)CCCN(CC)C(=O)C=C]

Compounds having a (meth)acryloyl group or a (meth)acrylamide group also preferably be selected from phosphoric acid ester group containing polymerizable compounds having at least one polymerizable double bond preferably have the following formula (G):

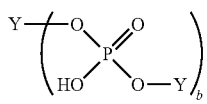

(G)

wherein
the moieties Y independent from each other represent a hydrogen atom or
a moiety of the following formulae (Y*), (Y) or (Y*):

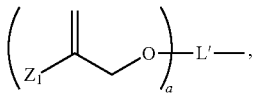

(Y*)

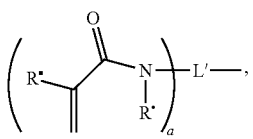

(Y**)

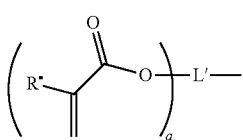

(Y***)

wherein
$Z_1$ is $COOR^\alpha$, $COSR^\beta$, $CON(R^\alpha)_2$, $CONR^\alpha R^\beta$, or $CONHR^\alpha$, wherein $R^\alpha$ and $R^\beta$ independently represent a hydrogen atom, a $C_{1-18}$ alkyl group optionally substituted by a $C_{3-8}$ cycloalkyl group, an optionally substituted $C_{3-8}$ cycloalkyl group, an optionally substituted $C_{4-18}$ aryl or heteroaryl group, an optionally substituted $C_{5-18}$ alkylaryl or alkylheteroaryl group, or an optionally substituted $C_{7-30}$ aralkyl group, whereby two $R^{13}$ residues may form together with the adjacent nitrogen atom to which they are bound a 5- to 7-membered heterocyclic ring which may contain further nitrogen atoms or an oxygen atoms, and whereby the optionally substituted groups may be substituted by 1 to 5 $C_{1-5}$ alkyl group(s);

$R^\blacksquare$ and $R^\bullet$ independently represent a hydrogen atom, an optionally substituted $C_{1-18}$ alkyl group, an optionally substituted $C_{3-18}$ cycloalkyl group, an optionally substituted $C_{5-18}$ aryl or heteroaryl group, an optionally substituted $C_{5-18}$ alkylaryl or alkylheteroaryl group, an optionally substituted $C_{7-30}$ aralkyl group, whereby the optionally substituted groups may be substituted by 1 to 5 $C_{1-5}$ alkyl group(s);

L* represents an (a+b)-valent organic residue (whereby b is 1 when Y in formula (D) is within the round brackets) containing 2 to 45 carbon atoms and optionally heteroatoms such as oxygen, nitrogen and sulfur atoms, the carbon atoms including a+b carbon atoms selected from primary and secondary aliphatic carbon atoms, secondary alicyclic carbon atoms, and aromatic carbon atoms, each of the a+b carbon atoms linking a phosphate or a moiety of any one of formula (Y*), (Y) and (Y*); a is an integer of from 1 to 10, preferably 1 to 5; b is an integer of from 1 to 10, preferably 1 to 5; provided that at least one Y is not hydrogen. The preparation of such compounds wherein Y=Y* is known from EP 1 548 021 A1.

Furthermore, compounds having a (meth)acryloyl group or a (meth)acrylamide group may also be selected from phosphonic acid group containing polymerizable acidic compounds of the following formula (H):

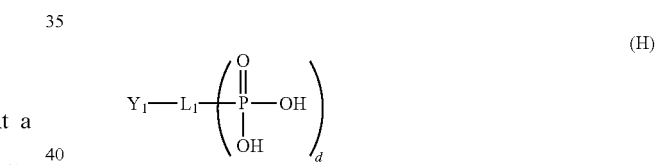

(H)

wherein
the moiety $Y_1$ represents a moiety of the following formulae $(Y_1^{})$ or $(Y_1^{*})$:

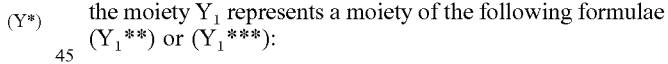

$(Y_1^*)$

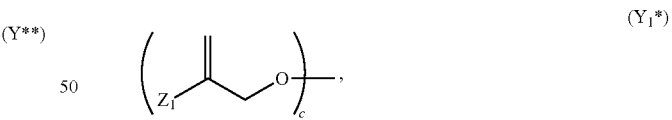

$(Y_1^{**})$

$(Y_1^{***})$ $Z_2$ independently has the same meaning as defined for $Z_1$;
$R^\square$ and $R^\circ$ independently have the same meaning as defined for $R^\blacksquare$ and $R^\bullet$;

$L_1$ represents a (c+d) valent organic residue containing 2 to 45 carbon atoms and optionally heteroatoms such as oxygen, nitrogen and sulfur, the carbon atoms including c+d carbon atoms selected from primary and secondary aliphatic carbon atoms, secondary alicyclic carbon atoms, and aromatic carbon atoms, each of the c+d carbon atoms linking a phosphonate or a moiety of any one of formula $(Y_1^*)$, $(Y_1^{})$ and $(Y_1^{*})$; and c and d independently represent integers of from 1 to 10.

From compound of formula (G'), the following formulae are particularly preferred:

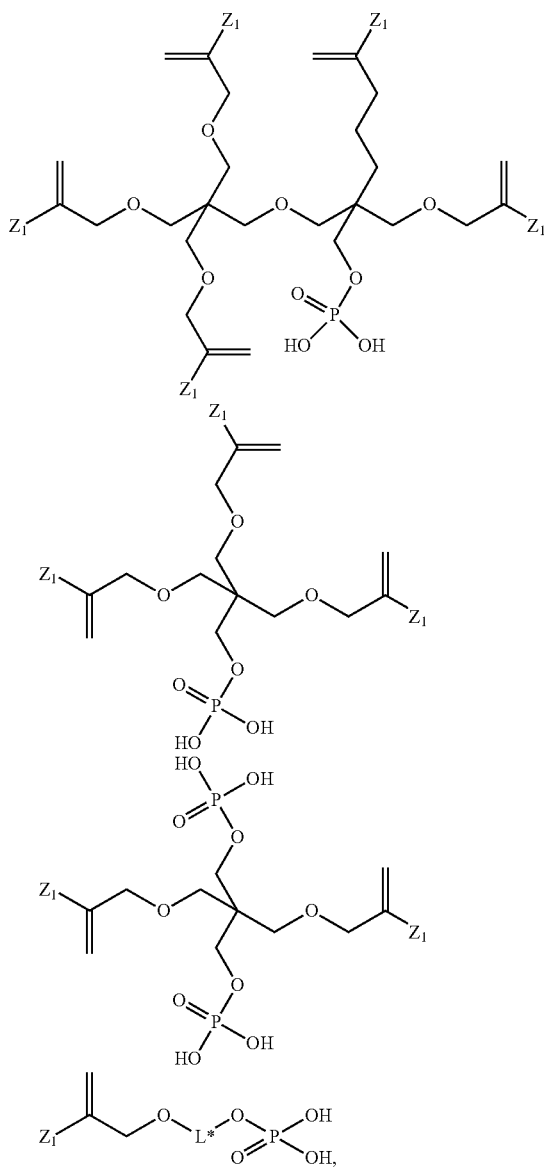

wherein $Z_1$ is defined as above, and L* is an optionally substituted alkylene group. More preferably, $Z_1$ is methyl, and L* is a $C_4$ to $C_{16}$ alkylene group. Even more preferably, L* is a $C_8$ to $C_{12}$ alkylene group.

Furthermore, compounds (i) having one or more radically polymerizable carbon-carbon double bonds may be selected from the hydrolysis stable polyfunctional polymerizable monomers disclosed in EP 2 705 827 and EP 2 727 576.

Particularly preferred compounds (i) having one or more radically polymerizable carbon-carbon double bonds are selected from the compounds of formulae (A), (B), (C), (G), (H), more preferably from the compound of formulae (A), (B), (C), and most preferably from compounds of formula (B).

The compound(s) (ii) having one or more cationically polymerizable groups are not particularly limited. However, preferably, their cationically polymerizable groups are selected from epoxide groups, oxetane groups, vinyl ether groups, aziridine groups, and azetidine groups, more preferably from epoxide groups, oxetane groups and vinyl ether groups, and most preferably from epoxide groups and vinyl ether groups.

A compound having one or more cationically polymerizable groups in the form of an epoxide and/or oxetane group may be preferably selected from the compounds of the formulae (J), (K), (L):

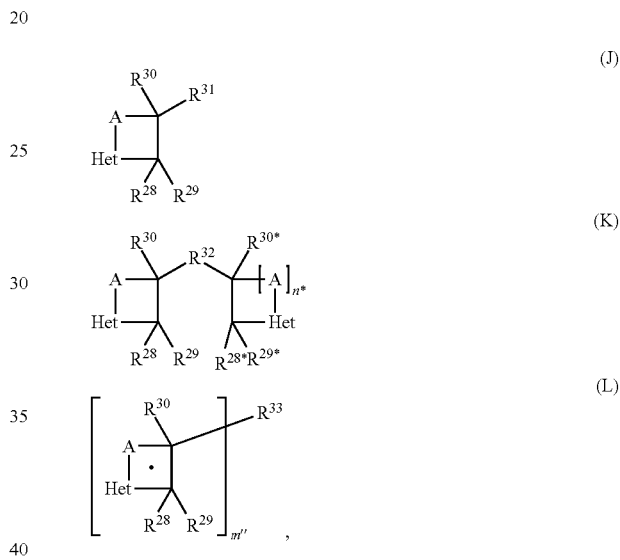

wherein

A is a single bond, a methylene (—$CH_2$—) group or a —$R^{28}CR^{29}$— in which $R^{28}$ and $R^{29}$ have the same meaning as defined below for $R^{28}$ and $R^{29}$, preferably A is a single bond or a methylene (—$CH_2$—) group, most preferably A is a single bond, Het is an oxygen atom or a nitrogen atom, preferably an oxygen atom, $R^{28}$, $R^{29}$, $R^{30}$, $R^{28*}$, $R^{29*}$, $R^{30*}$, $R^{31}$ independently represent a hydrogen atom, —COOM, or an organic moiety selected from the group consisting of a linear $C_{1-18}$ or branched or cyclic $C_{3-18}$ alkyl group which may be substituted by a $C_{3-6}$ cycloalkyl group, a $C_{6-14}$ aryl or $C_{3-14}$ heteroaryl group, —COOM, —$PO_3M$, —O—$PO_3M_2$ or —$SO_3M^*$, a $C_3$ to $C_{18}$ cycloalkyl group which may be substituted by a linear $C_{1-16}$ or branched or cyclic $C_{3-16}$ alkyl group, a $C_{6-14}$ aryl or $C_{3-14}$ heteroaryl group, —COOM, —$PO_3M$, —O—$PO_3M_2$ or —$SO_3M^*$, or a $C_5$ to $C_{1a}$ aryl or $C_3$ to $C_{18}$ heteroaryl group which may be substituted by —COOM, —$PO_3M$, —O—$PO_3M_2$ or —$SO_3M^*$, which organic moiety may be substituted with one or more substituent(s) selected from the group consisting of, $R^{32}$ represents a divalent organic residue having from 1 to 45 carbon atoms, whereby said organic residue may contain at least one of 1 to 7 $C_{3-12}$ cycloalkylene group(s), 1 to 7 $C_{6-14}$ arylene groups, 1 to 7 carbonyl groups, 1 to 7 carboxyl groups (—(C=O)—O— or —O—(C=O)—), 1 to 7 amide groups (—(C=O)—NH— or —NH—(C=O)—), 1 to 7 urethane groups (—NH—(C=O)—O— or —O—(C=O)—NH—), 1 to 14 heteroatoms selected from silicium, oxygen, nitrogen and sulphur; preferably $R^{32}$ is a $C_1$ to $C_{18}$ alkylene group which may contain at least one of 1 to 4 carboxyl groups (—(C=O)—O— or —O—(C=O)—)) or at least one moiety —SiR$^♦_2$—O—SiR$^♦_2$— wherein R$^♦$ independently represent a linear $C_{1-4}$ or branched $C_3$ or $C_4$ alkyl group, which divalent organic residue may be substituted with one or more group selected from the group consisting of —OH, —SH, —COOM, —PO$_3$M, —O—PO$_3$M$_2$ or —SO$_3$M*;

and $R^{33}$ represents a saturated di- or multivalent substituted or unsubstituted linear $C_1$ to $C_{18}$ hydrocarbon group, a saturated di- or multivalent substituted or unsubstituted branched or cyclic $C_3$ to $C_{18}$ hydrocarbon group, a di- or multivalent substituted or unsubstituted $C_6$ to $C_{18}$ aryl or heteroaryl group, a di- or multivalent substituted or unsubstituted $C_5$ to $C_{18}$ alkylaryl or alkylheteroaryl group, a di- or multivalent substituted or unsubstituted $C_7$ to $C_{30}$ aralkyl group, or a di- or multivalent substituted or unsubstituted $C_2$ to $C_{45}$ mono-, di-, or polyether residue having from 1 to 14 oxygen or sulphur atoms, and m" is an integer, preferably in the range from 1 to 10, wherein M of any one $R^{28}$, $R^{29}$, $R^{30}$, $R^{28*}$, $R^{29*}$, $R^{30*}$, $R^{31}$ and $R^{32}$, which M are independent from each other, each represent a hydrogen atom or a metal atom, and M* of any one $R^{28}$, $R^{29}$, $R^{30}$, $R^{28*}$, $R^{29*}$, $R^{30*}$, $R^{31}$ and $R^{32}$, which M are independent from each other, each represent a metal atom.

In compound of formulae (J), (K) and (L), $R^{28}$, $R^{30}$ and $R^{28*}$, $R^{30*}$ independently may cooperatively form a ring in which $R^{28}$, $R^{30}$ and $R^{28*}$, $R^{30*}$ are linked by a C—C bond or a functional group selected from the group consisting of an ether group, a thioether group, an amine group and an amide group. Preferably, $R^{28}$, $R^{30}$ and $R^{28*}$, $R^{30*}$ are linked by a C—C bond and form, together with the C—C bond located between $R^{28}$, $R^{30}$ and $R^{28*}$, $R^{30*}$ a 3 to 8 membered ring, preferably a 5 to 7 membered ring, most preferably a $C_6$ ring.

For $R^{32}$, the phrase "divalent organic residue may contain at least one of . . . " has an analogous meaning as defined above for $R_{22}$ of compound of formula (B).

It is preferred that in formula (J), Het is oxygen, $R^{28}$ and $R^{29}$ independently represent a linear $C_{18}$ or branched or cyclic $C_{3-8}$ alkyl group which may be substituted with one or more —OH groups. More preferably, in formula (J), Het is oxygen, $R^{28}$ and $R^{29}$ independently represent a linear $C_{1-8}$ alkyl group which may be substituted with one or more —OH groups, and $R^{30}$ and $R^{31}$ represent hydrogen atoms, wherein A is preferably a methylene (—CH$_2$—) group.

It is preferred that in formula (K), A is a single bond, Het is oxygen, $R^{28}$, $R^{30}$ and $R^{28*}$, $R^{30*}$ independently cooperatively form a ring in which $R^{28}$, $R^{30}$ and $R^{28*}$, $R^{30*}$ are linked by a C—C bond, and $R^{32}$ is a $C_1$ to $C_8$ alkylene group which may contain at least one of 1 to 4 carboxyl groups (—(C=O)—O— or —O—(C=O)—)) or at least one moiety —SiR$^♦_2$—O—SiR$^♦_2$— wherein R$^♦$ independently represent a linear $C_{1-4}$ or branched $C_3$ or $C_4$ alkyl group.

Preferably, compounds of formulae (J) and (K) are selected from the group consisting of:

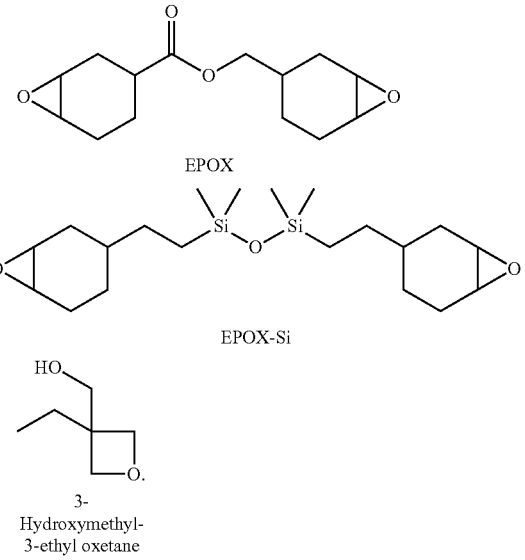

Most preferred are compounds of formula (K) being EPOX and/or EPOX-Si.

A compound having one or more cationically polymerizable groups in the form of a vinyl ether group may be preferably selected from the compounds of the formulae (M), (N), (O):

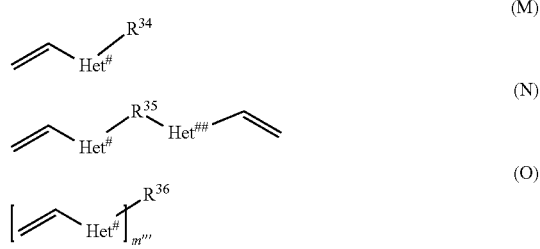

$R^{34}$ has the same meaning as $R^{21}$ defined above for formula (A) or may alternatively represent a monovalent substituted or unsubstituted $C_2$ to $C_{45}$ mono-, di-, or polyether residue having from 1 to 14 oxygen atoms, $R^{35}$ has the same meaning as $R^{22}$ defined above for formula (B), and $R^{36}$ and m''' have the same meaning as $R^{23}$ and m' as defined above for formula (C).

Preferably, in compound of formula (M), Het$^#$ is an oxygen atom and $R^{34}$ represents a linear $C_{1-14}$ or branched or cyclic $C_{3-14}$ alkyl group, or an ethylenglycol moiety of formula —[—O—CH$_2$—CH$_2$—]$_n$—R$^y$ with n=1 to 9 and R$^y$ being hydrogen or OH.

Preferably, in compound of formula (N), Het$^#$ and Het$^{##}$ are oxygen atoms and $R^{35}$ represents a $C_1$ to $C_{18}$ alkylene group which may contain at least one of 1 to 4 $C_{3-8}$ cycloalkylene group or 1 to 9 oxygen atoms, wherein the oxygen atoms may be contained such that an ethylenglycol moiety of formula —[—O—CH$_2$—CH$_2$—]$_n$— with n=1 to 9 is formed.

Most preferably, compounds of formulae (M) and (N) are selected from the group consisting of:

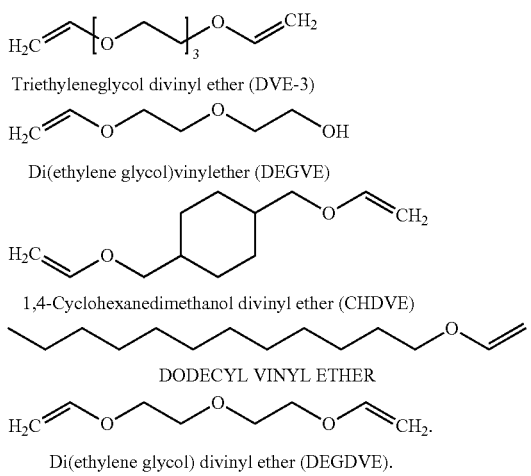

Triethyleneglycol divinyl ether (DVE-3)

Di(ethylene glycol)vinylether (DEGVE)

1,4-Cyclohexanedimethanol divinyl ether (CHDVE)

DODECYL VINYL ETHER

Di(ethylene glycol) divinyl ether (DEGDVE).

Particularly preferred compounds (ii) having one or more cationically polymerizable groups are selected from the compounds of formulae (J), (K), (M) and (N), more preferably from the compounds of formulae (K), (M) and (N).

Compound (iii) is not particularly limited. However, preferably, in compound (iii), the radically polymerizable carbon-carbon bonds are selected from (meth)acryloyl group(s) and (meth)acrylamide group(s), and the cationically polimerizable groups are selected from epoxide groups, oxetane groups, vinyl ether groups, aziridine groups, and azetidine groups.

More preferably, in compound (iii), the radically polymerizable carbon-carbon bond(s) is/are (meth)acrylamide group(s), and the cationically polymerizable groups are selected from vinyl ether groups, epoxide groups and oxetane groups. Most preferably, the cationically polymerizable group(s) is/are vinyl ether group(s) and/or epoxide group(s).

A compound (iii) having a combination of one or more radically polymerizable carbon-carbon double bonds and one or more cationically polymerizable group(s) may preferably be selected from the compounds of formula (P):

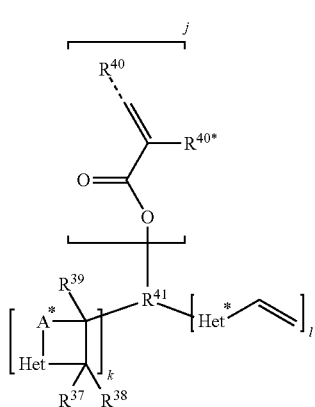

(P)

$R^{37}$, $R^{38}$, $R^{39}$ have the same meaning as $R^{28}$, $R^{29}$, $R^{30}$ defined above for formulae (J), (K) and (L), $R^{40}$, $R^{40*}$ have the same meaning as $R_{20}$ and $R_{20}*$ defined above for formulae (A), (B) and (C), $R^{41}$ has the same meaning as $R_{23}$ defined above for formula (C), j is an integer of 0 to 6, preferably 1 to 3,
k is an integer of 0 to 6, preferably 0 to 3,
j is an integer of 0 to 6, preferably 0 to 3,
with the proviso that j+k+l≥2.

In formula (P), the dotted bond indicates that $R^{40}$ may be in cis or trans configuration relative to CO.

In formula (P), $R^{37}$ and $R^{39}$ may cooperatively form a ring as defined above for $R^{28}$ and $R^{30}$ of formulae (G) and (H).

Most preferably, in compound (iii), the radically polymerizable carbon-carbon bond(s) is/are (meth)acrylamide group(s), and the cationically polymerizable groups are vinyl ether groups.

It is preferred that in compound of formula (P), j=1 to 3, k=0 and j=1 to 3, $R^{40}$ is a hydrogen atom, $R^{40*}$ is a linear $C_{1-8}$ or branched or cyclic $C_{3-8}$ alkyl group, $R^{41}$ represents a $C_1$ to $C_{18}$ alkylene group which may contain 1 to 9 oxygen atoms, wherein the oxygen atoms may be contained such that an ethylenglycol moiety of formula —[—O—CH$_2$—CH$_2$—]$_n$— with n=1 to 9 is formed.

A particularly preferred compound of formula (P) is 2-vinyloxyethoxyethyl methacrylate (VEEM) having the following structural formula:

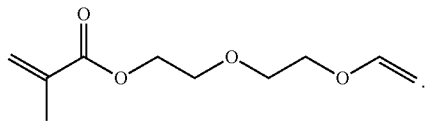

Preferably, the dental composition comprises (a) a homogeneous phase comprising monomer combinations (i) and (ii), (i) and (iii), (ii) and (iii), or (i), (ii) and (iii), most preferably monomer combinations (i) and (ii), (i) and (iii), or (i), (ii) and (iii).

Preferably, the homogeneous phase (a) comprises one or more compound(s) (i) and/or (ii) having two or more polymerizable carbon-carbon double bonds or cationically polymerizable groups, and/or one or more compound(s) (iii) having one or more polymerizable carbon-carbon double bonds and one or more cationically polymerizable groups. This provides for the formation of a crosslinked polymer network. The formation of a crosslinked polymer network is advantageous, since it imparts additional dimensional/mechanical stability to the IPN formed. More preferably, the homogeneous phase (a) comprises compound(s) (i) having two or more radically polymerizable carbon-carbon bonds selected from the group consisting of compounds of formulae (B) and (E), and/or compound(s) (ii) having two or more cationically polymerizable groups selected from the group consisting of compounds of formulae (K) and (O), and/or compound(s) (iii) having one or more polymerizable carbon-carbon double bonds and one or more cationically polymerizable groups.

For a homogeneous phase (a) comprising compound(s) (i), it is preferred that the homogeneous phase (a) contains components (i), (ii) and (iii) in a weight ratio (i)/((ii)+(iii)) of from 0.1 to 10.

The Initiator System (b)

The dental composition further comprises an initiator system (b) comprising (iv) a radical polymerization initiator, which is a compound of the following formula (I):

(I)

wherein

M is Ge or Si;

$R^1$, $R^2$ and $R^3$ may be the same or different, independently represent an organic group, and $R^4$ represents a hydrogen atom, an organic or organometallic group;

provided that when $R^4$ is a hydrogen atom, the initiator system further comprises a sensitizer compound.

The dental composition may comprise one or more compound(s) of formula (I).

It was surprisingly found that compounds of formula (I) represent radical polymerization initiators which are particularly suitable for polymerizing the compounds having one or more radically polymerizable carbon-carbon double bond(s). With compounds of formula (I), a high polymerization efficiency was attained, and no coloration problems occurred, or in a polymerization system comprising a conventional photoinitiator such as camphor quinone, coloration may efficiently be suppressed. Furthermore, compounds of formula (I) have a light absorption within the wavelength range typically applied in dental application, they are compatible with the ingredients of dental compositions and besides, they are considered physiologically harmless.

In connection with compound of formula (I), the term "substituted" as used herein means that $R^1$, $R^2$, $R^3$, $R^4$ and R' may be substituted by a substituent selected from the group consisting of halogen atoms, a nitro group, a cyano group, a hydroxy group, an amino group, $C_{1-6}$ alkyl groups, $C_{1-6}$ alkoxy groups and a $—NR^xR^y$ group wherein $R^x$ and $R^y$ independently from each other represent a $C_{1-6}$ alkyl group. Here, illustrative of the halogen atoms can be fluorine, chlorine, bromine and iodine. The $C_{1-6}$ alkyl groups are, for example, methyl, ethyl, n-propyl, isopropyl and n-butyl. Illustrative of the $C_{1-6}$ alkoxy groups are, for example, methoxy, ethoxy and propoxy. The alkyl moieties in these substituents may be linear, branched or cyclic. Preferably, the substituent is selected from a chlorine atom, a nitro group, a $C_{1-4}$ alkoxy group and a $—NR^xR^y$ group wherein $R^x$ and $R^y$ independently from each other represent a $C_{1-4}$ alkyl group.

If $R^1$, $R^2$ and $R^3$ are substituted, then it is preferred that they are substituted with 1 to 3 substituents, more preferably with 1 substituent.

In the compound of formula (I), moieties $R^1$, $R^2$ and $R^3$ may be defined as follows:

Preferably, $R^1$ and $R^2$ independently from each other represent a substituted or unsubstituted hydrocarbyl or hydrocarbylcarbonyl group, and $R^3$ represents a substituted or unsubstituted hydrocarbyl group.

The hydrocarbyl group may be an alkyl group, a cycloalkyl group, a cycloalkylalkyl group, an arylalkyl group or an aryl group.

An alkyl group may be linear $C_{1-20}$ or branched $C_{3-20}$ alkyl group, typically a linear $C_{1-18}$ or branched $C_{3-8}$ alkyl group. Examples for $C_{1-6}$ alkyl groups can include linear or branched alkyl groups having 1 to 6 carbon atoms, preferably 1 to 4 carbon atoms, for example, methyl, ethyl, n-propyl, isopropyl, n-butyl, isobutyl, sec-butyl, tert-butyl, n-pentyl, isopentyl and n-hexyl.

A cycloalkyl group may be a $C_{3-20}$ cycloalkyl group, typically a $C_{3-8}$ cycloalkyl group. Examples of the cycloalkyl group can include those having 3 to 6 carbon atoms, for example, cyclopropyl, cyclobutyl, cyclopentyl and cyclohexyl.

A cycloalkylalkyl group may have 4 to 20 carbon atoms and may include a combination of a linear or branched alkyl group having 1 to 6 carbon atoms and a cycloalkyl group having 3 to 14 carbon atoms. Examples of the cycloalkylalkyl(-) group can for example, include methylcyclopropyl(-) methylcyclobutyl(-), methylcyclopentyl(-), methylcyclohexyl(-), ethylcyclopropyl(-), ethylcyclobutyl(-), ethylcyclopentyl(-), ethylcyclohexyl(-), propylcyclopropyl(-), propylcyclobutyl(-), propylcyclopentyl(-), propylcyclohexyl(-).

An arylalkyl(-) group may be a $C_{7-20}$ arylalkyl(-) group, typically a combination of a linear or branched alkyl group having 1 to 6 carbon atoms and an aryl(-) group having 6 to 10 carbon atoms. Specific examples of an arylalkyl(-) group are a benzyl(-) group or a phenylethyl(-) group.

An aryl group can include aryl groups having 6 to 10 carbon atoms. Examples of the aryl group are phenyl and naphtyl.

The hydrocarbylcarbonyl groups of $R^1$ and $R^2$ represent acyl groups ($R_{org}—(C=O)—$) in which the organic residue $R_{org}$ is a hydrocarbyl residue as defined above.

Compound of formula (I) may contain one or two hydrocarbylcarbonyl groups, that is either one of $R^1$ or $R^2$ is a hydrocarbylcarbonyl group, or both $R^1$ and $R^2$ are hydrocarbylcarbonyl groups. Preferably, compound of formula (I) contains one hydrocarbylcarbonyl group.

Preferably, the hydrocarbylcarbonyl group is an arylcarbonyl group, more preferably a benzoyl group.

Preferably, $R^1$ and $R^2$ are independently selected from the group consisting of a linear $C_{1-6}$ or branched $C_{3-6}$ alkyl group, and a phenyl or benzoyl group which may optionally be substituted by one to three substituents selected from halogen atoms, a nitro group, a $C_{1-4}$ alkoxy group and a $—NR^xR^y$ group wherein $R^x$ and $R^y$ independently from each other represent a $C_{1-4}$ alkyl group, and $R^3$ is a linear $C_{1-6}$ or branched $C_{3-6}$ alkyl group or a phenyl group.

Most preferably, $R^1$ and $R^2$ are independently selected from the group consisting of a linear $C_{1-4}$ or branched $C_3$ or $C_4$ alkyl group, and a phenyl or benzoyl group which may optionally be substituted with one substituent selected from the group consisting of selected from a halogen atom, a nitro group, a $C_{1-4}$ alkoxy group and a $—NR^xR^y$ group wherein $R^x$ and $R^y$ independently from each other represent a $C_{1-4}$ alkyl group, and $R^3$ is a linear $C_{1-4}$ or branched $C_3$ or $C_4$ alkyl group.

According to a first preferred embodiment, $R^4$ represents a group of the following formula (V):

(V)

wherein R (i) has the following formula (VI):

(VI)

wherein M, $R^1$, $R^2$ and $R^3$ have the same meaning as defined above for formula (I), whereby the compound of formula (I) may be symmetrical or unsymmetrical; or (ii) is a group of the following formula (VII):

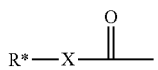
(VII)

wherein
X represents a single bond, an oxygen atom or a group NR', wherein R' represents a substituted or unsubstituted hydrocarbyl group;
R* represents a substituted or unsubstituted hydrocarbyl group, a trihydrocarbylsilyl group, a mono(hydrocarbylcarbonyl)dihydrocarbylsilyl group or a di(hydrocarbylcarbonyl)monohydrocarbylsilyl group; or
(iii) when M is Si, R may be a substituted or unsubstituted hydrocarbyl group.

For R* of formula (VII) being a trihydrocarbylsilyl group, a mono(hydrocarbylcarbonyl)-dihydrocarbylsilyl group or a di(hydrocarbylcarbonyl)monohydrocarbylsilyl group, each of the hydrocarbyl and hydrocarbylcarbonyl groups has the same meaning as defined for $R^1$, $R^2$ and $R^3$ and is independently selected therefrom.

In formula (VII), R' has the same meaning as defined for $R^3$ and is independently selected therefrom.

According to a second preferred embodiment, $R^4$ represents a hydrogen atom. Accordingly, the initiator system further comprises a sensitizer compound. The sensitizer compound is preferably an alpha-diketone sensitizer compound having a light absorption maximum in the range from 300 to 500 nm. The alpha-diketone sensitizer is capable of absorbing visible light and forming a photoexcitation complex with a hydrogen donating compound of formula (I). The alpha-diketone photoinitiator compound may be selected from camphorquinone, 1,2-diphenylethane-1,2-dione (benzil), 1,2-cyclohexanedione, 2,3-pentanedione, 2,3-hexanedione, 3,4-hexanedione, 2,3-heptanedione, 3,4-heptanedione glyoxal, biacetyl, 3,3,6,6-tetramethylcyclohexanedione, 3,3,7,7-tetramethyl-1,2-cycloheptanedione, 3,3,8,8-tetramethyl-1,2-cyclooctanedione; 3,3,18,18-tetramethyl-1,2-cyclooctadecanedione; dipivaloyl; furil, hydroxybenzil, 2,3-butanedione, 2,3-octanedione, 4,5-octanedione, and 1-phenyl-1,2-propanedione. Camphorquinone is the most preferred alpha-diketone photoinitiator. According to a preferred embodiment, the polymerizable matrix contains the alpha-diketone sensitizer in an amount from 0.05 to 5 mole percent.

If M is Si in compound of formula (I), R may be also be a substituted or unsubstituted hydrocarbyl group, wherein the hydrocarbyl group has the same meaning as defined above for $R^3$ and is independently selected therefrom.

Preferably, in the compounds of formula (I), M is Si.

For example, compounds of formula (I) wherein R has the formula (VI) and which are symmetrical may be have the following structural formulae:

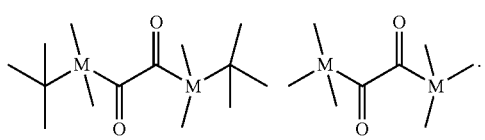

For example, compounds of formula (I) wherein R represents a group of formula (VII) wherein X is a bond, an oxygen atom or a NR' group, and R* represents a substituted or unsubstituted hydrocarbyl group may have the following structural formulae:

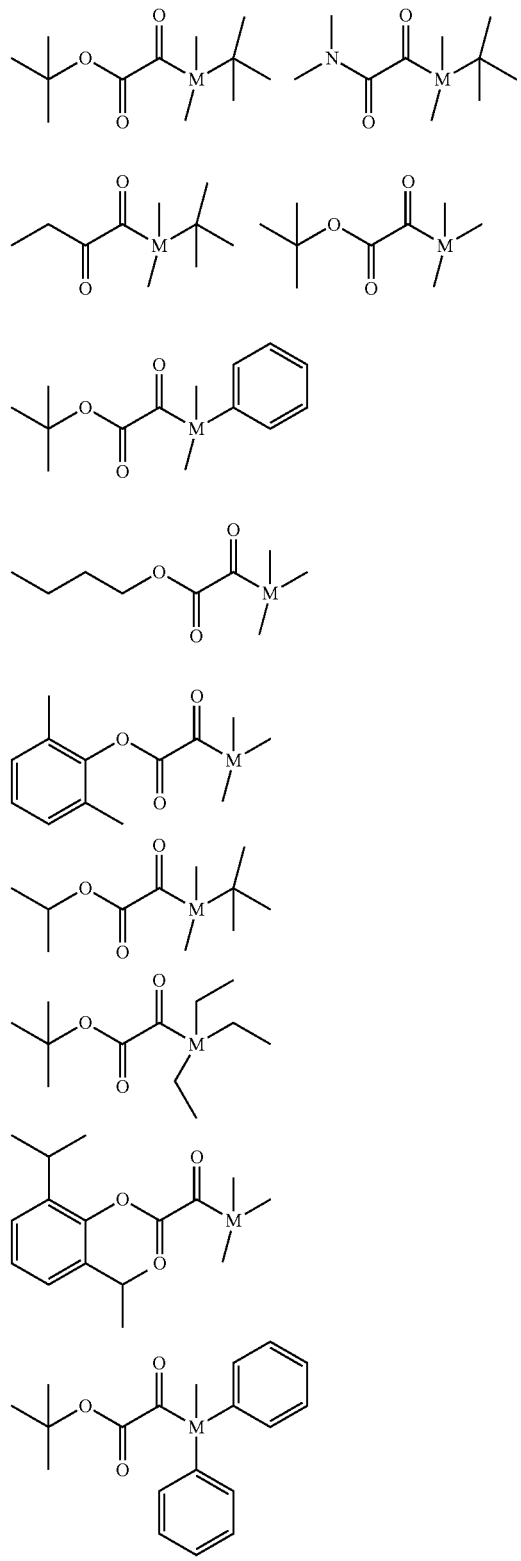

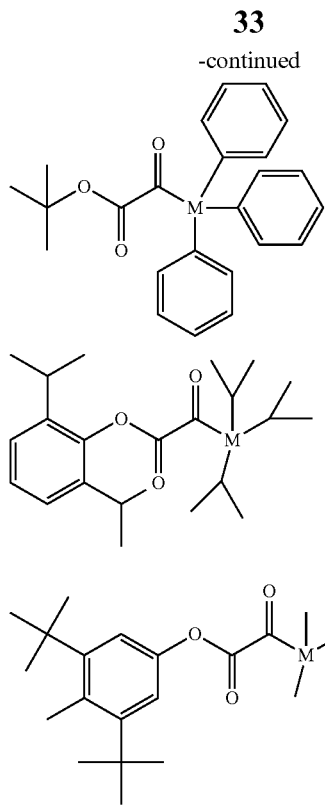

For example, compounds of formula (I) wherein R represents a group of formula (VII) wherein R* represents a trihydrocarbylsilyl group have the following structural formulae:

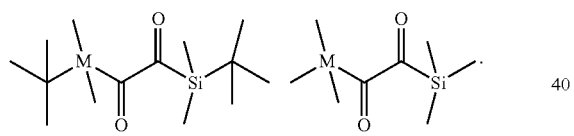

For example, compounds of formula (I) wherein M is Si and R represents a substituted or unsubstituted hydrocarbyl group may have the following structural formulae:

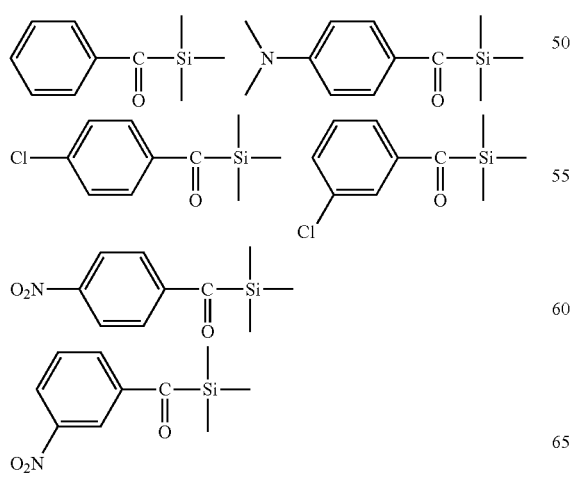

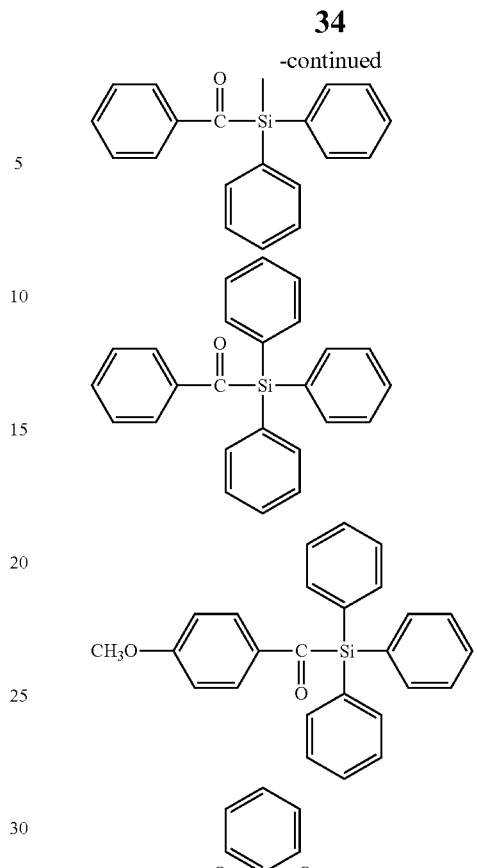

Preferably, compound of formula (I) is selected from the group consisting of:

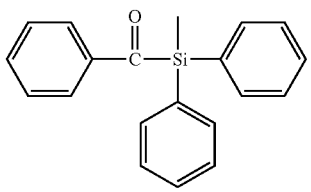

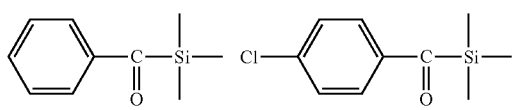

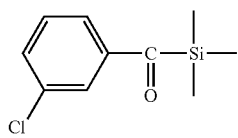

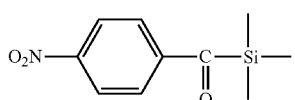

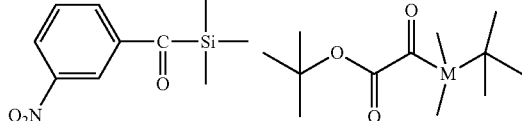

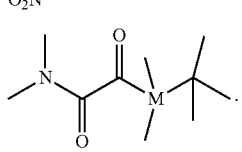

wherein compounds of formula (I) with M=Si are particularly preferred.

More preferably, compound of formula (I) is selected from the group consisting of:

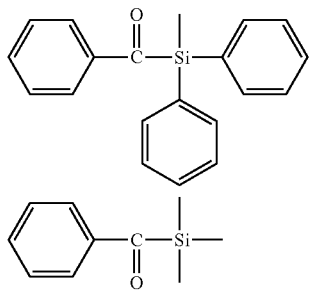

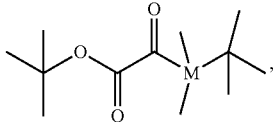

wherein it is particularly preferred that M=Si.

Most preferably, compound of formula (I) is tert-butyl (tert-butyldimethylsilyl)glyoxylate) (DKSi).

The compound of the formula (I) may be a known compound which is commercially available or a may be prepared according to published procedures.

The compound of formula (I) wherein M is Si and R represents a substituted or unsubstituted hydrocarbyl group may for example be readily prepared by means of a one-step Pd-catalyzed reaction with a disilane as described e.g. by Yamamoto K. et al., *J. Tetrahedron Lett.*, 1980, vol. 21, pages 1653 to 1656:

Scheme 1: Preparation of acylsilanes

In Scheme 1, the reaction is exemplary depicted with hexamethylsilan as the disilane, whereby a compound of formula (I) wherein $R^1$, $R^2$ and $R^3$ represent a methyl group is obtained. It is understood that $R^1$, $R^2$ and $R^3$ can be varied by applying disilanes having hydrocarbon substituents other than methyl.

The compound of formula (I) wherein R represents a group of formula (VII) in which X is an oxygen atom and R* represents a hydrocarbyl group may for example be prepared by a three-step synthesis as described by Nicewicz D. A. et al. in *Org. Synth.*, 2008, 85, pages 278 to 286. In this three-step synthesis, an acetoacetate is converted to an azide compound, which is then reacted with a trihydrocarbylsilyl-trifluoromethane-sulfonate to obtain a trihydrocarbylsilyldi-azoacetate, which is finally reacted with potassium peroxymonosulfate to arrive at the target compound:

Scheme 2: Preparation of silylglyoxylates

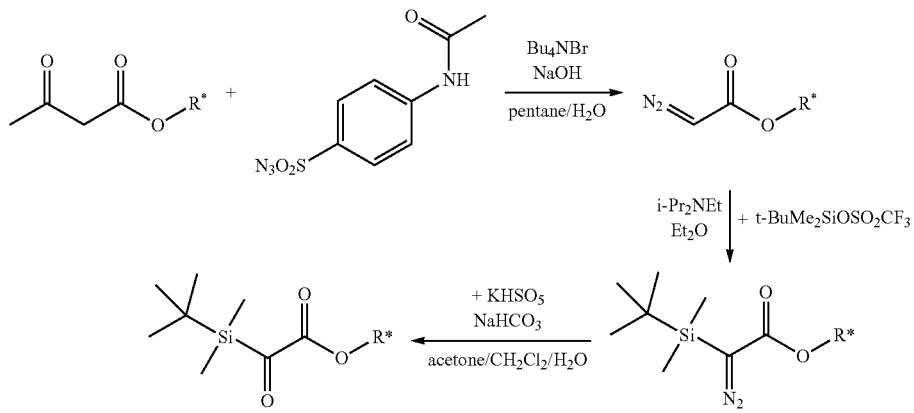

In Scheme 2, the reaction is exemplary depicted for obtaining a compound of formula (I) wherein R* of group (VII) represents a hydrocarbyl group in the form of tert-butyl. It is understood that R* can be varied by applying an acetoacetate other than tert-butyl acetoacetate.

Alternatively, compounds of formula (I) wherein M is Si, R represents a group of formula (VII) and X represents an oxygen atom may be prepared by a single-pot three-component coupling reaction of a silylglyoxylate, a terminal alkyne and an aldehyde in the presence of ZnI$_2$ and Et$_3$N as described by Nicewicz D. A. in J. Am. Chem. Soc., 2005, 127 (17), pages 6170 to 6171. Further syntheses of silylglyoxylate compounds are described e.g. by Boyce G. R. et al. in *J. Org. Chem.*, 2012, 77 (10), pages 4503 to 4515 and Boyce G. R. et al. in Org. Lett., 2012, 14 (2), pages 652 to 655.

For example, the following compounds of formula (I) are known and commercially available, and their Chemical Abstracts (CAS) No. is given in brackets: benzoyltriphenylsilane (1171-49-9), benzoyltrimethylsilan (5908-41-8), 1-[(trimethylsilyl) carbonyl]-naphthalene (88313-80-8), 1-methoxy-2-[(trimethylsilyl)-carbonyl]-benzene (107325-71-3), (4-chlorobenzoyl) (triphenyl) silane (1172-90-3), (4-nitrobenzoyl) (triphenyl) silane (1176-24-5), (methyldiphenylsilyl)phenyl-methanone (18666-54-1), (4-methoxybenzoyl) triphenylsilan (1174-56-7) and tert-butyl (tert-butyldimethylsilyl)glyoxylate (852447-17-7).

All compounds of formula (I) comprise a moiety having the following structural formula:

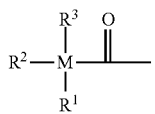

wherein M, R$^1$, R$^2$ and R$^3$ are defined as above, in which the carbonyl group derives from R$^4$ representing the group of formula (V). Depending on the selection of M, the aforementioned moiety represents an acylsilane or acylgermane group. Upon exposure to UV-VIS-light, the bond between M and the acyl group may be cleaved, whereby a silyl/germanyl and an acyl radical is formed as a polymerization initiating structure, but in competition to the cleavage into to radicals, a carbene structure might be formed:

Scheme 3: carbene formation versus radical formation

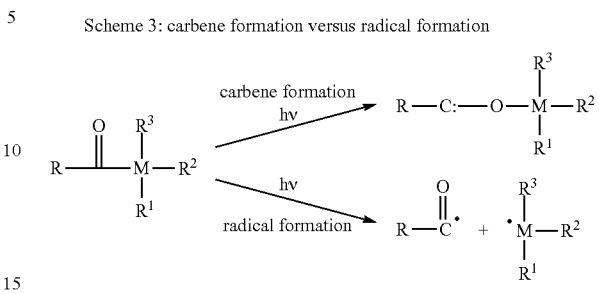

This competition between the formation of polymerization initiating radicals and carbene formation is described for acylsilanes by El-Roz, M. et al. in Current Trends in Polymer Science, 2011, vol. 15, pages 1 to 13.

Besides, in case in compound of formula (I) wherein R is a group of formula (VI) or a group of formula (VII), the C—C bond of the 1,2-diketone moiety (—C(=O)—C(=O)—) may be cleaved upon exposure to UV-VIS-light into two acyl radicals. This cleavage is exemplary shown for compound of formula (I) wherein R is a group of formula (VII) and X is an oxygen atom, that is for a glyoxylate (—O—C=O)—C(=O)—) compound:

Scheme 4: cleavage of —O—C(=O)—C(=O)— moiety of a glyoxylate

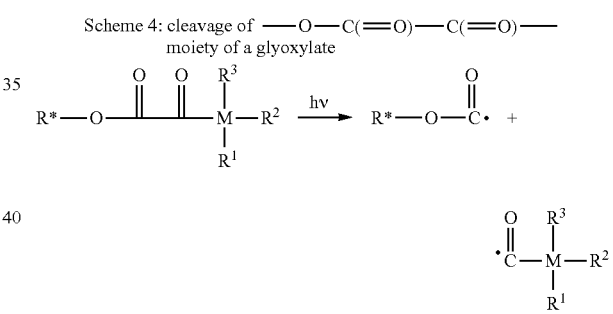

Besides, in compound of formula (I), there is a third possibility for a radical cleavage in case R is a compound of formula (VII) wherein X is an oxygen atom and R* is a substituted or unsubstituted hydrocarbyl group. Namely, an intra- or intermolecular hydrogen abstraction might occur, where a hydrogen radical is abstracted:

Scheme 5: hydrogen abstraction (intra- or intermolecular)

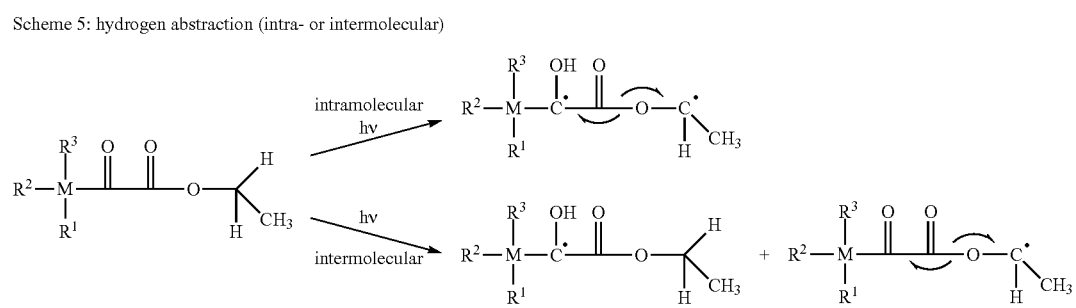

Both the cleavage of a glyoxylate group and the hydrogen abstraction mechanism is known for photoinitiators which do not contain silicium or germanium, such as ethyl phenylglyoxylate (Irgacure® MBF).

The initiator system according to (b) further comprises a cationic polymerization initiator, which is a compound selected from the following formulae (II), (III) and (IV):

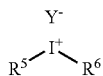
(II)

wherein
$R^5$ and $R^6$, which may be the same or different, independently represent an aryl group which may have a substituent; and
$Y^-$ represents an anion;

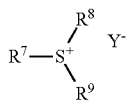
(III)

wherein
$R^7$, $R^8$ and $R^9$ which may be the same or different, independently represent an aryl group which may have a substituent; and
$Y^-$ represents an anion;

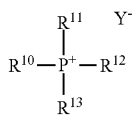
(IV)

$R^{10}$, $R^{11}$, $R^{12}$, and $R^{13}$ which may be the same or different, independently represent an alkyl or aryl group which may have a substituent; and
$Y^-$ represents an anion.

In the compounds of formulae (II), (III) and (IV), $R^5$ and $R^6$, $R^7$, $R^8$, $R^9$, $R^{10}$, $R^{11}$, $^{12}$ and $R^{13}$ represent an aryl group, preferably a $C_{6-10}$ aryl group. Preferably, the aryl group is a phenyl group. The aryl group may be substituted by one or more linear $C_{1-6}$ or branched $C_{3-6}$, linear $C_{1-6}$ or branched $C_{3-6}$ alkoxy groups, aromatic groups such as aryl groups or aryloxy groups, alicyclic groups having 3 to 6 carbon atoms, halogen atoms, hydroxyl groups, or amino groups.

Further, in formula (IV), $R^{10}$, $R^{11}$, $R^{12}$, $R^{13}$ may also represent alkyl group(s). Preferred alkyl group(s) is/are linear $C_{1-6}$ or branched $C_{3-6}$ alkyl groups which may be substituted by one or more aromatic groups, alicyclic groups having 3 to 6 carbon atoms, halogen atoms, hydroxyl groups or amino groups. An alicyclic group may be a group having 3 to 6 carbon atoms which may be substituted by one or more aromatic groups, alkyl groups, halogen atoms, hydroxyl groups or amino groups.

According to a preferred embodiment, the iodonium compound of formula (II) is selected from the group consisting of (4-methylphenyl)[4-(2-methylpropyl) phenyl] iodonium hexafluoroantimonate, include (4-methylphenyl)[4-(2-methylpropyl) phenyl] iodonium tetrafluoroborate, diphenyliodonium (DPI) tetrafluoroborate, di(4-methylphenyl)iodonium (Me2-DPI) tetrafluoroborate, phenyl-4-methylphenyliodonium tetrafluoroborate, di(4-heptylphenyl)iodonium tetrafluoroborate, di(3-nitrophenyl)iodonium hexafluorophosphate, di(4-chlorophenyl)iodonium hexafluorophosphate, di(naphthyl)iodonium tetrafluoroborate, di(4-trifluoromethylphenyl)iodonium tetrafluoroborate, DPI hexafluorophosphate, Me2-DPI hexafluorophosphate; DPI hexafluoroarsenate, di(4-phenoxyphenyl)iodonium tetrafluoroborat, phenyl-2-thienyliodonium hexafluorophosphate, 3,5-dimethylpyrazolyl-4-phenyliodonium hexafluorophosphate, DPI hexafluoroantimonate, 2,2'-DPI tetrafluoroborate, di(2,4-dichlorophenyl)iodonium hexafluorophosphate, di(4-bromophenyl)iodonium hexafluorophosphate, di(4-methoxyphenyl)iodonium hexafluorophosphate, di(3-carboxyphenyl)iodonium hexafluorophosphate, di(3-methoxycarbonylphenyl)iodonium hexafluorophosphate, di(3-methoxysulfonylphenyl)iodonium hexafluorophosphate, di(4-acetamidophenyl)iodonium hexafluorophosphate, di(2-benzothienyl)iodonium hexafluorophosphate, and DPI hexafluorophosphate.

Particularly preferred iodonium compounds of formula (II) include diphenyliodonium (DPI) hexafluorophosphate, di(4-methylphenyl)iodonium (Me2-DPI) hexafluorophosphate, diaryliodonium hexafluoroantimonate, (4-methylphenyl)[4-(2-methylpropyl) phenyl] iodonium hexafluoroantimonate, (4-methylphenyl)[4-(2-methylpropyl)phenyl] iodonium hexafluorophosphate (Irgacure® 250, commercial product available from BASF SE), (4-methylphenyl)[4-(2-methylpropyl) phenyl] iodonium tetrafluoroborate, 4-octyloxyphenyl phenyliodonium hexafluoroantimonate, 4-(2-hydroxytetradecyloxyphenyl)phenyliodonium hexafluoroantimonate, and 4-isopropyl-4'-methyldiphenyliodonium borate (PI 2074).

According to a particularly preferred embodiment, the iodonium compound of formula (II) is DPI hexafluorophosphate and/or 4-isopropyl-4'-methyldiphenyliodonium tetrakis(pentafluorophenyl) borate (PI 2074).

In formula (III), the aryl groups of $R^7$, $R^8$ and $R^9$ may be linked with each other via an alkylene, oxygen- or thio-ether bond. A preferred sulfonium compound of the formula (III) is S-(phenyl)thianthrenium hexafluorophosphate of the following formula:

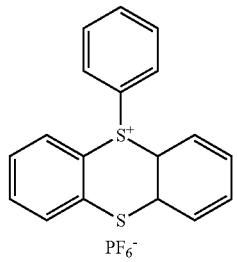

For the phosphonium compound of formula (IV) it is preferred that $R_{10}$, $R_{11}$, $R_{12}$ and $R_{13}$ independently represent aliphatic groups. Particularly preferred phosphonium compounds of formula (IV) are tetrakis-(hydroxymethyl)-phosphonium (THP) salt or a tetrakis-(hydroxymethyl)-phosphonium hydroxide (THPOH) salt, wherein the anion $A^-$ is selected from the group consisting of formate, acetate, phosphate, sulphate, fluoride, chloride, bromide and iodide.

In a salt of a compound of any one of formula (II) to (IV), the anion may be an anion selected from halogenides such as chloride, bromide and iodide, hexafluorophosphate, tetrafluoroborate, tetraphenylborate, hexafluoroantimonate, trifluoromethylsulfonate, formate, acetate, phosphate, sulphate, fluoride.

The initiators system (b) may optionally comprise (vi) a coinitiator. The coinitiator may be at least one selected from the group consisting of a compound having a Si—H or Ge—H bond, electron donors, a carbazole compound and photoinitiators other than any one of compounds of formulae (I) to (IV).

Preferably, coinitiator compounds having a Si—H or Ge—H bond are trihydrocarbylsilanes or trihydrocarbylgermanes in which the three hydrocarbyl groups have the same meaning as defined for $R_1$, $R_2$ and $R_3$. More preferably, the compound having a Si—H or Ge—H bond is triphenylsilicium hydride ($Ph_3SiH$), triphenylgermanium hydride ($Ph_3GeH$) and tris(trimethylsilyl)silane (($TMS)_3SiH$), most preferably $Ph_3GeH$ and $(TMS)_3SiH$.

Coinitiator compounds in the form of an electron donor may include, for example, amines, amides, ethers, thioethers, ureas, thioureas, ferrocene, sulfinic acids and their salts, salts of ferrocyanide, ascorbic acid and its salts, dithiocarbamic acid and its salts, salts of xanthates, salts of ethylene diamine tetraacetic acid and salts of tetraphenylboronic acid. Particularly preferred donors contain an electron donor atom such as a nitrogen, oxygen, phosphorus, or sulfur atom, and an abstractable hydrogen atom bonded to a carbon or silicon atom alpha to the electron donor atom.

Particularly preferred amine compounds are tertiary amines selected from the group consisting of triethanolamine, 4-N,N-dimethylaminobenzonitrile, methyl N,N-dimethylaminobenzoate, ethyl N,N-dimethylaminobenzoate, N,N-dimethylaminoethyl methacrylate and isoamyl 4-N,N-dimethylaminobenzoate, N,N-dimethylaniline, N,N-dimethyltoluidine, N,N-diethanoltoluidine, dimethylaminoanisole, 1 or 2-dimethylaminonaphthalene. In particular, the tertiary amine is selected from the group consisting of triethanolamine, methyl 4-N,N-dimethylaminobenzoate, ethyl 4-N,N-dimethylaminobenzoate, 4-N,N-dimethylaminoethyl methacrylate and isoamyl 4-N,N-dimethylaminobenzoate.

Carbazole compounds may also be used as coinitiator compounds. It is known for example from J. Lalevee et al., "*N-Vinylcarbazole: An Additive for Free Radical Promoted Cationic Polymerization upon Visible Light*", ACS Macro Lett, 1, pages 802-806, 2012, that N-vinylcarbazole may be used as a powerful additive for the cationic photopolymerization of epoxy monomers. However, N-vinylcarbazole is relatively toxic. For this reason, the present inventors searched for a carbazole compound which is physiologically harmless, and which improves cationic polymerization of both cationically polymerizable monomers and monomer blends for IPN synthesis, for example a blend of cationically polymerizable monomers and radically polymerizable monomers, such as methacrylate/epoxy or methacrylate/vinylether blends. Thereby, the inventors surprisingly found that 9H-carbazole-9-ethanol (CARET) having the structural formula:

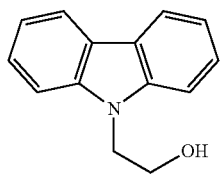

fullfills the aformentioned requirements.

Without wishing to be bound to theory, it is believed that CARET improves cationic polymerization owing to its capability to donate a proton. The proposed hydrogen abstraction mechanism is shown in FIG. 20:

As can be seen from FIG. 20, CARET may convert aryl radicals ($Ar^\bullet$) generated from the photoinitiator/iodonium salt interaction in an initiator system such as CQ/DPI or DKSi/DPI, to the cationic species $CARET_{(-H)}^+$ that seems very efficient to initiate a cationic polymerization. Since aryl radicals are not initiating species for cationic polymerization, this $Ar^\bullet \rightarrow CARET_{(-H)}^+$ conversion explains the better performance of the initiator system (c) when a carbazole compound such as CARET is added as coinitiator. Further, from the above proposed mechanism, it appears that the carbazole compound requires hydrogen donating properties for rendering possible donation of a hydrogen to the radical $Ar^\bullet$.

Preferably, the carbazole compound having hydrogen donating properties is 9H-carbazole-9-ethanol (CARET).

The coinitiator may also be a photoinitiator other than compounds of formulae (I) to (IV). Such a photoinitiator may for example be added to improve the matching of the emission spectrum of dental LED with the absorption of the photo-initiating system. For example, if compound of formula (I) does not or not sufficiently absorb light within the range of 450 to 500 nm, as in case when $R^4$ in formula (I) is a hydrogen atom, it is preferred, and in case when $R^4$ is a hydrogen atom, it is essential to add a sensitizer having a good absorption within this range.

A sensitizer (vi) in the form of a photoinitiator other than any one of compounds of formulae (I) to (IV) may be of a Norrish type I or type II photoinitiator.

The Norrish type I photoinitiator may be selected from the group consisting of a triazine derivate, 2,4-6-trimethylbenzoyl-diphenylphosphine oxide (Irgacure® TPO), 2,4-6-trimethylbenzoyl-diphenylphosphinate (Irgacure® TPO-L, TPO-L), bis(2,4-6-trimethylbenzoyl)-phenylphosphineoxide (Irgacure® BAPO-X). Preferably, the Norrish type I photoinitiator is a triazine derivative, preferably tris(trihaloalkyl)-triazine, more preferably tris(trihalomethyl)-triazine, even more preferably tris(trichloromethyl)-triazine and in particular 2,4,6-tris(trichloromethyl)-1,3,5-triazine.

Typical Norrish type II photoinitiators are e.g a 1,2-diketone or a 1,3 diketone. Examples of suitable 1,2-diketones are camphor quinone, benzil, 2,2'-3 3'- and 4,4'-dihydroxylbenzil, 2,3-butanedione, 2,3-pentanedione, 2,3-hexanedione, 3,4-hexanedione, 2,3-heptanedione, 3,4-heptanedione, 2,3-octanedione, 4,5-octanedionefuril, biacetyl, 1,2-cyclohexanedione, 1,2-naphthaquinone, and acenaphthaquinone. Examples of suitable 1,3-diketones are dibenzoyl methane, benzoyl acetone and acetyl propionyl methane.

Preferably, the sensitizer is a Norrish type II photoinitiator, more preferably a 1,2-diketone, most preferably camphorquinone.

By means of adding a photoinitiator such as camphor quinone as a sensitizer, the matching of the absorption of initiator system comprising the compound of formula (I) with the emission spectrum of an irradiation source may be improved compared to a conventional initiator system based on a conventional Norrish type I or II photoinitiator.

Providing an initiator system (b) comprising (iv) a compound of formula (I) and an optional coinitiator (vi) together with (v) a compound selected of formulae (II), (II) and (IV)

may provide for a synergistic effect, in particular in the case where the initiator system comprises a iodonium salt of formula (II).

Preferably, the initiator system (b) comprises a compound of formula (II).

More preferably, the initiator system (b) comprises:
(iv) a compound of formula (I),
(v) a compound of formula (II), and
(vi) at least one coinitiator selected from the group consisting of an amine compound, a compound having a Si—H or Ge—H bond, and a carbazole compound, and additionally a coinitiator being a 1,2 diketone sensitizer.

Most preferably, the initiator system (b) comprises
(iv) a compound of formula (I), preferably selected from the group consisting of benzoyldiphenylmethylsilane (BDMSi), benzoyltrimethylsilane (BTMSi) and tert-butyl (tert-butyldimethylsilyl)glyoxylate (DKSi), more preferably DKSi,
(v) a diphenyliodonium (DPI) salt, preferably DPI hexafluorophosphate and/or 4-isopropyl-4'-methyldiphenyliodonium tetrakis(pentafluorophenyl) borate (PI2074), and
(vi) at least one coinitiator selected from the group consisting of triphenylgermanium hydride (Ph$_3$GeH), tris(trimethylsilyl)silane ((TMS)$_3$SiH) and 9H-carbazole-9-ethanol (CARET), and optionally additionally camphor quinone (CQ).

It was surprisingly found that owing to synergistic effects between components (iv), (v) and (vi), a higher conversion rate and more advantageous kinetics in terms of the polymerization time can be obtained for the homogeneous phase (a) compared with an initiator system consisting of components (iv) and (v). Furthermore, an initiator system comprising components (iv), (v) and (vi) is particularly suitable for polymerizing relatively thin films of up to 0.1 mm, such as adhesive films, as well as for relative thick samples having a thickness of about 1 to 2 mm or more, such as fillings and prosthetics. Besides, an initiator system comprising components (iv), (v) and (vi) provides for good bleaching, that is, colorless polymers are obtained. When camphor quinone (CQ) is used as additional coinitiator, for the initiator system comprising components (iv), (v) and (vi), the aforementioned effects may significantly improve compared to a conventional initiator system consisting of camphor quinone (CQ) as polymerisation initiator in combination with components (v) and (vi).

As an additional component of the initiator system, the initiator system may optionally further comprise
(vii) an aromatic tertiary phosphine compound of the following formula (VIII):

wherein
Z is a group of the following formula (IX)

wherein
$R^{15}$ represents a substituted or unsubstituted hydrocarbyl group;
Ar represents a substituted or unsubstituted aryl or heteroaryl group;
$R^{14}$ is a substituted or unsubstituted hydrocarbyl group or a group LZ', wherein
L is a substituted or unsubstituted divalent hydrocarbyl group which may contain a linkage selected from an ether linkage, a thioether linkage, an ester linkage, an amide linkage, and a urethane linkage and
Z' has the same meaning as Z, whereby Z and Z' may be the same or different;
wherein the group $R^{15}$ and Ar may be substituted by one or more groups selected from a hydroxyl group, an oxo group, a —NR$^{16}$R$^{17}$ group (wherein R$^{16}$ and R$^{17}$, which may be the same or different, are selected from a hydrogen atom and C$_{1-6}$ alkyl groups), a carboxyl group, and a group having a polymerizable double bond, and
$R^{14}$ and L may be substituted by one or more groups selected from a hydroxyl group, an oxo group, a —NR$^{16}$R$^{17}$ group (wherein R$^{16}$ and R$^{17}$, which may be the same or different, are selected from a hydrogen atom and C$_{1-6}$ alkyl groups), a carboxyl group, and a group having a polymerizable double bond.

The aromatic tertiary phosphine compounds of formula (VIII) may provide for both an advantageous efficiency in terms of a higher polymerisation rate and a higher final conversion rate compared to a dental composition comprising a initiator system without an aromatic tertiary phosphine compound of formula (VIII). Advantageously, the polymeriation rate may be adjusted within a range which still provides for corrections when applying the dental composition to a patient's tooth or when forming a prosthesis. Although photopolymerization may be achieved at a higher polymerisation and conversion rate, owing to the present initiator system, undesired side reaction resulting e.g. in discoloration of the cured dental composition bay be effectively suppressed.

In the aromatic tertiary phosphine compound of the formula (VIII), moieties Z, $R^{14}$, Ar, $R^{15}$, L, Z, Z' may be defined as follows:

For $R^{15}$, the monovalent hydrocarbyl group may be an alkyl group, a cycloalkyl group, a cycloalkylalkyl group, an arylalkyl group or an aryl group.

Ar represents a substituted or unsubstituted aryl or heteroaryl group. An aryl group may be selected from a phenyl group, a naphtyl group, a tolyl group, a xylyl group, and a styryl group. A heteroaryl group may be a pyridyl group.

L is a substituted or unsubstituted divalent hydrocarbyl group which may contain a linkage selected from an ether linkage, a thioether linkage, an ester linkage, an amide linkage, and a urethane linkage. For L, the divalent hydrocarbyl group may be an alkyldiyl group, a cycloalkyldiyl group, a cycloalkylalkyl-diyl group, an arylalkyl-diyl group or an aryldiyl group. In a cycloalkylalkyl-diyl, one valency may be bonded to each of the cycloalkyl moiety or the alkyl moiety, or both valencies may be bonded to either the cycloalkyl moiety or the alkyl moiety. In a arylalkyl-diyl group, each of the aryl moiety or the alkyl moiety may be monovalent respectively, or either the aryl moiety or the alkyl moiety is divalent, while the other moiety is nonvalent. In a cycloalkylalkyl-diyl, each of the cycloalkyl moiety or the alkyl moiety may be monovalent respectively, or either the cycloalkyl moiety or the alkyl moiety is divalent, while the other moiety is nonvalent.

The following definitions apply both for the monovalent and the divalent hydrocarbyl group, therefore, for the definition of the divalent hydrocarbyl group, the suffixes "diyl" and "-diyl" are bracketed.

An alkyl(diyl) group may be linear C$_{1-20}$ or branched C$_{3-20}$ alkyl(diyl) group, typically a C$_{1-8}$ alkyl(diyl) group. Examples for a C$_{1-6}$ alkyl(diyl) group can include linear or branched alkyl(diyl) groups having 1 to 6 carbon atoms, preferably 1 to 4 carbon atoms, for example, methyl(diyl), ethyl(diyl), n-propyl(diyl), isopropyl(diyl), n-butyl(diyl), isobutyl(diyl), sec-butyl(diyl), tert-butyl(diyl), n-pentyl (diyl), isopentyl(diyl) and n-hexyl(diyl).

A cycloalkyl(diyl) group may be a $C_{3-20}$ cycloalkyl(diyl) group. Examples of the cycloalkyl(diyl) group can include those having 3 to 14 carbon atoms, for example, cyclopropyl (diyl), cyclobutyl(diyl), cyclopentyl(diyl) and cyclohexyl (diyl). A cycloalkylalkyl(diyl) group can include those having 4 to 20 carbon atoms.

A cycloalkylalkyl(-diyl) group can include a combination of a linear or branched alkyl(diyl) group having 1 to 6 carbon atoms and a cycloalkyl(diyl) group having 3 to 14 carbon atoms. Examples of the cycloalkylalkyl(-diyl) group can for example, include methylcyclopropyl(-diyl) methylcyclobutyl(-diyl), methylcyclopentyl(-diyl), methylcyclohexyl(-diyl), ethylcyclopropyl(-diyl), ethylcyclobutyl(-diyl), ethylcyclopentyl(-diyl), ethylcyclohexyl(-diyl), propylcyclopropyl(-diyl), propylcyclobutyl(-diyl), propylcyclopentyl(-diyl), propylcyclohexyl(-diyl).

An arylalkyl(-diyl) group may be a $C_{7-20}$ arylalkyl(-diyl) group, typically a combination of a linear or branched alkyl(-diyl) group having 1 to 6 carbon atoms and an aryl(-diyl) group having 6 to 10 carbon atoms. Specific examples of an arylalkyl(-diyl) group are a benzyl(-diyl) group or a phenylethyl(-diyl) group.

An aryl(diyl) group can include aryl(diyl) groups having 6 to 10 carbon atoms. Examples of the aryl(diyl) group are phenyl(diyl) and naphtyl(diyl). Aryl(diyl) groups may contain 1 to 3 substituents. Examples of such substituents can include halogen atoms, a cyano group, a hydroxy group, an amino group, $C_{1-6}$ alkyl groups and $C_{1-6}$ alkoxy groups. Here, illustrative of the halogen atoms can be fluorine, chlorine, bromine and iodine. The $C_{1-4}$ alkyl(diyl) groups are, for example, methyl(diyl), ethyl(diyl), n-propyl(diyl), isopropyl(diyl) and n-butyl(diyl). Illustrative of the $C_{1-4}$ alkoxy(diyl) groups are, for example, methoxy(diyl), ethoxy (diyl) and propoxy(diyl). The alkyl(diyl) moieties in these substituents may be linear, branched or cyclic.

Preferably, the hydrocarbyl group is an aryl(diyl) group selected from a phenyl(diyl) group and a naphthyl(diyl) group, which groups may optionally be substituted by one to three groups selected from halogen atoms, a cyano group, an amino group, a hydroxy group, $C_{1-6}$ alkyl groups and C1-6 alkoxy groups, or wherein the hydrocarbyl group is a non-aromatic hydrocarbyl group selected from a straight chain or branched alkyl group, a straight chain or branched alkenyl group, or a straight chain or branched alkynyl group.

The $C_{1-8}$ alkyl(diyl) group and the $C_{3-14}$ cycloalkyl(diyl) group may optionally be substituted by one or more members of the group selected from a $C_{1-4}$ alkyl group, $C_{1-4}$ alkoxy group, a phenyl group, and a hydroxy group. Examples for a $C_{1-4}$ alkyl group can include linear or branched alkyl groups having 1 to 4 carbon atoms, for example, methyl, ethyl, n-propyl, isopropyl, n-butyl, isobutyl, sec-butyl, tert-butyl. Examples for an $C_{1-4}$ alkoxy group can include linear or branched alkoxy groups having 1 to 4 carbon atoms, for example, methoxy, ethoxy, n-propoxy, isopropoxy, n-butoxy, isobutoxy, sec-butoxy, and tert-butoxy.

Moreover, in formula (VII), any of the hydrocarbyl group may be substituted by on or more groups selected from halogen atoms, a cyano group, an amino group or a hydroxy group. Accordingly, in the hydrocarbyl groups some or all hydrogen atoms are replaced by halogen atoms (e.g., fluoro, bromo, chloro), for example, halo-substituted alkyl groups such as chloromethyl, chloropropyl, bromoethyl and trifluoropropyl, and cyanoethyl.

In case the hydrocarbyl group contains an alkyl(diyl) chain, one or more carbon atoms in the alkyl(diyl) chain may be replaced by an oxygen atom, a sulfur atom, an amide group, an ester group, or a urethane group. In case the hydrocarbyl group is an alkyl group having more than one carbon atom, the alkyl group contains an alkylene. Accordingly, in case the hydrocarbyl group is an n-hexyl group, any of the carbon atoms of the alkylene chain excluding the terminal methyl group may be replaced by an oxygen atom, a sulfur atom, an amide group, an ester group, a urethane group or an NH group. Therefore, the following groups may be given as specific examples in case of one or more oxygen atoms:

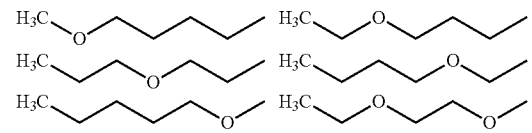

In formula (VIII), group $R^{15}$ and/or Ar as well as $R^{14}$ and/or may be substituted with a polymerizable double bond, preferably a carbon-carbon double bond. Examples of polymerizable carbon-carbon double bonds include vinyl, conjugated vinyl, allyl, acryl, methacryl and styryl. Preferably, the polymerizable double bond is selected from the group consisting of methacryl, acryl and styryl. More preferably, the double bond is styryl.

Preferably, $R^{15}$ and Ar independently are aromatic hydrocarbyl groups selected from a phenyl group, a naphtyl group, a tolyl group, a xylyl group, and a styryl group.

As regards $R^{14}$, this moiety is preferably an aryl group, which may be substituted by one or more groups selected from a hydroxyl group, an amino group, a $—NR^{16}R^{17}$ group (wherein $R^{16}$ and $R^{17}$, which may be the same or different, are selected from $C_{1-6}$ alkyl groups), a carboxyl group, and a group having a polymerizable double bond. Alternatively, $R^{14}$ is preferably a group LZ' wherein Z' and Z are the same.

More preferably, $R^{14}$ is a $C_{1-6}$ alkyl group or a $C_{1-6}$ alkenyl group, which groups may be substituted by one or more groups selected from a hydroxyl group, an amino group, a $—NR^{16}R^{17}$ group (wherein $R^{16}$ and $R^{17}$, which may be the same or different, are selected from $C_{1-6}$ alkyl groups), a carboxyl group, and a group having a polymerizable double bond. The group having a polymerizable double bond may be vinyl group, an allyl group, a (meth) acryloyloxy group or a (meth) acryloylamido group.

Even more preferably, the aromatic phosphine compound is a compound of formula (VIII) wherein Z is a group of the following formula (V'):

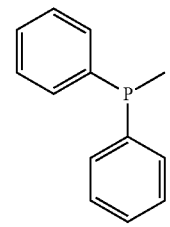

Specific examples for a compound of formula (VIII) include triphenyl phosphine (TPP), 4-(diphenylphosphino)styrene (DPPS), 4-(diphenylphosphino)benzoic acid, 4-(diphenylphosphino) benzoic acid, 3-(diphenylphophonino) propionic acid, (4-(diphenylphosphino) N,N'-dimethylaniline, 2,2'-bis(diphenylphosphino)benzophenone (BDPPEP), bis[2-(diphenylphosphino)phenyl]ether (BDPPE), (4-Hydroxyphenyl)diphenylphosphine, allyldiphenylphosphine. Preferably, the compound of formula (I) is triphenyl phosphine (TPP) or 4-(diphenylphosphino)styrene (DPPS), more preferably 4-(diphenylphosphino)styrene (DPPS).

The present initiator system is not only advantageous for relatively thin films of up to 0.1 mm such as adhesive films, but also particularly suitable for polymerizing relative thick samples of a dental composition having a thickness of about 1 to 2 mm or more, such as fillings and prosthetics.

Without wishing to be bound to theory, it is believed that a synergistic effect due to the combination of the compounds of formulae (iv) and (v) and the optional components (vi) and/or (vii) is provided according to the present invention.

A further positive effect associated with the application of tertiary phosphines of formula (VIII) is that owing to the tertiary phosphines of formula (VIII), the present compositions may exhibit an advantageous storage stability, that is the compositions keep the above characteristics of an advantageous efficiency in terms of a higher polymerisation rate and a higher final conversion rate even after a long storage time, e.g. about 2 month.

From the above listed aromatic tertiary compounds of formula (VIII), 4-(diphenylphosphino)styrene (DPPS) is particularly preferred, since this compound provides for particularly improved photo-bleaching results compared to the already advantageous results obtained with triphenyl phosphine (TPP). Besides, DPPS is particularly suitable for initiating polymerization of thick samples of about 1 to 2 mm thickness. Besides, DPPS not only provides for an improved conversion rate, but with DPPS, the conversion rate of the dental composition can be maintained even after a storage time of 2 weeks or more.

Preferably, in the present dental composition, the initiator system comprises components (iv), (v), (vi) and (vii) in a molar ratio ((iv):(v):(vi):(vii)) of 1:(0.1 to 3.0):(0.1 to 3.0):(0.0 to 3.0), more preferably 1:(0.1 to 2.0):(0.1 to 2.0):(0.0 to 2.0), even more preferably 1:(0.2 to 1.0):(0.2 to 1.0):(0.0 to 1.0).

It is preferred that the dental composition contains 0.1 to 5 percent by weight of the initiator system.
Further Components Optionally, the dental compositions of the present invention may further comprise stabilizer(s), solvent(s), curing indicator(s), radiopacifier(s) and/or particulate filler(s) such as pigments, e.g. for coloring.

The dental composition may comprise one or more stabilizer(s).

The term "stabilizer" as used herein means any compound capable of preventing polymerizable compounds contained in the dental composition from spontaneous polymerization during storage. However, the stabilizer does not disturb or prevent intended polymerisation curing of the dental composition during application.

For example, the stabilizer may be a conventional stabilizer selected from the group consisting of hydroquinone, hydroquinone monomethylether, tert-butyl-hydroquinone, tert-butylhydroxyanisol, propyl gallate and 2,6-di-tert-butyl-p-cresol. From these conventional stabilizers, 2,6-di-tert-butyl-p-cresol is preferred.

Preferably, the stabilizer is a compound of the following formula (X) and/or (XI):

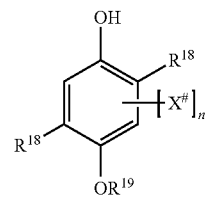
(X)

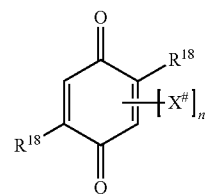
(XI)

wherein the $R^{18}$, which may be the same or different, independently represent a branched $C_{3-8}$ alkyl group or alkenyl or a $C_{3-8}$ cycloalkyl or cycloalkenyl group, $R^{19}$ represents a $C_{1-6}$ alkyl or $C_{2-6}$ alkenyl group, or a $C_{1-6}$ fluoroalkyl or $C_{2-6}$ fluoroalkenyl group, $X^{\#}$ represents a group selected from a $C_{1-8}$ alkyl group or a $C_{3-8}$ cycloalkyl group, and n is 0, 1 or 2.

It was surprisingly found that the class of stabilizers of formula (X) and/or (XI) provides for full or at least substantial avoidance of discoloration upon storage and/or during photocuring. In particular, this class of stabilizers provides for a surprising stabilizing effect in an acidic aqueous mixture so that a dental composition having a pH of less than 7 may be provided which has no or substantially no discoloration upon storage and an excellent storage stability due to an improved resistance against premature polymerization.

More preferably, the stabilizer is a compound of formula (X) and/or (XI) wherein the $R^{18}$, which may be the same or different, independently represent a branched $C_{3-8}$ alkyl group or a $C_{3-8}$ cycloalkyl group, and $R^{19}$ represents a $C_{1-6}$ alkyl group or a $C_{1-6}$ fluoroalkyl group, and n is 0 or 1. Even more preferably, the stabilizer is a compound of formula (IX) and/or (X) wherein the $R^{18}$, which may be the same or different, independently represent a branched $C_{3-8}$ alkyl group and $R^{19}$ represents a $C_{1-6}$ alkyl group, and n is 0. Most preferably, the stabilizer is a compound of the following formulae (Xa), (Xb) or (XIa):

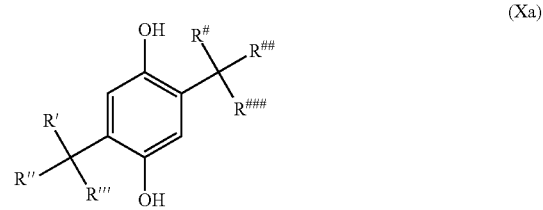
(Xa)

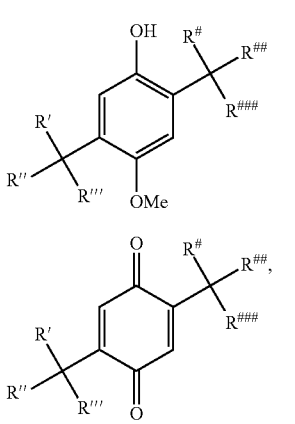

(Xb)

(XIa)

wherein R', R", R''', R#, R## and R###, which may be the same or different, independently represent a methyl or an ethyl group. It is particularly preferred that the stabilizer of formulae (Xa), (Xb) or (XIa) is a compound of the following formulae:

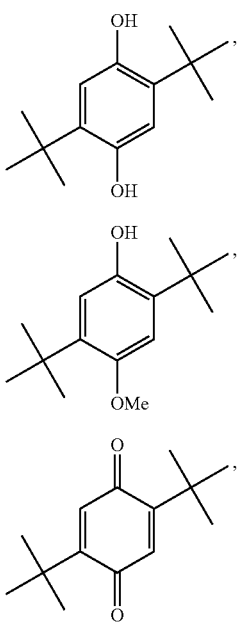

(DTBHQ)

(DTBMP)

(DTBBQ)

preferably DTBHQ.

The stabilizer DTBHQ is particularly preferred, since from experimental testings it appears that this stabilizer provides the best results in view of the discoloration problematic, i.e. there is no or almost no discoloration of the dental composition upon storage at 50° C. for 30 days.

Discoloration upon storage and/or during photocuring may be determined according to ISO 7491:2000(en).

The dental composition according to the invention may contain the stabilizer in an amount of 0.001 to 1 percent by weight, preferably 0.005 to 0.8 percent by weight based on the total weight of the composition. When the amount of the stabilizer is below the above indicated lower limit of 0.001, then storage stability of the dental composition might be insufficient, since the amount of stabilizer is too small to provide a stabilizing effect. However, when the amount of stabilizer is above the maximum threshold of 1 percent by weight, then the applicability of the dental composition might be negatively affected, since higher amounts of stabilizer may disturb or even substantially prevent intended polymerisation curing of the dental composition during application.

Suitable solvents may be selected from water, alcohols such as methanol, ethanol, propanol (n-, i-), butanol (n-, iso-, tert.-), ketones such as acetone or the like.

The dental composition of the present invention may preferably comprise 5 to 75 percent by weight based on the total weight of the composition of a solvent.

Suitable particulate fillers may be selected from fillers currently used in dental compositions. The filler should be finely divided and preferably has a maximum particle diameter less than about 100 μm and an average particle diameter less than about 10 μm. Most preferably, the filler has an average particle diameter of less than 1 μm. The filler may have a unimodal or polymodal (e.g., bimodal) particle size distribution.

The filler can be an inorganic material. It can also be a crosslinked organic material that is insoluble in the polymerizable resin, and is optionally filled with inorganic filler. The filler can be radioopaque. Examples of suitable particulate inorganic fillers are naturally-occurring or synthetic materials such as quartz, nitrides such as silicon nitride, glasses derived from, for example Ce, Sb, Sn, Zr, Sr, Ba and Al, colloidal silica, feldspar, borosilicate glass, kaolin, talc, titania, and zinc glass, and submicron silica particles such as pyrogenic silicas. Examples of suitable non-reactive organic filler particles include filled or unfilled pulverized polycarbonates or polyepoxides. Preferably the surface of the filler particles is treated with a coupling agent in order to enhance the bond between the filler and the matrix. The use of suitable coupling agents include gamma-methacryloxypropyltrimethoxysilane, gamma-mercaptopropyltriethoxysilane, gamma-aminopropyltrimethoxysilane, and the like.

The particulate filler may also be a filler obtainable by a process for the preparation of composite filler particles, comprising:

(a) coating a particulate filler having a median particle size (D50) of from 1 to 1200 nm with a coating composition containing a film-forming agent forming a coating layer on the surface of the particulate filler, said coating layer displaying reactive groups on the surface of the coating layer, said reactive groups being selected from addition polymerizable groups and step-growth polymerizable groups, thereby forming a coated particulate filler; subsequently or concurrently (b) agglomerating the coated particulate filler, optionally in the presence of a further crosslinking agent and optionally in the presence of a further particulate filler not displaying reactive groups, for providing a granulation of the coated particulate filler wherein the granulation contains the coated particulate filler particles and the optional further particulate filler particles separated from and connected to each other by at least one coating layer, whereby the at least one coating layer may be crosslinked by crosslinking groups obtained by reacting the reactive groups and optionally a further crosslinking agent;

(c) optionally milling, classifying and/or sieving the granulation of the coated particulate filler; and (d) optionally further crosslinking the granulation of the coated particulate filler; for providing composite filler particles having a median particle size (D50) of from 1 to 70 μm, wherein reactive groups are transformed into crosslinking groups obtained by reacting reactive groups and optionally a further crosslinking agent, and wherein the particulate filler is the main component by volume of the composite filler particles as further described in EP-A 2 604 247.

The dental composition of the present invention may preferably comprise 0.1 to 85 percent by weight based on the total weight of the composition of particulate filler.

The dental compositions of the present invention may further contain preservatives, pigments, free radical scavengers, reactive and nonreactive diluents, coupling agents to enhance reactivity of fillers, rheology modifiers, and surfactants.

Suitable preservatives may be selected from reducing agents such as vitamin C, inorganic sulfides and polysulfides and the like.

Particularly Preferred Embodiment

According to a particularly preferred embodiment, the dental composition according to the invention comprises (a) a homogeneous phase comprising monomer combinations (i) and (ii), (i) and (iii), (ii) and (iii), or (i), (ii) and (iii), or comprising monomer (iii), wherein (i) represents one or more compounds having one or more radically polymerizable carbon-carbon double bonds, preferably at least one of compounds of formulae (A), (B), (C), (D), (E), (F), (G) and (H), more preferably at least one of compounds of formulae (A), (B), (C), (D), (E) and (F), even more preferably at least one of compounds of formulae (B) and (E), yet even more preferably a compound of formula (B), and most preferably a compound of formula (B) selected from the group consisting of:

(ii) represents one or more compounds having one or more cationically polymerizable groups, preferably at least one of compounds of formulae (J), (K), (L), (M), (N), (O), more preferably at least one of compounds of formulae (J), (K) and (L) wherein Het is an oxygen atom and compounds of formulae (M), (N), (O) wherein Het$^{\#}$ and Het$^{\#\#\#}$ are oxygen atoms, even more preferably at least one of compounds of formulae (J) wherein A is a methylene group ($-CH_2-CH_2-$) and Het is an oxygen atom, compounds of (K) wherein A is a single bond and Het is an oxygen atom and compounds of formulae (M) and (N) wherein Het$^{\#}$ is an oxygen atom, $R^{34}$ is an ethylenglycol moiety of formula $-[-O-CH_2-CH_2-]_n-R^y$ with n=1 to 9 and $R^y$ being hydrogen or OH, and $R^{35}$ is an ethylenglycol moiety of formula $-[-O-CH_2-CH_2-]_n-$ with n=1 to 9, yet even more preferably compounds of formula (J) and (K) selected from the group consisting of:

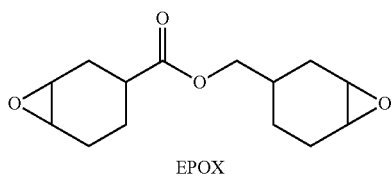

EPOX

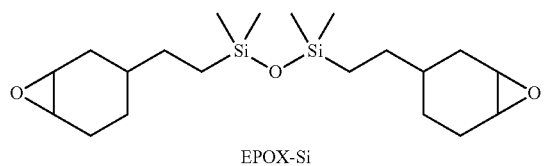

EPOX-Si

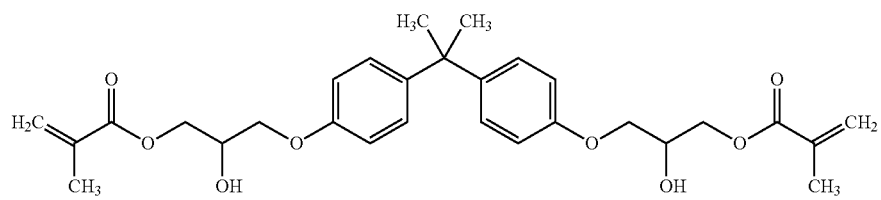

BisGMA

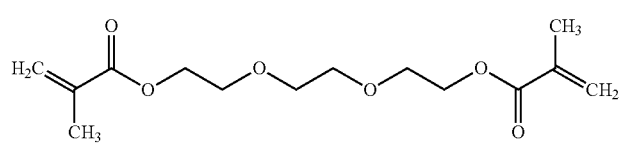

TEGDMA

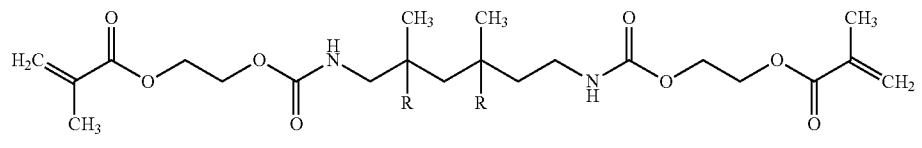

UDMA
R = H or CH$_3$(-1:1)

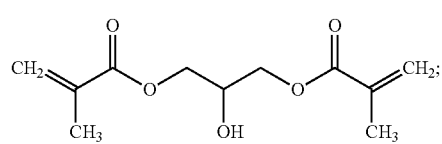

GDM

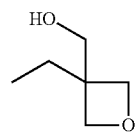

3-Hydroxymethyl-3-ethyl oxetane and most preferably EPOX or EPOX-Si;
(iii) represents one or more compounds having a combination of one or more radically polymerizable carbon-carbon double bonds and one or more cationically polymerizable groups, preferably at least one of compound of formula (P), most preferably 2-vinyloxyethoxyethyl methacrylate (VEEM) having the following structural formula:

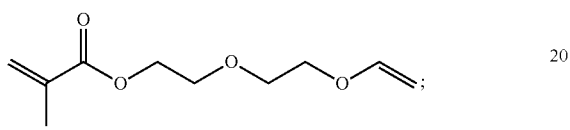

(b) an initiator system comprising
(iv) a radical polymerization initiator, which is a compound of the following formula (I):

wherein
M is Ge or Si;
$R^1$, $R^2$ and $R^3$ may be the same or different, and are independently selected from the group consisting of a straight chain or branched $C_{1-4}$ alkyl group, and a phenyl or benzoyl group optionally substituted with one substituent selected from the group consisting of a halogen atom, a nitro group, a $C_{1-4}$ alkoxy group and a —$NR^xR^y$ group wherein $R^x$ and $R^y$ independently from each other represent a $C_{1-4}$ alkyl group, and $R^4$ has the following formula (V):

wherein R (i) has the following formula (VI):

wherein M, $R^1$, $R^2$ and $R^3$ have the same meaning as defined for formula (I), whereby the compound of formula (I) may be symmetrical or unsymmetrical hydrocarbyl group; or (ii) is a group of the following formula (VII):

wherein
X represents a single bond, an oxygen atom or a group NR', wherein R' has the same meaning as $R^1$ and is selected independently therefrom;
R* has the same meaning as $R^1$ and is selected independently therefrom, a trihydrocarbylsilyl group, a mono(hydrocarbylcarbonyl)dihydrocarbylsilyl group or a di(hydrocarbylcarbonyl)monohydrocarbylsilyl group; or
(iii) when M is Si, R may be a substituted or unsubstituted hydrocarbyl group,
preferably R is (ii) a group of formula (VII),
more preferably R is (ii) a group of formula (VII) wherein X is an oxygen atom and R* has the same meaning as $R^1$ and is selected independently therefrom,
even more preferably compound of formula (I) is selected from the group consisting of

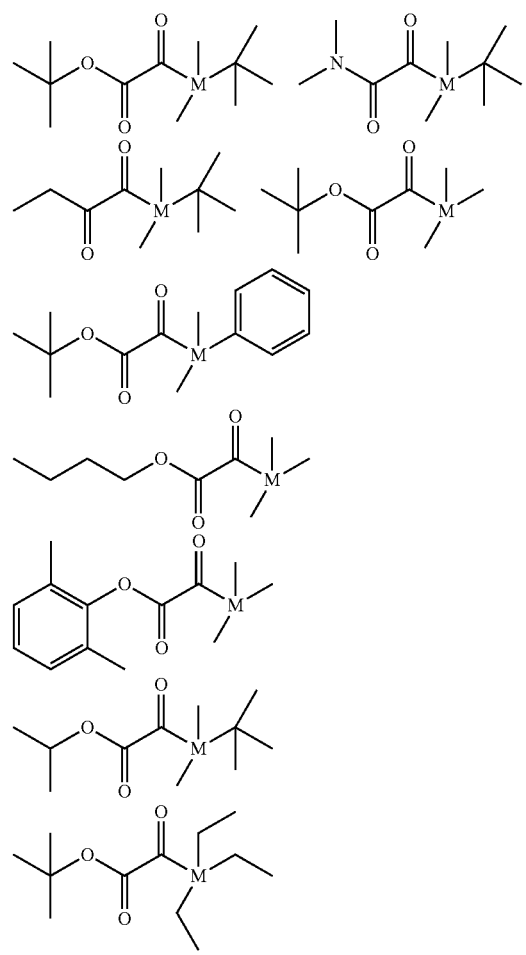

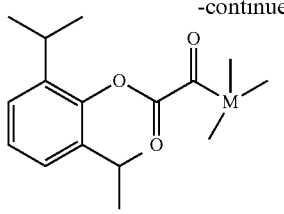

wherein M is preferably Si, and most preferably, compound of formula (I) is tert-butyl (tert-butyldimethylsilyl)glyoxylate) (DKSi);

(v) a cationic polymerization initiator which is selected from the compounds of formulae (II), (III) and (IV), wherein a compound of formula (II) is selected from the group consisting of (4-methylphenyl)[4-(2-methylpropyl) phenyl] iodonium hexafluoroantimonate, include (4-methylphenyl)[4-(2-methylpropyl) phenyl] iodonium tetrafluoroborate, diphenyliodonium (DPI) tetrafluoroborate, di(4-methylphenyl)iodonium (Me2-DPI) tetrafluoroborate, phenyl-4-methylphenyliodonium tetrafluoroborate, di(4-heptylphenyl)iodonium tetrafluoroborate, di(3-nitrophenyl) iodonium hexafluorophosphate, di(4-chlorophenyl) iodonium hexafluorophosphate, di(naphthyl) iodonium tetrafluoroborate, di(4-trifluoromethylphenyl)iodonium tetrafluoroborate, DPI hexafluorophosphate, Me2-DPI hexafluorophosphate; DPI hexafluoroarsenate, di(4-phenoxyphenyl)iodonium tetrafluoroborat, phenyl-2-thienyliodonium hexafluorophosphate, 3,5-dimethylpyrazolyl-4-phenyliodonium hexafluorophosphate, DPI hexafluoroantimonate, 2,2'-DPI tetrafluoroborate, di(2,4-dichlorophenyl)iodonium hexafluorophosphate, di(4-bromophenyl)iodonium hexafluorophosphate, di(4-methoxyphenyl)iodonium hexafluorophosphate, di(3-carboxyphenyl)iodonium hexafluorophosphate, di(3-methoxycarbonylphenyl)iodonium hexafluorophosphate, di(3-methoxysulfonylphenyl)iodonium hexafluorophosphate, di(4-acetamidophenyl)iodonium hexafluorophosphate, di(2-benzothienyl)iodonium hexafluorophosphate, and DPI hexafluorophosphate; more preferably, compound of formula (II) is selected from the group consisting of diphenyliodonium (DPI) hexafluorophosphate, di(4-methylphenyl)iodonium (Me2-DPI) hexafluorophosphate, diaryliodonium hexafluoroantimonate, (4-methylphenyl)[4-(2-methylpropyl) phenyl] iodonium hexafluoroantimonate, (4-methylphenyl)[4-(2-methylpropyl)phenyl]iodonium hexafluorophosphate (Irgacure® 250, commercial product available from BASF SE), (4-methylphenyl)[4-(2-methylpropyl) phenyl] iodonium tetrafluoroborate, 4-octyloxyphenyl phenyliodonium hexafluoroantimonate, 4-(2-hydroxytetradecyloxyphenyl)phenyliodonium hexafluoroantimonate, and 4-isopropyl-4'-methyldiphenyliodonium borate (PI 2074); most preferably, compound of formula (II) is DPI hexafluorophosphate and/or 4-isopropyl-4'-methyldiphenyliodonium tetrakis(pentafluorophenyl) borate (PI 2074);

compound of formula (III) is S-(phenyl)thianthrenium hexafluorophosphate of the following formula:

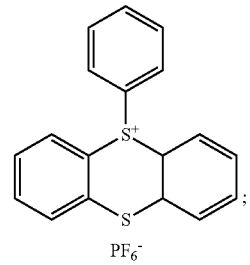

compound of formula (IV) is tetrakis-(hydroxymethyl)-phosphonium (THP) salt or a tetrakis-(hydroxymethyl)-phosphonium hydroxide (THPOH) salt, wherein the anion $A^-$ is selected from the group consisting of formate, acetate, phosphate, sulphate, fluoride, chloride, bromide and iodide;

preferably, the cationic polymerisation initiator is a compound of formula (II), most preferably DPI hexafluorophosphate and/or 4-isopropyl-4'-methyl-diphenyliodonium tetrakis(pentafluorophenyl) borate (PI 2074);

(vi) optionally the initiator system (b) further comprises at least one coinitiator selected from the group consisting of an amine compound, a compound having a Si—H or Ge—H bond, a carbazole compound, and a photoinitiator other than compounds of formulae (I) to (IV); preferably the coinitiator is selected from the group consisting of triethanolamine, 4-N,N-dimethylaminobenzonitrile, methyl N,N-dimethylaminobenzoate, ethyl N,N-dimethylaminobenzoate (EDB), N,N-dimethylaminoethyl methacrylate and isoamyl 4-N,N-dimethylaminobenzoate, N,N-dimethylaniline, N,N-dimethyltoluidine, N,N-diethanoltoluidine, dimethylaminoanisole, 1 or 2-dimethylaminonaphthalene, triphenylgermanium hydride ($Ph_3GeH$), tris(trimethylsilyl) silane ($(TMS)_3SiH$), 9H-carbazole-9-ethanol (CARET), and camphor quinone (CQ); more preferably the coinitiator is at least one selected from the group consisting of EDB, $Ph_3GeH$, $(TMS)_3SiH$, 2,4,6-tris(trichloromethyl)-1,3,5-triazine, CARET and CQ; most preferably, the coinitiator is $Ph_3GeH$, $(TMS)_3SiH$ or CARET, optionally in combination with CQ.

The invention will now be further illustrated by the following Examples.

EXAMPLES

Preparation Example 1: Preparation of Acylsilane Radical Polymerization Initiators General procedure for the preparation of acylsilanes.[1] A 10 mL screw-capped glass tube with a magnetic stir bar was charged with 0.054 g dichloro($\eta^3$-allyl)dipalladium(II) (0.3 mmol), 0.1 g Triethylphosphit (0.6 mmol) under $N_2$. Hexametyldisilane (0.96 g, 6.6 mmol) was added, and the mixture was stirred for 5 min at room temperature. After that, 6 mmol benzoylchloride was added slowly to the yellow solution. The reaction mixture was heated at 110° C. for 2.5 h. After cooling to room temperature, the reaction mixture was purified by column chromatography using the indicated eluent, without any preceding purification step.

[1] Yamamoto, K.; Suzuki, S.; Tsuji, J. Tetrahedron Lett. 1980, 21, 1653.

Preparation Example 1a:
Phenyl(trimethylsilyl)methanone

The title compound was prepared according to the general procedure using 0.84 g benzoylchloride (6 mmol), 0.054 g dichloro($\eta^3$-allyl)dipalladium(II) (0.3 mmol), 0.1 g Triethylphosphit (0.6 mmol) and 0.96 g Hexametyldisilane (6.6 mmol). The crude product was purified by column chromatography and received as clear yellow oil.

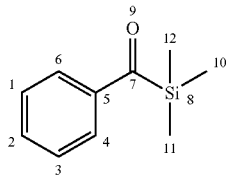

$^1$H-NMR [ppm]: (300 MHz, CDCl$_3$) δ 7.85-7.82 (m, 2H, Pos. 4, 6), δ 7.57-7.44 (m, 4H, Pos. 1, 2, 3), δ 0.38 (s, 9H, Pos. 10, 11, 12)

$^{13}$C-NMR [ppm]: (75 MHz, CDCl$_3$) δ 235.94 (Pos. 7); δ 141.48 (Pos. 5); δ 132.84 (Pos. 2); δ 128.80 (Pos. 4, 6); δ 127.63 (Pos. 1, 3); δ−1.21 (Pos. 10, 11, 12)

5.000 g (9.7656 mmol) 2,2-bis[4-[2-hydroxy-3-methacryloyloxypropoxy)phenyl]propane (Bis-GMA), 1.1983 g (4.1853 mmol) triethylene glycol dimethacrylate (TGDMA), 0.0497 g (0.2790 mmol) Benzoyl trimethylsilan (BTMS), 0.0999 g (0.6696) dimethylaniline and 0.0047 g (0.0212 mmol) 2,6-di-tert-butyl-p-cresol were mixed homogeneously. The polymerization enthalpy of this mixture is $\Delta_R$H=−56.5 kJ/mol, measured with the DSC 7 (Perkin-Elmer).

Preparation Example 1b:
4-Chlorophenyl(trimethylsilyl)methanone

The title compound was prepared according to the general procedure using 1.05 g 4-Chlorobenzoyl chloride (6 mmol), 0.054 g dichloro($\eta^3$-allyl)dipalladium(II) (0.3 mmol), 0.1 g Triethylphosphit (0.6 mmol) and 0.96 g Hexametyldisilan (6.6 mmol). The crude product was purified by column chromatography with ethyl acetate/n-Hexane (10:1) to afford 0.215 g (17%) of the acylsilane as clear yellow oil.

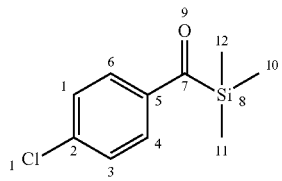

Element. anal.: theor. (C, 56.46%; H, 6.16%) pract. (C, 57.71%; H, 5.82%)

$^1$H-NMR [ppm]: (300 MHz, CDCl$_3$) δ 7.78-7.75 (m, 2H, Pos. 4, 6), δ 7.46-7.44 (m, 2H, Pos. 1, 3), δ 0.37 (s, 9H, Pos. 10, 11, 12)

$^{13}$C-NMR [ppm]: (75 MHz, CDCl$_3$) δ 234.44 (Pos. 7); δ 139.65 (Pos. 2); δ 139.19 (Pos. 5); δ 129.15 (Pos. 4, 6); δ 129.97 (Pos. 1, 3); δ−1.28 (Pos. 10, 11, 12) GC/MS: 212 [M$^+$]

Preparation Example 1c:
3-Chlorophenyl(trimethylsilyl)methanone

The title compound was prepared according to the general procedure using 1.05 g 3-Chlorobenzoyl chloride (3 mmol), 0.027 g dichloro($\eta^3$-allyl)dipalladium(II) (0.15 mmol), 0.05 g Triethylphosphit (0.3 mmol) and 0.48 g Hexametyldisilan (3.3 mmol). The crude product was purified by column chromatography with ethyl acetate/n-Hexane (10:1) to afford 0.220 (17%) of the acylsilane as clear yellow oil.

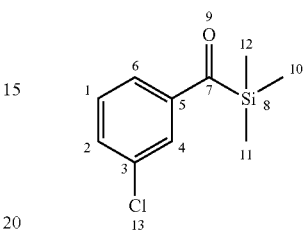

Element. anal.: theor. (C, 56.46%; H, 6.16%) pract. (C, 57.83%; H, 6.43%)

$^1$H-NMR [ppm]: (300 MHz, CDCl$_3$) δ 7.76-7.75 (m, 1H, Pos. 4), δ 7.73-7.69 (m, 1H, Pos. 2/6), δ 7.52-7.48 (m, 1H, Pos. 2/6); δ 7.44-7.39 (m, 1H, Pos. 1); δ 0.38 (s, 9H, Pos. 10, 11, 12)

$^{13}$C-NMR [ppm]: (75 MHz, CDCl$_3$) δ 234.30 (Pos. 7); δ 142.63 (Pos. 2); δ 144.82 (Pos. 5); δ 128.27 (Pos. 4, 6); δ 124.27 (Pos. 1, 3); δ−1.17 (Pos. 10, 11, 12) GC/MS: 212 [M$^+$]

Preparation Example 1d:
4-Nitrophenyl(trimethylsilyl)methanone

The title compound was prepared according to the general procedure using 0.56 g 4-Nitrobenzoyl chloride (3 mmol), 0.027 g dichloro($\eta^3$-allyl)dipalladium(II) (0.15 mmol), 0.05 g Triethylphosphit (0.3 mmol) and 0.48 g Hexametyldisilan (3.3 mmol). The crude product was purified by column chromatography with ethyl acetate/n-Hexane (10:1) to afford 0.13 g (19.5%) of the acylsilane as clear yellow oil.

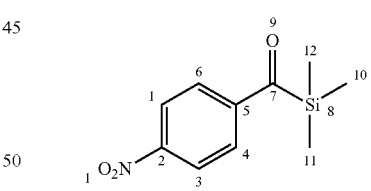

Element. anal.: theor. (C, 53.79%; H, 5.87%; N, 6.27) pract. (C, 52.84%; H, 5.75%; N, 6.29)

$^1$H-NMR [ppm]: (300 MHz, CDCl$_3$) δ 8.35-8.32 (m, 2H, Pos. 1, 3), δ 7.95-7.92 (m, 2H, Pos. 1, 3), δ 0.40 (s, 9H, Pos. 10, 11, 12)

$^{13}$C-NMR [ppm]: (75 MHz, CDCl$_3$) δ 235.38 (Pos. 7); δ 149.98 (Pos. 2); δ 144.82 (Pos. 5); δ 128.27 (Pos. 4, 6); δ 124.27 (Pos. 1, 3); δ−1.17 (Pos. 10, 11, 12) GC/MS: 223 [M$^+$]

Preparation Example 1e:
3-Nitrophenyl(trimethylsilyl)methanone

The title compound was prepared according to the general procedure using 0.56 g 4-Nitrobenzoyl chloride (3 mmol), 0.027 g dichloro(η³-allyl)dipalladium(II) (0.15 mmol), 0.05 g Triethylphosphit (0.3 mmol) and 0.48 g Hexametyldisilan (3.3 mmol). The crude product was purified by column chromatography with ethyl acetate/n-Hexane (10:1) to afford 0.3 g (22%) of the acylsilane as a yellow solid.

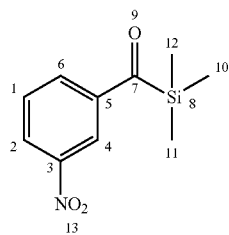

Element. anal.: theor. (C, 53.79%; H, 5.87%; N, 6.27) pract. (C, 52.73%; H, 5.77%; N, 6.31)

¹H-NMR [ppm]: (300 MHz, CDCl₃) δ 8.87-8.85 (m, 1H, Pos. 2), δ 8.41-8.37 (m, 1H, Pos. 4), δ 8.14-8.12 (m, 1H, Pos. 6); δ 7.71-7.66 (m, 1H, Pos. 1); δ 0.42 (s, 9H, Pos. 10, 11, 12)

¹³C-NMR [ppm]: (75 MHz, CDCl₃) δ 233.83 (Pos. 7); δ 148.72 (Pos. 3); δ 142.11 (Pos. 5); δ 132.70 (Pos. 6); δ 130.10 (Pos. 1); δ 126.97 (Pos. 2), δ 122.60 (Pos. 4), 65-1.44 (Pos. 10, 11, 12) GC/MS: 223 [M⁺]

Photopolymerisation Testing with Different Photoinitiator Systems:

Materials

Triphenylgermanium hydride (Ph₃GeH), tris(trimethylsilyl)silane (TMS)₃SiH), diphenyl iodonium (DPI, also called Ph₂I⁺ in some chemical reactions), hexafluorophosphate and camphor quinone (CQ) were obtained from Sigma-Aldrich. Bisphenol A-glycidyl methacrylate (Bis-GMA), triethyleneglycol dimethacrylate (TEGDMA), the urethane dimethacrylate 4,4,6,16 (or 4,6,6,16)-tetramethyl-10,15-dioxo-11,14-dioxa-2,9-diazaheptadec-16-enoicacid 2-[(2-methyl-1-oxo-2-propen-1-yl)oxy]ethyl ester (CAS no. 72869-86-4) (UDMA), 1,3-glycerol dimethacrylate (GDM) were also obtained from Sigma-Aldrich and used with the highest purity grade available. 9H-carbazole-9-ethanol (CARET) was obtained from ???.

The structural formulae of the compounds applied in the Examples are shown in Scheme 7 below:

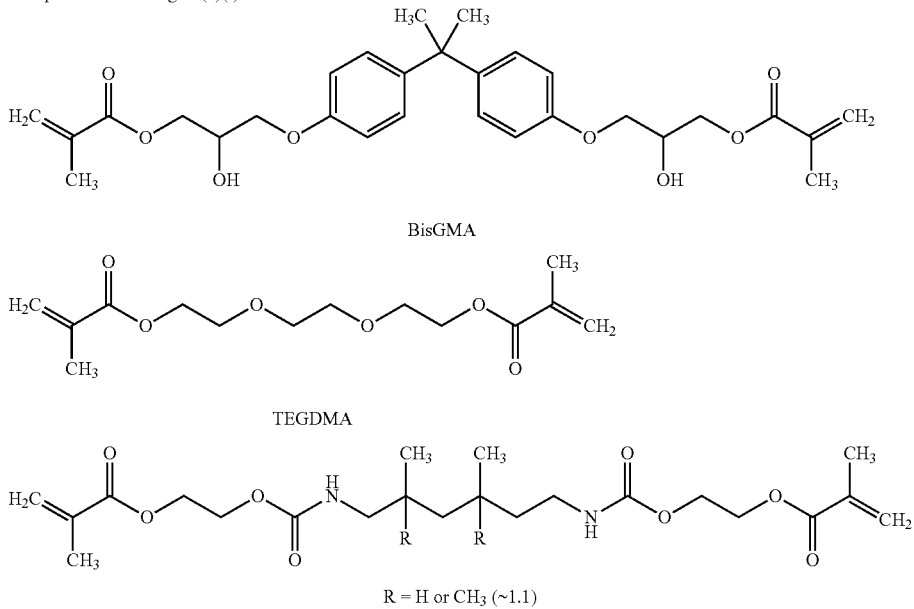

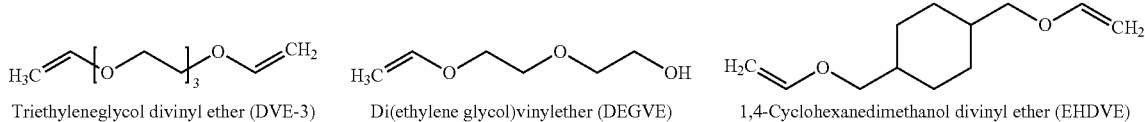

-continued
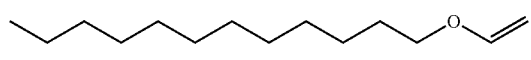
DODECYL VINYL ETHER
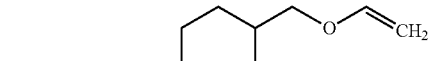
1,4-Cyclohexanedimethanol divinyl ether (EHDVE)
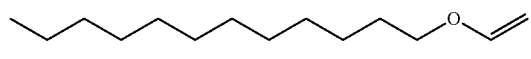
DODECYL VINYL ETHER
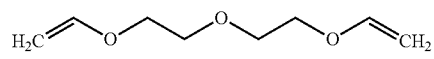
Di(ethylene glycol) divinylether (DEGDVE)
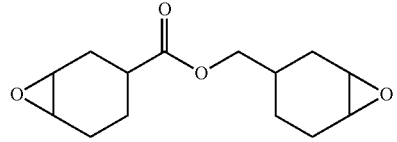
EPOX
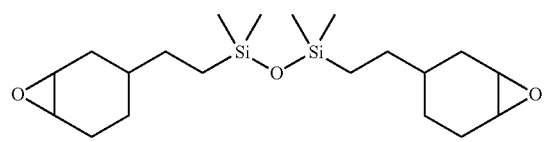
EPOX-Si
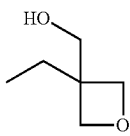
3-Hydromethyl-3-ethyl oxetane
compound according to (a)(iii)
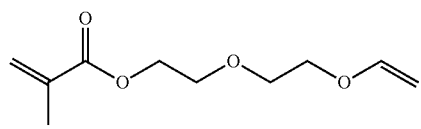
2-Vintloxyethoxyethyl methacrylate (VEEM)
compound according to (b)(iv)
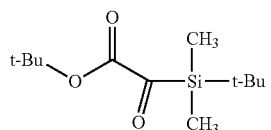
DKSi
compound according to (b)(v)
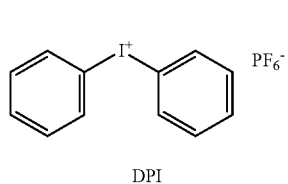
DPI
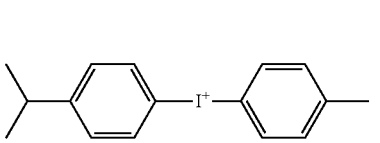
PI 2074
compound according to (b)(vi)
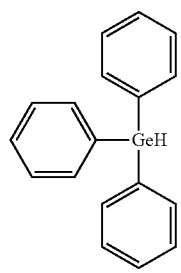
Ph₃GeH
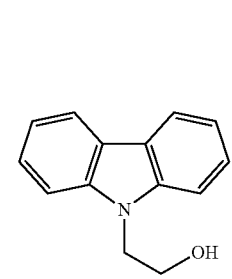
CARET Radical polymerization initator in the Reference Examples

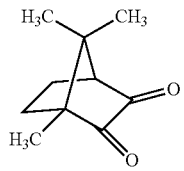

Camphor quinone (CQ)

Irradiation Source

Figure 1:
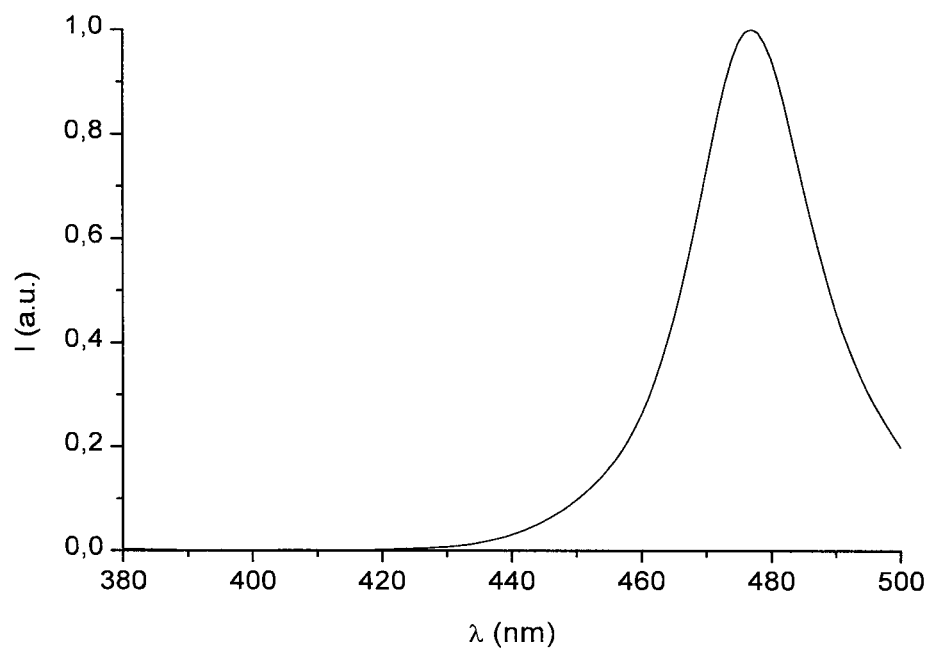
FIG. 1 shows the emission spectrum of the radiation source used for the irradiation of the photocurable samples of the Examples, which is a blue dental LED centred at 477 nm (SmartLite® Focus from Dentsply De-Trey Germany, about 80 mW/cm²). Unless indicated otherwise, the blue dental LED was applied with a power of about 80 mW/cm². The abbreviation "I" stands for "intensity", and the abbreviation "a.u." for "arbitrary unit".

A dental blue LED centered at 477 nm (Dentsply SmartLite Focus; ~80 mW cm$^{-2}$ at the surface of the irradiated sample) was used for the irradiation of the samples. The emission spectrum of Dentsply SmartLite Focus is given in FIG. 1.

Photopolymerization Experiments:

The photosensitive formulations were deposited on a BaF$_2$ pellet under air or in laminate (25 μm thick) for irradiation with the LED light. The evolution of the double bond content of Bis-GMA, TEGDMA or UDMA was continuously followed by real time FTIR spectroscopy (JASCO FTIR 4100) at about 1630 cm$^{-1}$. The evolution of the Ge—H content in the Ph$_3$GeH based formulations can be also followed at 2030 cm$^{-1}$.

For thick samples (1.4 mm), the polymerization was evaluated under air in the near infrared range following the band at 6160 cm$^{-1}$ and the procedure presented just above.

For compounds/monomers having the cationically polymerizable group(s) epoxy and oxetane, polymerization was followed at 790 cm$^{-1}$ and 880 cm$^{-1}$, respectively; the polymerization of vinylether groups was followed at 1618 cm$^{-1}$ for thin samples of about 20 μm, and at 6190 cm-1 for thick samples of about 1.4 mm).

Figure 2:
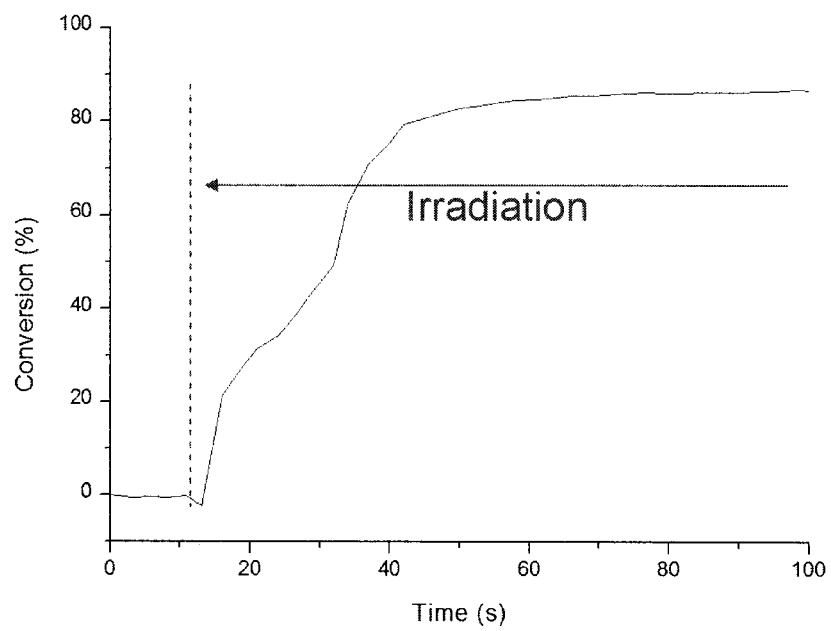
FIG. 2 shows the photopolymerization profile of triethyleneglycol divinyl ether (DVE-3) polymerized in samples of 25 μm thickness in laminate in the presence of the initiator system camphor quinone (CQ)/triphenylgermanium hydride (Ph₃GeH)/diphenyl iodonium hexafluorophosphate (DPI) (1%/1.5%/1.5% w/w) upon the exposure to dental LED at 477 nm (SmartLite® Focus). As indicated in FIG. 2 by the dotted line, the irradiation starts at t=12 s.
Figure 3:
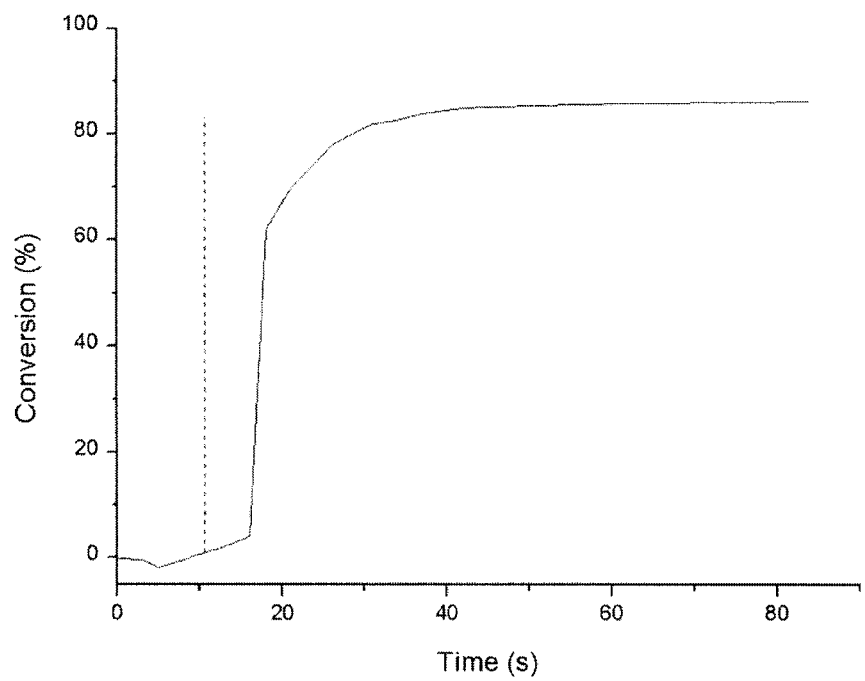
FIG. 3 shows the photopolymerization profile of DVE-3 polymerized in samples of 25 μm thickness in laminate in presence of the initiators system tert-butyl (tert-butyldimethylsilyl)glyoxylate) (DKSi)/DPI (2%/1% w/w) upon the exposure to dental LED at 477 nm (SmartLite® Focus). As indicated in FIG. 3 by the dotted line, the irradiation starts at t=12 s.

Comparative Example 1: Cationic Polymerization of Vinylethers, Epoxys and Oxetanes in the Presence of the Initiator Systems DKSi/DPI, DKSi/Ph$_3$GeH/DPI, CQ/Ph$_3$GeH/DPI, CQ/DPI, CARET/DPI and CQ/CARET/DPI The initiator systems DKSi/DPI and CQ/Ph$_3$GeH/DPI were found very efficient to initiate the cationic polymerization of DVE-3, as can be gathered from FIGS. 2 and 3) with high final conversions (>80%) upon a SmartLight Focus LED. Tack free polymers were obtained. As DVE-3 is not able to homopolymerize by radical polymerization, the excellent polymerization profiles obtained here clearly show that the new proposed systems are excellent to initiate the cationic polymerization of DVE-3.

Figure 4A:
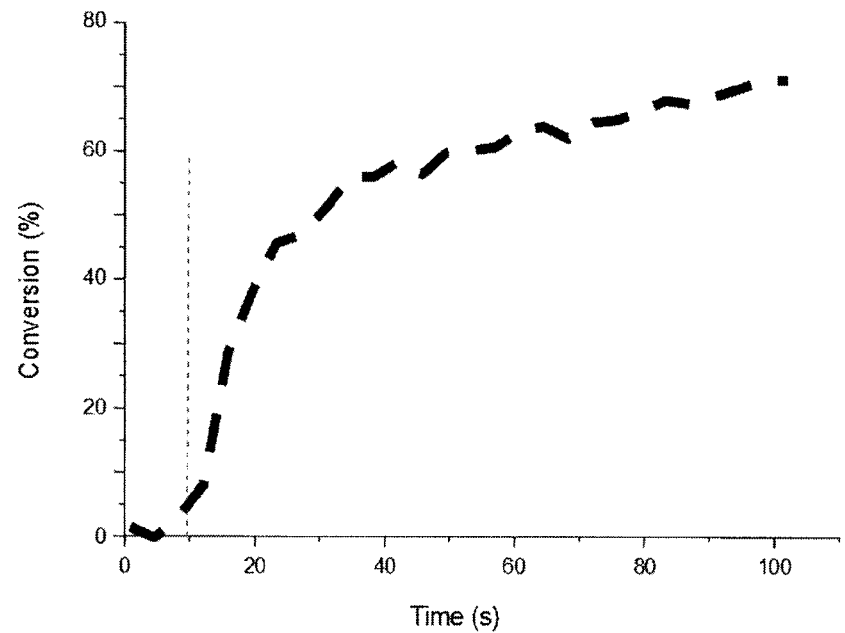
FIG. 4A shows the photopolymerization profile of 7-oxabicyclo[4.1.0]hept-3-ylmethyl 7-oxabicyclo[4.1.0]heptane-3-carboxylate (EPOX) polymerized in samples of 25 µm thickness under air in presence of the initiators system CQ/Ph$_3$GeH/DPI (2%/1.5%/1.5% w/w upon the exposure to dental LED at 477 nm (SmartLite® Focus). As indicated in FIG. 4A by the dotted line, the irradiation starts at t=10 s.
Figure 4B:
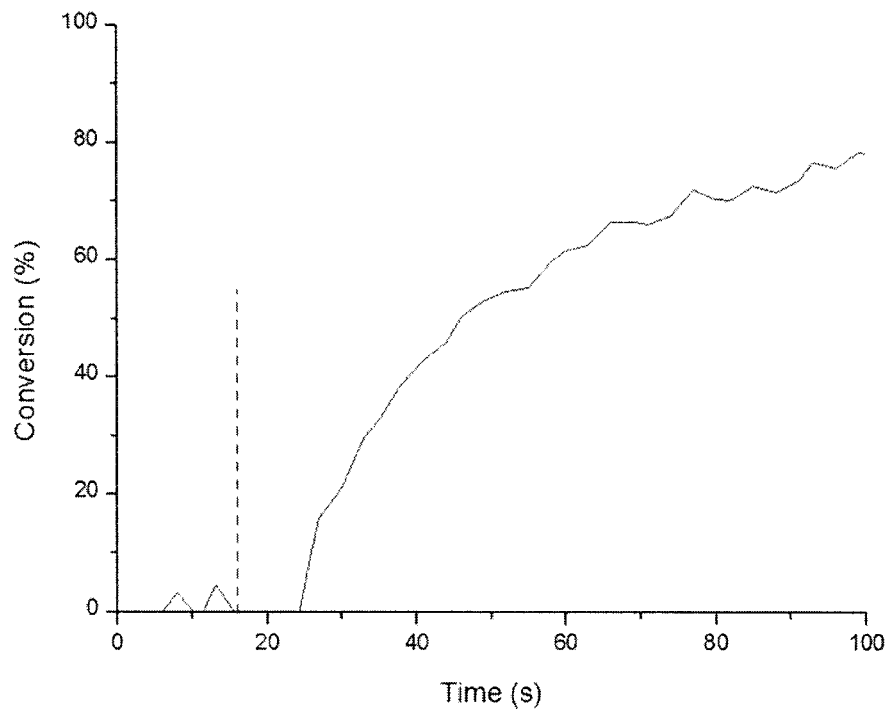
FIG. 4B shows the photopolymerization profile of 1,1,3,3-tetramethyl-1,3-bis[2-(7-oxabicyclo[4.1.0] hept-3-yl) ethyl] disiloxane (EPOX-Si) polymerized in samples of 25 µm thickness under air in presence of the initiators system DKSi/4-Isopropyl-4'-methyldiphenyliodonium tetrakis(pentafluorophenyl) borate (PI2074) (2%/2% w/w) upon the exposure to dental LED at 477 nm (SmartLite® Focus, 300 mW/cm$^2$). As indicated in FIG. 4B by the dotted line, the irradiation starts at t=10 s.
Figure 4C:
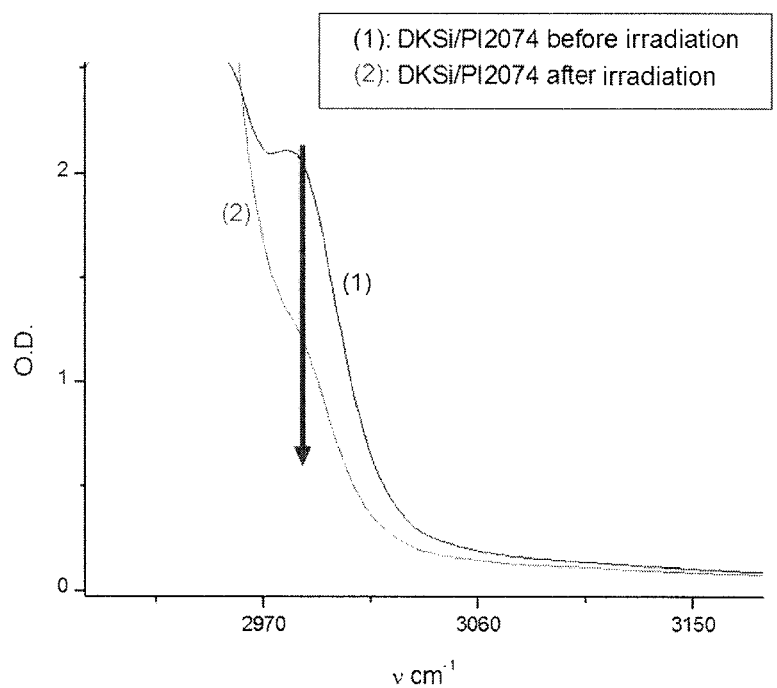
FIG. 4C shows an IR spectrum section of the sample of FIG. 4B within the wavelength range of about 2880 to 3150 cm$^{-1}$ before and after irradiation. The arrow in FIG. 4C indicates the peak at about 2980 cm$^{-1}$ for monitoring conversion of the epoxy functions of EPOX-Si.
Figure 5:
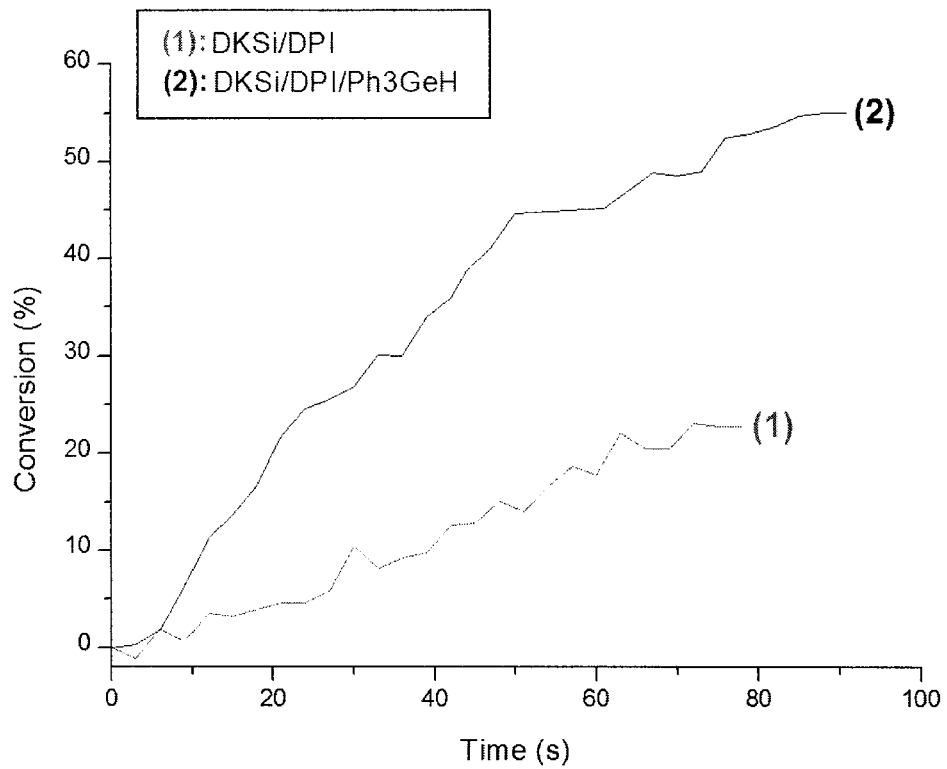
FIG. 5 shows the photopolymerization profile of EPOX polymerized in samples of 25 µm thickness under air upon the exposure to dental LED at 477 nm (SmartLite® Focus) for the following different initiator systems:
Curve (1): DKSi/DPI (1%/1% w/w)
curve (2): DKSi/Ph$_3$GeH/DPI (1%/1%/1% w/w).
As indicated in FIG. 5 by the dotted line, irradiation starts at t=10 s.

The initiator systems DKSi/Ph$_3$GeH/DPI, CQ/Ph$_3$GeH/DPI and DKSi/PI2074 were also found very efficient to initiate the cationic polymerization of epoxy monomer EPOX, as can be gathered from FIGS. 4 A to C and FIG. 5 with high final conversions (>60%) upon a SmartLight Focus LED and under air. The presence of Ph$_3$GeH can also improve the polymerization efficiency, as can be gathered from FIG. 5 when comparing curves (1) and (2). However, as can be gathered from FIG. 4B, for EPOX-Si, addition of Ph$_3$GeH appears to be not necessary for improvement of conversion, since the initiator system DKSi/PI2074 is already a very good initiator system for EPOX-Si, as confirmed by FIG. 4B.

Further, the initiator system CQ/CARET/DPI was tested with 2%/1.2%/1.5% w/w and 2%/2.4%/1.5% w/w. As can be gathered from FIG. 16, this initiator system turned out to be very efficient to initiate the cationic polymerization of the epoxy monomer EPOX, while the initiator systems CQ/DPI and CARET/DPI provided relatively poor conversions of epoxy functions of only about 5 to 15%.

In conclusion, Comparative Example 1 shows that the polymerization of epoxy-, epoxy-silicone- and vinylether— functions can be readily initiated in presence of an initiator system having different contents of tert-butyl (tert-butyldimethylsilyl)glyoxylate) (DKSi)/diphenyl iodonium hexafluorophosphate (DPI). Excellent final conversions are reached both under air and in laminate for samples of different thicknesses (20 μm to 1.4 mm) upon irradiation with a dental LED ($v_{max}$=480 nm, SmartLite Focus Dentsply DeTrey Germany).

Besides of the initiators systems DKSi/DPI and DKSi/Ph$_3$GeH/DPI tested for their suitability to initiate polymerization of vinylether- and epoxy(-Si)-functions, further tests were carried out with other initiators systems for their suitability to initiate not only vinylether- and epoxy(Si)-functions, but also oxetane functions. As a model compound for testing polymerization of oxetane functions, the compound 3-hydroxymethyl-3-ethyl oxetane was applied.

The global performances of the tested initiator system are summarized in Table 1 below.

TABLE 1

Initiator systems for cationic polymerization upon visible light (blue light) irradiation; After 60 s, monomer conversions upon exposure to dental blue LED centered at 477 nm (SmartLite Focus) reached >50%.

| | cationic polymerization of: | | |
|---|---|---|---|
| Initiator systems | epoxy-functions | vinylether-functions | oxetane-functions |
| CQ/DPI* | No | No | No |
| CQ/Ph$_3$GeH (or (TMS)$_3$SiH)/DPI (or PI2074)*[)] | Yes | Yes***[)] | No |
| DKSi/DPI*[)] | No | Yes | No |
| DKSi/PI2074*[)] | Yes | Yes | n.d.[#)] |
| DKSi/Ph$_3$GeH (or (TMS)$_3$SiH)/DPI (or PI2074)*[)] | Yes | Yes | Yes |
| CQ/CARET/DPI**[)] | Yes | n.d.[#)] | n.d.[#)] |

*[)]Quantitative compositions of initiator systems: DKSi or CQ: 0.5% w/w; Ph$_3$GeH or (TMS)$_3$SiH): 2% w/w; and DPI: 2% w/w.
**[)]Quantitative compositions of initiator system: 2%/1.2%/1.5% w/w and 2%/2.4%/1.5% w/w
***[)]>80% conversion with CQ/Ph$_3$GeH/DPI
[#)]"n.d." means "not determined"

The bleaching properties for all examples of Comparative Example 1 wherein cationic polymerization occurred were always found excellent.

Examples 1 to 11 and Reference Examples: Hybrid Polymerizations

In the following Examples 1 to 11 and Reference Examples, hybrid polymerization of a homogeneous phase (a) comprising monomer combinations (i) and (ii), (i) and (iii), or (i), (ii) and (iii) of the dental composition according to claim 1 were tested in the presence of different initiator systems (b).

A camphor quinone (CQ) based initiator system was also used. The CQ based systems required the presence of iodonium salt and germanium hydride ($R_3$GeH) or a silane ($R_3$SiH), i.e. the reference systems were CQ/$R_3$GeH/DPI or CQ/$R_3$SiH/DPI.

The results of the testing of Examples 1 to 11 and of further Examples carried out are summarized in advance in Table 2.

The bleaching properties for all examples of Examples 1 to 11 wherein hybrid polymerization occurred were always found excellent.

Figure 6:
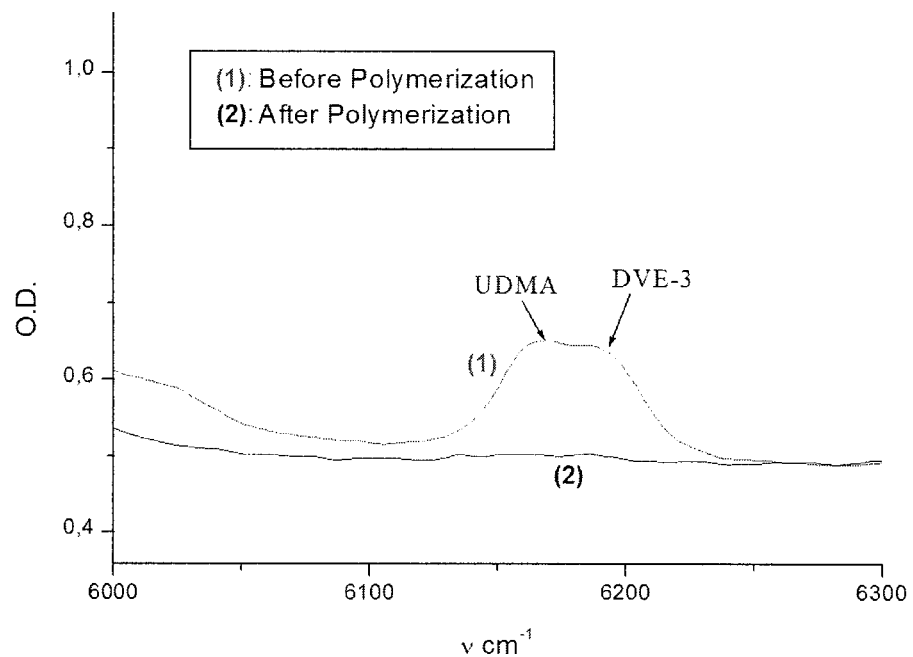
FIG. 6 shows IR spectra of a 4,4,6,16 (or 4,6,6,16)-tetramethyl-10,15-dioxo-11,14-dioxa-2,9-diazaheptadec-16-enoicacid 2-[(2-methyl-1-oxo-2-propen-1-yl)oxy]ethyl ester (CAS no. 72869-86-4) (UDMA)/DVE-3 blend (60%/40% w/w) polymerized in samples of 1.4 mm thickness under air before and after the photopolymerization in the presence of the initiator system DKSi/DPI (2%/1% w/w) upon the exposure to dental LED at 477 nm (SmartLite® Focus, 300 mW/cm$^2$). The IR spectrum after photopolymerisation shows a full conversion of the methacrylate and vinylether functions after polymerization. The abbreviation "O.D." used for indication of the ordinate means "optical density". This abbreviation is used with the same meaning in FIGS. 7, 11 A to C, 13 B/C and 14A.

Example 1: DKSi/DPI for the Hybrid Polymerization of Methacrylate/Vinylether Blends The DKSi/DPI system was able to initiate both radical and cationic polymerizations, and therefore it was used for the synthesis of interpenetrating polymer networks (IPNs) through the polymerization of a compound having radically polymerizable groups (e.g. methacrylate)/compound having cationically polymerizable group(s) (e.g. vinylether) blend. Examples are provided here with the polymerization of a UDMA/DVE-3 blend shown in FIG. 6, BisGMA/DVE-3 blend shown in FIGS. 7 and 8 and UDMA/DEGDVE (or DEGVE or DVE-3) upon 300 mW/cm$^2$ shown in FIG. 9.

TABLE 2

Initiator systems for hybrid polymerization, i.e. radicalic and cationic polymerization, upon the exposure to visible blue light of a dental blue LED centerd at 477 nm (Dentsply SmartLite Focus); After 60 s, monomer conversions upon exposure to dental blue LED centered at 477 nm (SmartLite Focus) reached >50%.

| | Hybrid polymerization of: | | | |
|---|---|---|---|---|
| Initiator system | methacrylate/ epoxy blend | methacrylate/ vinylether blend | methacrylate/ vinylether/ epoxy blend | blend of methacrylate/ (optionally vinylether)/ compound having methacrylate and vinylether group |
| CQ/DPI*[)] (Comparative Examples) | No | No | n.d.[#)] | No |
| CQ/Ph$_3$GeH (or (TMS)$_3$SiH)/ DPI (or PI2074)*[)] | Yes (cf. Ref. Ex. 3, 5 & 10)[##)] | Yes (cf. Comparative Ex. 1)[##)] | n.d.[#)] | n.d.[#)] |
| CQ/CARET/ PI2074**[)] | Yes (cf. Ref. Ex. 1)[##)] | n.d.[#)] | n.d.[#)] | n.d.[#)] |
| DKSi/DPI*[)] | Yes | Yes (cf. Ex. 1&6)[##)] | n.d.[#)] | Yes (cf. Ex. 7)[##)] |
| DKSi/PI2074*[)] | Yes | Yes (cf. Ex. 4)[##)] | Yes (cf. Ex. 8)[##)] | Yes (cf. Ex. 9 and 11)[##)] |
| DKSi/Ph$_3$GeH (or (TMS)$_3$SiH)/DPI (or PI2074)*[)] | Yes | Yes (cf. Ex. 2)[##)] | n.d.[#)] | n.d.[#)] |
| DKSi/PI2074/ CARET***[)] | n.d.[#)] | n.d.[#)] | n.d.[#)] | Yes (cf. Ex. 11)[##)] |

*[)]Quantitative composition of the initiator systems: DKSi or CQ: 0.5% w/w; Ph$_3$GeH or (TMS)$_3$SiH): 2% w/w; DPI: 2% w/w
**[)]Quantitative composition of the initiator system: 2%/2%/2% w/w
***[)]Quantitative composition of the initiator system: 1.2%/1.1%/1% w/w
[)]"n.d." means "not determined"
[)]"Ex." means "Example", "Ref. Ex." means "Reference Example"

From Table 2 it can be gathered that a smoot hybrid polymerization resulting in a desirable interpenentrating polymer network (IPN) was attained in Examples 1 to 11, and the further tested Examples. By contrast, the cationic polymerization tested in Comparative Example 1 and summarized in Table 1 did not satisfactorily polymerize. These results confirm that owing to the combination of the homogeneous phase (a) and the initiator system (b) according to the invention, a synergistic effect is attained in that compounds having cationically polymerizable groups which normally do not (sufficiently) polymerize with the indicated initiator system, surprisingly polymerize smoothly in combination with the compounds of formula (i) having one or more radically polymerizable carbon-carbon double bond.

Figure 7:
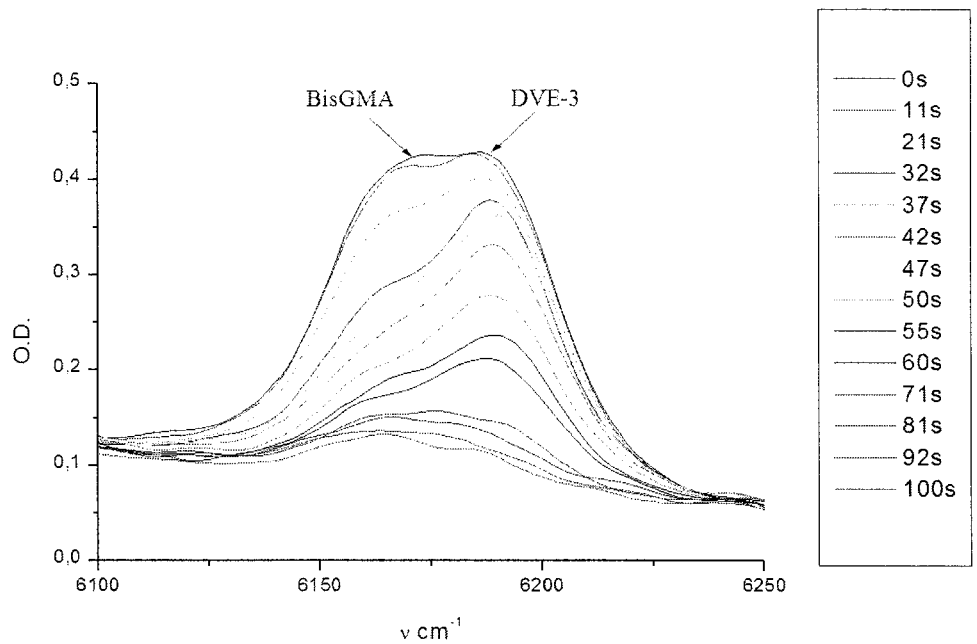
FIG. 7 shows IR spectra recorded during the photopolymerization of a (BisGMA)/DVE-3 blend (50%/50% w/w) in samples of 1.4 mm thickness under air in the presence of the initiator system DKSi/DPI (2%/1.5% w/w) upon the exposure to dental LED at 477 nm (SmartLite® Focus). In the box to the right of the IR spectra, the polymerization times for the uppermost to the lowermost spectrum are indicated in order of appearance. That is, the uppermost spectrum is obtained at the polmyerisation time of 0 s, and the lowermost spectrum is obtained after a polymerization time of 100 s. The IR spectra show a full conversion of the methacrylate and vinylether functions after polymerization.
Figure 8:
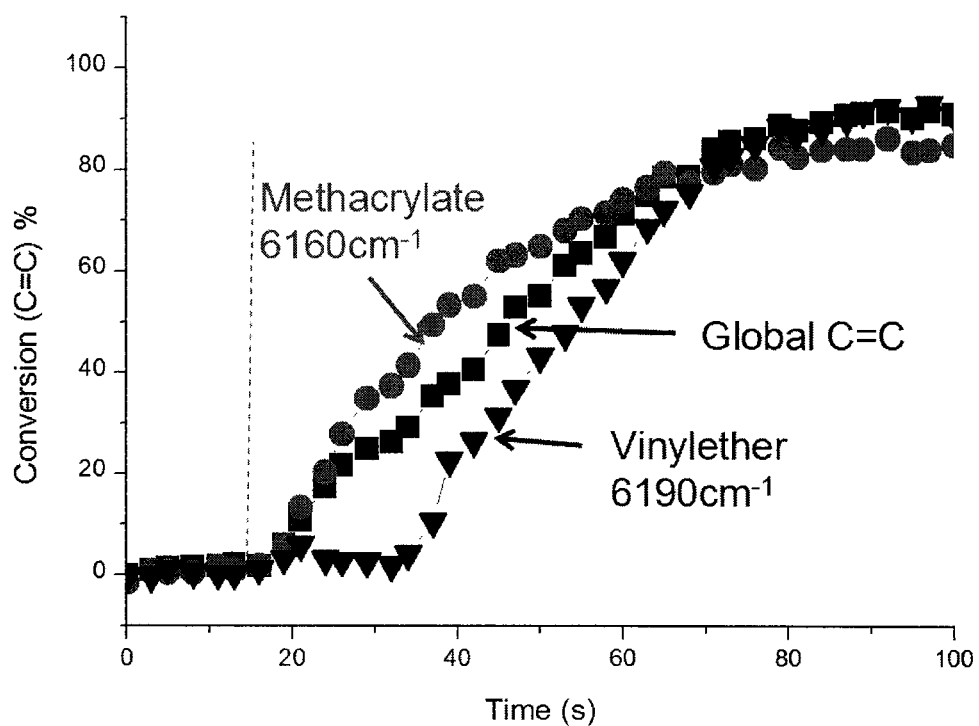
FIG. 8 shows photopolymerization profiles for a BisGMA/DVE-3 blend (50%/50% w/w) polymerized in samples of 1.4 mm under air in the presence of the initiator system DKSi/DPI (2%/1.5% w/w) upon the exposure to dental LED at 477 nm (SmartLite® Focus).
Figure 9A:
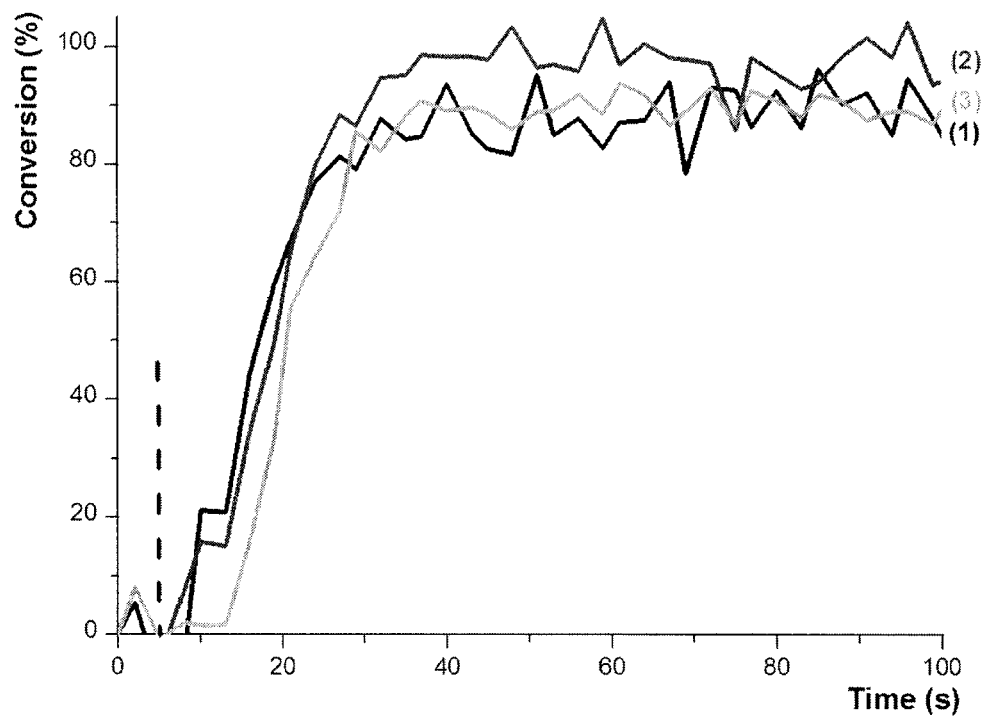
FIGS. 9A, 9B and 9C show photopolymerization profiles of the methacrylate functions (cf.
Figure 9B:
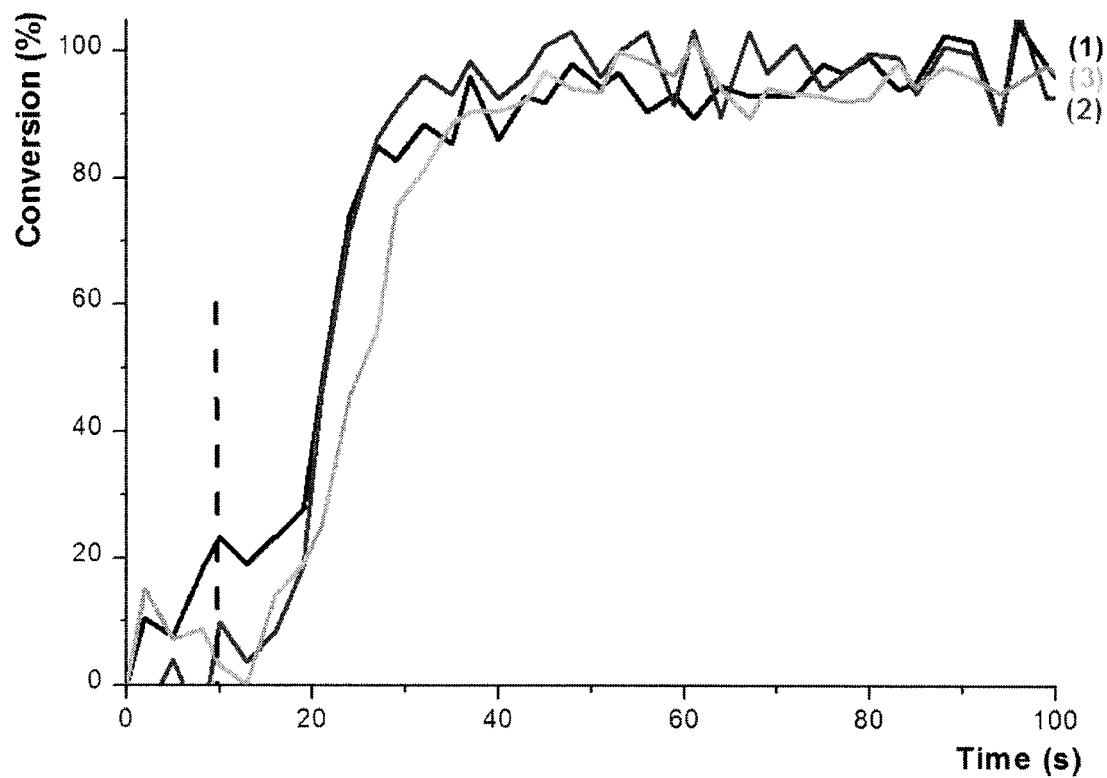
Figure 9C:
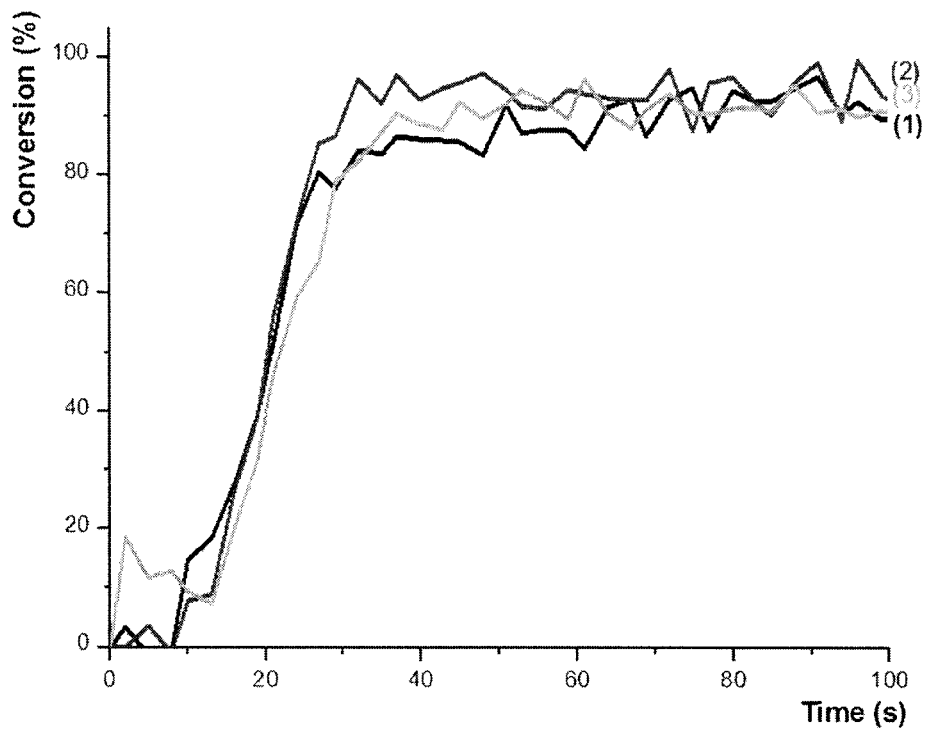

Remarkably, the polymerization was found to be rather sequential, that is, the radical polymerization started first, and the cationic polymerization started only after an inhibition period, as can be gathered from FIGS. 7 and 8. For high light intensity (300 mW/cm$^2$; FIG. 9), this sequential polymerization was not obvious, but extremely high methacrylate and vinylether conversions were still obtained (>90%). This appears to be a unique way to improve the global C=C conversion in dental materials.

In particular, it was surprisingly found that very high final conversions for both methacrylate and vinylether functions were reached, which were much more better than for pure methacrylate resins. This can be gathered from Table 3:

TABLE 3

Methacrylate final conversions in different matrix: polymerization of pure methacrylates (UDMA or BisGMA) versus a methacrylate/vinylether blend (UDMA/DVE-3 or BisGMA/DVE-3) in the presence initiator system DKSi/DPI (2%/1.5% w/w) upon the exposure to the dental blue LED centered at 477 nm (SmartLite Focus).

| Initiator system | UDMA | UDMA/DVE-3 (60%/40%) | BisGMA | BisGMA/DVE-3 (50/50%) |
|---|---|---|---|---|
| DKSi/DPI (2%/1.5% w/w) | 72 | ~100 | 65 | 92 |

Example 2 and Comparative Example 2: DKSi/(TMS)$_3$SiH (or Ph$_3$GeH)/DPI and Reference Initiator System CQ/(TMS)$_3$SiH (or Ph$_3$GeH)/DPI for the Hybrid Polymerization of Methacrylate/Vinylether Blends In presence of hydrogen donors in the form of silane or germanium hydride such as (TMS)$_3$SiH or Ph$_3$GeH, the kinetics of the hybrid polymerization of methacrylate/vinylether blends were improved. The required irradiation times to reach a conversion >70% are listed in Table 4.

TABLE 4

Irradiation times to reach a conversion of 70% (for the global methacrylate and vinylether functions); BisGMA/DVE-3 (50%/50% w/w); sample thickness = 1.4 mm; polymerization under air; exposure to dental blue LED centered at 477 nm (SmartLite Focus; 80 mW/cm$^2$.

| Initiating system | Time (s) |
|---|---|
| DKSi/DPI (2%/1.5% w/w) | 40 |
| DKSi/DPI/Ph$_3$GeH (2%/1%/1.5% w/w) | 35 |
| DKSi/DPI/(TMS)$_3$SiH (2%/1%/1.5% w/w) | 35 |
| CQ/DPI (2%/2% w/w) (comparative example 2) | >100 |
| CQ/DPI/Ph$_3$GeH (2%/2%/2% w/w) | 45 |
| CQ/DPI/(TMS)$_3$SiH (2%/2%/2% w/w) | 50 |

From Table 4 it can be gathered that by adding silane or germanium hydrides as H-donors, the required irradiation time to reach a high conversion was significantly decreased. Further, the results listed in Table 4 show that the presence of (TMS)$_3$SiH or Ph$_3$GeH provides for a significantly improved curing efficiency for both the inventive DKSi based initiator systems and the CQ based reference initiator systems. Further, Table 4 shows that the curing efficiency of the inventive DKSi based initiator systems is significantly improved compared to the CQ based reference initiator systems.

Example 3: CQ/pH$_3$GeH/DPI for the Hybrid Polymerization of BisGMA/TEGDMA/EPOX Blends The CQ/Ph$_3$GeH/DPI system was able to initiate both radical and cationic polymerizations and used for the synthesis of interpenetrating polymer networks (IPNs) through the polymerization of a blend of compound(s) having radically polymerizable group(s) and compound having cationically polymerizable group(s). Exemplary, the polymerization of a BisGMA/TEGDMA/EPOX blend was tested, and the results are shown in FIGS. 10 to 12.

The polymerization of the BisGMA/TEGDMA/EPOX blend was found to be sequential, i.e. the radical polymerization starts first, and the cationic polymerization starts only after an inhibition period. A clear conversion of the epoxy group was found, as can be gathered from FIG. 10. The monitoring of the conversion of the functional groups before and after polymerization in thin samples of about 20 µm by means of IR spectroscopy is shown for the epoxy functions in FIG. 11A, for the methacrylate functions in FIG. 11B and for the Ge hydride functions in FIG. 11C.

For thick samples of about 1.4 mm of the BisGMA/TEGDMA/EPOX blend, very high final conversion rates for the methacrylate function (>90%) were reached, as can be gathered from FIG. 12A. The monitoring of the conversion of the methacrylate groups before and after polymerization in these thick samples by means of IR spectroscopy is shown for the methacrylate functions in FIG. 12B.

These conversion rates attained for thin and thick samples of the BisGMA/TEGDMA/EPOX blend of Reference Example 1 are much more higher than for pure methacrylate resins, for which conversion rate is only about 70%, as can be gathered from Table 3 above.

Example 4 and Example 5: DKSi/PI2074 and Reference Initiator System CQ/Ph$_3$GeH/DPI (or P12074) for the Hybrid Polymerization of Methacrylate/EPOX-Si Blends DKSi/PI2074 was found to represent an efficient initiating systems for the hybrid polymerization of methacrylate/EPOX-Si blends, as can be gathered from Table 2 above. Further, the reference initiator system CQ/Ph$_3$GeH/DPI (or P12074) was tested The results for the reference initiator system CQ/Ph$_3$GeH/DPI (or P12074) are shown in FIGS. 13 A, B and C. After 50-90 s upon irradiation with SmartLite Focus, almost full conversion of the methacrylate functions was obtained, but only about 20 to 30% of the epoxy groups of EPOX-Si were converted, as can be gathered from FIG. 13A.

Remarkably, in the polymer obtained in FIG. 12, upon storage, dark polymerization occurs. Thereby, the conversion of epoxy increases upon storage and reaches ~40 to 50% after about 1 to 6 days, as can be gathered from FIG. 14B.

This hybrid polymerization appears to be useful to increase the methacrylate conversion, since conversions >90% were obtained compared to 60-70% for pure UDMA, as can be gathered from Table 3 above.

Comparative Example 2: CQ/DMABE for the Polymerization of the Methacrylate UDMA 2.0000 g (4.2503 mmol) 4,4,6,16 (or 4,6,6,16)-Tetramethyl-10,15-dioxo-11,14-dioxa-2,9-diazaheptadec-16-enoicacid 2-[(2-methyl-1-oxo-2-propen-1-yl)oxy]ethyl ester (CAS no. 72869-86-4) (UDMA), 0.0071 g (0.0425 mmol) camphor quinone (CQ), 0.0099 g (0.051 mmol) 4-(dimethylamino) benzoic acid ethylester (DMABE) and 0.0017 g (0.0079 mmol) 2,6-di-tert-butyl-p-cresol were mixed homogeneously. The polymerization enthalpy measured with the DSC 7 (Perkin Elmer) was $\Delta_R H = -52.1 \pm 1.5$ kJ/mol (cf. FIG. 15).

Example 6: DKSI/DPI for the Hybrid Polymerization of the Methacrylate/Divinylether Blend UDMA/GDM/DEGDVE 6.0000 g (12.7508 mmol) 11,14-Dioxa-2,9-diazaheptadec-16-enoicacid, 4,4,6,16 (or 4,6,6,16)-tetramethyl-10,15-dioxo-,2-[(2-methyl-1-oxo-2-propen-1-yl)oxy]ethyl ester (UDMA), 1.50 g (6.5717 mmol) Glycerine dimethacrylate (GDM), 4.00 g (25.2845 mmol) Diethyleneglycol divinylether (DEGDVE), 0.1413 g (0.5781 mmol) tert-Butyl (tert-butyldimethylsilyl) glyoxylate (DKSi) and 0.1410 g (0.3309 mmol) diphenyliodonium hexafluoro phosphate (DPI) were mixed homogeneously. The polymerization enthalpy measured with the DSC 7 (Perkin Elmer) was $\Delta_R H=-45.1\pm0.9$ kJ/mol, as can be gathered from FIG. 15.

FIG. 15 shows that the photo polymerization according to Example 6 shows a strong delay of free-radical and cationic polymerization compared to the free-radical polymerization of Comparative Example 2.

Example 7: DKSi/DPI for the Hybrid Polymerization of the Methacrylate/Compound Having Radically Polymerizable Methacrylate and Cationically Polymerizable Divinylether Group Blend UDMA/VEEM 7.5000 g (15.9385 mmol) 11,14-Dioxa-2,9-diazaheptadec-16-enoicacid, 4,4,6,16 (or 4,6,6,16)-tetramethyl-10,15-dioxo-,2-[(2-methyl-1-oxo-2-propen-1-yl)oxy]ethyl ester (UDMA), 2.50 g (16.0072 mmol) 2-Vinyloxyethoxyethyl methacrylate (VEEM), 0.1098 g (0.4491 mmol) tert-Butyl (tert-butyldimethylsilyl) glyoxylate (DKSi) and 0.1090 g (0.2558 mmol) diphenyliodonium hexafluoro phosphate (DPI) were mixed homogeneously. The polymerization enthalpy measured with the DSC 7 (Perkin Elmer) was $\Delta_R H=-44.4\pm5.6$ kJ/mol. The flexural strength measured for the polymerized blend was 81.7±8.4 MPa, and the E-modulus was 1973±78 MPa.

Example 8: DKSi/PI2074 for the Hybrid Polymerization of the Methacrylate/Divinylether/Epoxide Blend UDMA/DEGDVE/EPOX-Si 5.0000 g (10.6256 mmol) 11,14-Dioxa-2,9-diazaheptadec-16-enoicacid, 4,4,6,16 (or 4,6,6,16)-tetramethyl-10,15-dioxo-,2-[(2-methyl-1-oxo-2-propen-1-yl)oxy]ethyl ester (UDMA), 2.50 g (15.8028 mmol) diethyleneglycol divinylether (DEGDVE), 2.5000 g (6.5327 mmol) 1,1,3,3-tetramethyl-1,3-bis[2-(7-oxabicyclo[4.1.0] hept-3-yl) ethyl] disiloxane (EPOX-Si), 0.1974 g (0.8075 mmol) tert-butyl (tert-butyldimethylsilyl) glyoxylate (DKSi) and 0.3899 g (0.3837 mmol) 4-isopropyl-4'-methyldiphenyliodonium tetrakis (pentafluorophenyl) borate (PI2074) were mixed homogeneously. The polymerization enthalpy measured with the DSC 7 (Perkin Elmer) was $\Delta_R H=-30.5\pm3.3$ kJ/mol.

Example 9: DKSi/PI2074 for the Hybrid Polymerization of Methacrylate/Monomer Compound Having Radically Polymerizable Methacrylate and Cationically Polymerizable Divinylether Group/Divinylether Blend UDMA/GDM/VEEM/DEGDVE 4.5000 g (9.5631 mmol) 11,14-Dioxa-2,9-diazaheptadec-16-enoicacid, 4,4,6,16 (or 4,6,6,16)-tetramethyl-10,15-dioxo-,2-[(2-methyl-1-oxo-2-propen-1-yl)oxy]ethyl ester (UDMA), 3.1000 g (13.5818 mmol) Glycerine dimethacrylate, 1,1000 g (7,0432 mmol) 2-Vinyloxyethoxyethyl methacrylate (VEEM), 1,3000 g (8,2174 mmol) Diethyleneglycol divinylether (DEGDVE), 0.0984 g (0.4025 mmol) tert-Butyl (tert-butyldimethylsilyl) glyoxylate (DKSi) and 0.1933 g (0.1902 mmol) 4-Isopropyl-4'-methyldiphenyliodonium tetrakis(pentafluorophenyl) borate (PI2074) were mixed homogeneously. The polymerization enthalpy measured with the DSC 7 (Perkin Elmer) was $\Delta_R H=-37.2\pm2.7$ kJ/mol. The flexural strength measured for the polymerized blend was 57.1±12.6 MPa, and the E-modulus was 1714±114 MPa.

Example 10: CQ/Ph$_3$GeH/PI2074 for the Hybrid Polymerization of Methacrylate/Epoxy Blend UDMA/EPOX-Si 2.0000 g (4.2503 mmol) 11,14-Dioxa-2,9-diazaheptadec-16-enoicacid, 4,4,6,16 (or 4,6,6,16)-tetramethyl-10,15-dioxo-,2-[(2-methyl-1-oxo-2-propen-1-yl)oxy]ethyl ester (UDMA), 2.0000 g (5.2262 mmol) 1,1,3,3-tetramethyl-1,3-bis[2-(7-oxabicyclo[4.1.0] hept-3-yl) ethyl] disiloxane (EPOX-Si), 0.0851 g (0.5117 mmol) camphor quinone (CQ), 0.0853 g (0.2797 mmol) triphenyl germanium hydride and 0.1680 g (0.1653 mmol) 4-Isopropyl-4'-methyldiphenyliodonium tetrakis(pentafluorophenyl) borate (PI2074) were mixed homogeneously. The polymerization enthalpy measured with the DSC 7 (Perkin Elmer) was $\Delta_R H=-51.6\pm0.8$ kJ/mol.

Reference Example 1: UDMA/EPOX-Si and Reference Initiator System CQ/CARET/PI2074 for the Hybrid Polymerization of Methacrylate/EPOX-Si Blends CQ/CARET/PI2074 was found to represent an efficient initiating systems for the hybrid polymerization of methacrylate/EPOX-Si blends, as can be gathered from Table 2 above.

The results for the reference initiator system CQ/CARET/PI2074 are shown in FIGS. 17A and 17B. After 50-90 s upon irradiation with SmartLite Focus, almost full conversion of the methacrylate functions was obtained, but only about 30 to 40% of the epoxy groups of EPOX-Si were converted, as can be gathered from FIG. 17A.

Remarkably, with the reference initiator system CQ/CARET/PI2074, a dark polymerization of the polymer obtained in FIG. 17A occurs which provides an improved final conversion of epoxy functions being about 50 to 55% upon storage at 37° C. for about half to one and a half day, as can be gathered from FIG. 17B.

Example 11: DKSi/PI2074/CARET for the Hybrid Polymerization of Methacrylate/Monomer Compound Having Radically Polymerizable Methacrylate and Cationically Polymerizable Divinylether Group Blend UDMA/VEEM The DKSi/PI2074/CARET system was able to initiate both radical and cationic polymerizations, and therefore it was used for the synthesis of interpenetrating polymer networks (IPNs) through the polymerization of a blend of a compound having radically polymerizable groups, such as methacrylate, and a compound having both cationically polymerizable group(s) (e.g. vinylether) and radically polymerizable groups (e.g. methacrylate). Examples are provided here with the polymerization of a UDMA/VEEM blend shown in FIGS. 18 and 19.

The polymerization was found to be rather sequential, that is, the radical polymerization started first, and the cationic polymerization started after a short inhibition period, as can be gathered from FIG. 18. Furthermore, as can be gathered from FIG. 19, the already good conversion of vinylether groups (VE) obtained with the initiator system DKSi/PI2074 were significantly further improved by adding CARET to the initiator system.

CONCLUSIONS

The Examples show that an initiator system comprising a radical polymerization initiator of formula (I) and a cationic polymerization initiator of formula (II) is surprisingly suitable for a hybrid polymerization of a homogenous phase (a) comprising monomer combinations (i) and (ii), (i) and (iii), or (i), (ii) and (iii), wherein
  (i) represents one or more compounds having one or more radically polymerizable carbon-carbon double bonds;
  (ii) represents one or more compounds having one or more cationically polymerizable groups;
  (iii) represents one or more compounds having a combination of one or more radically polymerizable carbon-carbon double bonds and one or more cationically polymerizable groups.

The invention claimed is:

1. Dental composition comprising
  (a) a homogeneous phase comprising monomer combinations (i) and (ii), (i) and (iii),
    (ii) and or (i), (ii) and (iii), or comprising monomer (iii), wherein
    (i) represents one or more compounds having one or more radically polymerizable carbon-carbon double bonds;
    (ii) represents one or more compounds having one or more cationically polymerizable groups; and
    (iii) represents one or more compounds having a combination of one or more radically polymerizable carbon-carbon double bonds and one or more cationically polymerizable groups;
  (b) an initiator system comprising
    (iv) one or more radical polymerization initiator of the following formula (I):

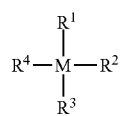

(I)

wherein
  M is Ge or Si;
  $R^1$, $R^2$ and $R^3$ may be the same or different, independently represent an organic group, and
  $R^4$ is selected from a hydrogen atom, a group of a formula (V):

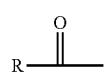

(V)

wherein R (i) is a group of the following formula (VII):

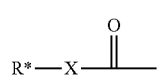

(VII)

wherein
  X represents a single bond, an oxygen atom or a group NR', wherein R' represents a substituted or unsubstituted hydrocarbyl group:
  R* represents a substituted or unsubstituted hydrocarbyl proup, a trihydrocarbylsilyl group, a mono(hydrocarbylcarbonyl)dihydrocarbylsilyl group or a di(hydrocarbylcarbonyl)monohydrocarbylsilyl group; or
  (ii) when M is Si, R may be a substituted or unsubstituted hydrocarbyl group;
  and a combination thereof;
  provided that when $R^4$ is a hydrogen atom, the initiator system further comprises a sensitizer compound having a light absorption maximum in the range from 300 to 600 nm;
  (v) a cationic polymerization initiator, which is a compound selected from the following formula (II), (III) and (IV):

(II)

wherein
  $R^5$ and $R^6$, which may be the same or different, independently represent an aryl group which may have a substituent; and
  $Y^-$ represents an anion;

(III)

wherein
  $R^7$, $R^8$ and $R^9$ which may be the same or different, independently represent an aryl group which may have a substituent; and
  $Y^-$ represents an anion;

(IV)

$R^{10}$, $R^{11}$, $R^{12}$, and $R^{13}$ which may be the same or different, independently represent an alkyl or aryl group which may have a substituent; and
  $Y^-$ represents an anion.

2. The dental composition according to claim 1,
wherein R of the formula (V) has the following formula (VI):

(VI)

wherein M, $R^1$, $R^2$ and $R^3$ have the same meaning as defined for formula (I), whereby the compound of formula (I) may be symmetrical or unsymmetrical.

3. The dental composition according to claim 1, wherein M is Si.

4. The dental composition according to claim 1, wherein M is Ge.

5. The dental composition according to claim 1, wherein the radically polymerizable carbon-carbon double bonds are carbon-carbon double bonds of a (meth)acryloyl group or a (meth)acrylamide group.

6. The dental composition according to claim 1, wherein the cationically polymerizable groups are epoxide groups, oxetane groups, vinyl ether groups, aziridine groups, or azetidine groups.

7. The dental composition according to claim 1, wherein in compound (i), the radically polymerizable carbon-carbon double bond(s) is/are (meth)acryloyl group(s).

8. The dental composition according to claim 1, wherein in compound (ii), the cationically polymerizable groups are epoxide groups, oxetane groups, or vinyl ether groups.

9. The dental composition according to claim 1, wherein in compound (iii), the radically polymerizable carbon-carbon double bond(s) is/are carbon-carbon double bonds of (meth)acryloyl group(s), and the cationically polymerizable group(s) is/are vinyl ether groups.

10. The dental composition according to claim 1, wherein compound (i) has two or more radically polymerizable carbon-carbon double bonds.

11. The dental composition according to claim 1. which comprises a compound of formula (II).

12. The dental composition according to claim 1, which comprises a compound of formula (Ill) or (IV).

13. The dental composition according to claim 1, wherein the dental composition is a dental adhesive composition, a bonding agent, a pit and fissure sealant, a dental desensitizing composition, a pulp capping composition, a dental composite, a flowable dental composite, a dental glass ionomer cement, a dental cement, resin modified glass lonomers, or a dental root canal sealer composition.

14. The dental composition according to claim 1, which contains 0.1 to 5 percent by weight of the initiator system.

15. The dental composition according to claim 1, wherein the homogeneous phase (a) contains components (i), (ii) and (iii) in a weight ratio (i)/((ii)+(iii)) of from 0.1 to 10.

* * * * *